United States Patent
White et al.

(10) Patent No.: US 9,861,644 B2
(45) Date of Patent: Jan. 9, 2018

(54) STABILIZED MODIFIED RELEASE VITAMIN D FORMULATION AND METHOD OF ADMINISTERING SAME

(71) Applicant: OPKO IRELAND GLOBAL HOLDINGS, LTD., Grand Cayman (KY)

(72) Inventors: Jay A. White, Newmarket (CA); Samir P. Tabash, Whitby (CA); Sammy A. Agudoawu, Mississauga (CA); Joel Z. Melnick, Wilmette, IL (US)

(73) Assignee: OPKO IRELAND GLOBAL HOLDINGS, LTD., Grand Cayman (KY)

(*) Notice: Subject to any disclaimer, the term of this patent is extended or adjusted under 35 U.S.C. 154(b) by 0 days.

(21) Appl. No.: 14/213,285

(22) Filed: Mar. 14, 2014

(65) Prior Publication Data
US 2014/0349979 A1    Nov. 27, 2014

Related U.S. Application Data

(60) Provisional application No. 61/801,896, filed on Mar. 15, 2013.

(51) Int. Cl.
| | |
|---|---|
| *A61K 31/593* | (2006.01) |
| *A61K 9/20* | (2006.01) |
| *A61K 9/28* | (2006.01) |
| *A61K 9/48* | (2006.01) |
| *A61K 47/38* | (2006.01) |
| *A61K 47/44* | (2017.01) |
| *A61K 31/592* | (2006.01) |

(52) U.S. Cl.
CPC .......... *A61K 31/593* (2013.01); *A61K 9/2054* (2013.01); *A61K 9/2866* (2013.01); *A61K 9/4866* (2013.01); *A61K 31/592* (2013.01); *A61K 47/38* (2013.01); *A61K 47/44* (2013.01)

(58) Field of Classification Search
None
See application file for complete search history.

(56) References Cited

U.S. PATENT DOCUMENTS

| | | |
|---|---|---|
| 3,565,924 A | 2/1971 | DeLuca et al. |
| 3,833,622 A | 9/1974 | Babcock et al. |
| 3,880,894 A | 4/1975 | De Luca et al. |
| 4,004,003 A | 1/1977 | Babcock et al. |
| 4,230,701 A | 10/1980 | Holick et al. |
| 4,335,120 A | 6/1982 | Holick et al. |
| 4,555,364 A | 11/1985 | DeLuca et al. |
| 4,668,517 A | 5/1987 | Weber et al. |
| 4,684,524 A | 8/1987 | Eckenhoff et al. |
| 4,695,591 A | 9/1987 | Hanna et al. |
| 4,721,613 A | 1/1988 | Urquhart et al. |
| 4,729,895 A | 3/1988 | Makino et al. |
| 4,755,544 A | 7/1988 | Makino et al. |
| 5,026,559 A | 6/1991 | Eichel et al. |
| 5,160,742 A | 11/1992 | Mazer et al. |
| 5,328,903 A | 7/1994 | Ishii et al. |
| 5,342,626 A | 8/1994 | Winston, Jr. et al. |
| 5,354,743 A | 10/1994 | Thys-Jacobs |
| 5,403,831 A | 4/1995 | DeLuca et al. |
| 5,431,917 A | 7/1995 | Yamamoto et al. |
| 5,472,712 A | 12/1995 | Oshlack et al. |
| 5,487,900 A | 1/1996 | Itoh et al. |
| 5,529,991 A | 6/1996 | Knutson et al. |
| 5,593,690 A | 1/1997 | Akiyama et al. |
| 5,602,116 A | 2/1997 | Knutson et al. |
| 5,614,513 A | 3/1997 | Knutson et al. |
| 5,622,941 A | 4/1997 | Knutson et al. |
| 5,693,615 A | 12/1997 | Stone |
| 5,707,980 A | 1/1998 | Knutson et al. |
| 5,756,123 A | 5/1998 | Yamamoto et al. |
| 5,783,215 A | 7/1998 | Arwidsson et al. |
| 5,795,882 A | 8/1998 | Bishop et al. |
| 5,861,386 A | 1/1999 | Knutson et al. |
| 5,869,473 A | 2/1999 | Knutson et al. |
| 5,958,451 A | 9/1999 | Chen |
| 6,034,075 A | 3/2000 | Thys-Jacobs |
| 6,051,567 A | 4/2000 | Abrahamson et al. |
| 6,121,469 A | 9/2000 | Norman et al. |
| 6,133,250 A | 10/2000 | Knutson et al. |

(Continued)

FOREIGN PATENT DOCUMENTS

| | | |
|---|---|---|
| CA | 2241205 A1 | 7/1997 |
| EP | 0 227 836 A1 | 7/1987 |

(Continued)

OTHER PUBLICATIONS

Al-Aly, Z., "Changes in Serum 25-Hydroxyvitamin D and Plasma Intact PTH Levels Following Treatment with Ergocalciferol in Patients With CKD," Am. J. Kid. Dis., 50(1):59-68 (2007).
Andress, "Vitamin D in chronic kidney disease: A systematic role for selective vitamin D receptor activation," *Kidney Int.*, 69:33-43 (2006).
Arekat et al., "Dramatic Improvement of BMD Following Vitamin D Therapy in a Bone Marrow Transplant Recipient," *J. Clin. Densitometry*, 5:267-271 (2002).
Armas et al., "Vitamin $D_2$ is Much Less Effective than Vitamin $D_3$ in Humans," *J. Clin. Endocrinol. Metab.*, 89:5387-5391 (2004).
Bagnis et al., "Biochemical and Hormonal Short-Term Effects of 25-hydroxyvitamin D3 in Patients on Continuous Peritoneal Dialysis," *Ital. J. Mineral Electrolyte Metab.*, 12:73-76 (1998).
Bailie et al. "Comparative Review of the Pharmacokinetics of Vitamin D Analogues," *Seminars in Dialysis*, 15(5):352-357 (2000).
Baird et al., "Steroid Dynamics Under Steady-State Conditions," *Recent Prog. Horm. Res.*, 25:611-664 (1969).

(Continued)

*Primary Examiner* — Jessica Worsham
(74) *Attorney, Agent, or Firm* — Marshall, Gerstein & Borun LLP

(57) ABSTRACT

A stabilized formulation for controlled release of a vitamin D compound is disclosed. The formulation comprises one or both of 25-hydroxyvitamin $D_2$ and 25-hydroxyvitamin $D_3$ and a cellulosic compound. The stabilized formulations exhibit a stable dissolution profile following exposure to storage conditions and demonstrate improved pharmacokinetic parameters compared to unstabilized formulations.

36 Claims, 10 Drawing Sheets

(56) References Cited

U.S. PATENT DOCUMENTS

| | | | |
|---|---|---|---|
| 6,139,875 A | 10/2000 | Adams et al. |
| 6,147,064 A | 11/2000 | Knutson et al. |
| 6,150,346 A | 11/2000 | Knutson et al. |
| 6,190,591 B1 | 2/2001 | van Lengerich |
| 6,190,695 B1 | 2/2001 | Hoshino et al. |
| 6,228,849 B1 | 5/2001 | Thys-Jacobs |
| 6,242,434 B1 | 6/2001 | Bishop et al. |
| 6,265,392 B1 | 7/2001 | Abrahamson et al. |
| 6,274,169 B1 | 8/2001 | Abrahamson et al. |
| 6,288,849 B1 | 9/2001 | Teramoto |
| 6,340,473 B1 | 1/2002 | Tanner et al. |
| 6,342,249 B1 | 1/2002 | Wong et al. |
| 6,375,981 B1 | 4/2002 | Gilleland et al. |
| 6,376,479 B1 | 4/2002 | Knutson et al. |
| 6,380,408 B1 | 4/2002 | Posner et al. |
| 6,413,463 B1 | 7/2002 | Yamamoto et al. |
| 6,432,936 B1 | 8/2002 | DeLuca et al. |
| 6,503,893 B2 | 1/2003 | Bishop et al. |
| 6,521,608 B1 | 2/2003 | Henner et al. |
| 6,524,788 B1 | 2/2003 | Cantor |
| 6,569,463 B2 | 5/2003 | Patel et al. |
| 6,572,888 B2 | 6/2003 | Byrd |
| 6,582,727 B2 | 6/2003 | Tanner et al. |
| 6,596,314 B2 | 7/2003 | Wong et al. |
| 6,645,527 B2 | 11/2003 | Oshlack et al. |
| 6,770,295 B1 | 8/2004 | Kreilgård et al. |
| 6,893,658 B1 | 5/2005 | Iida et al. |
| 6,903,083 B2 | 6/2005 | Knutson et al. |
| 6,911,217 B1 | 6/2005 | Gren et al. |
| 6,923,988 B2 | 8/2005 | Patel et al. |
| 6,929,803 B2 | 8/2005 | Wong et al. |
| 6,949,256 B2 | 9/2005 | Fonkwe et al. |
| 6,982,258 B2 | 1/2006 | Posner et al. |
| RE39,079 E | 4/2006 | Tanner et al. |
| 7,033,996 B2 | 4/2006 | Christakos |
| 7,056,655 B2 | 6/2006 | Cantor |
| 7,101,865 B2 | 9/2006 | Posner et al. |
| 7,122,530 B2 | 10/2006 | Bishop et al. |
| 7,189,843 B2 | 3/2007 | Tsai et al. |
| 7,226,932 B2 | 6/2007 | Gokhale et al. |
| 7,255,921 B2 | 8/2007 | Kamaguchi et al. |
| 7,422,758 B2 | 9/2008 | Block et al. |
| 7,632,518 B2 | 12/2009 | Tritsch et al. |
| 7,807,194 B2 | 10/2010 | Modliszewski et al. |
| 7,816,341 B2 | 10/2010 | Sewall et al. |
| 7,846,475 B2 | 12/2010 | Shiraishi et al. |
| 8,088,410 B2 | 1/2012 | Tritsch et al. |
| 8,101,203 B2 | 1/2012 | Cao |
| 8,101,204 B2 | 1/2012 | Cao |
| 8,142,811 B2 | 3/2012 | Oshlack et al. |
| 8,207,149 B2 | 6/2012 | Tabash et al. |
| 8,231,896 B2 | 7/2012 | Tanner et al. |
| 8,268,352 B2 | 9/2012 | Vaya et al. |
| 8,293,270 B2 | 10/2012 | Sukuru |
| 8,361,488 B2 | 1/2013 | Bishop et al. |
| 8,377,470 B2 | 2/2013 | Tanner et al. |
| 8,426,391 B2 | 4/2013 | Bishop et al. |
| 8,759,328 B2 | 6/2014 | Deluca et al. |
| 8,778,373 B2 | 7/2014 | Bishop et al. |
| 8,906,410 B2 | 12/2014 | Bishop et al. |
| 8,992,971 B2 | 3/2015 | Yang |
| 9,017,720 B2 | 4/2015 | Andersen et al. |
| 2001/0028896 A1 | 10/2001 | Byrd |
| 2001/0036472 A1 | 11/2001 | Wong et al. |
| 2002/0018810 A1 | 2/2002 | Oshlack et al. |
| 2002/0031798 A1 | 3/2002 | Anazawa et al. |
| 2002/0081331 A1 | 6/2002 | Tanner et al. |
| 2002/0128240 A1 | 9/2002 | Mazess |
| 2002/0155154 A1 | 10/2002 | Wong et al. |
| 2002/0183288 A1 | 12/2002 | Mazess et al. |
| 2003/0129194 A1 | 7/2003 | Mazess et al. |
| 2003/0138482 A1 | 7/2003 | Fonkwe et al. |
| 2003/0157560 A1 | 8/2003 | Cantor |
| 2004/0043971 A1 | 3/2004 | Mazess et al. |
| 2004/0101554 A1 | 5/2004 | Kirschner et al. |
| 2005/0019374 A1 | 1/2005 | Modliszewski et al. |
| 2005/0037064 A1 | 2/2005 | Basquin et al. |
| 2005/0069579 A1 | 3/2005 | Kamaguchi et al. |
| 2005/0101576 A1 | 5/2005 | Whitehouse et al. |
| 2005/0106233 A1 | 5/2005 | Andersen et al. |
| 2005/0124591 A1 | 6/2005 | Tian et al. |
| 2005/0143358 A1 | 6/2005 | DeLuca et al. |
| 2005/0148557 A1 | 7/2005 | Tian et al. |
| 2005/0148558 A1 | 7/2005 | Knutson et al. |
| 2005/0186268 A1 | 8/2005 | Hoshi et al. |
| 2005/0287213 A1 | 12/2005 | Wong et al. |
| 2006/0009425 A1 | 1/2006 | Delgado-Herrera et al. |
| 2006/0019933 A1 | 1/2006 | Boardman et al. |
| 2006/0029660 A1 | 2/2006 | Fonkwe et al. |
| 2006/0034937 A1 | 2/2006 | Patel |
| 2006/0193877 A1 | 8/2006 | Tengler et al. |
| 2006/0210610 A1 | 9/2006 | Davidson et al. |
| 2006/0223119 A1 | 10/2006 | Cantor |
| 2006/0228808 A1 | 10/2006 | Clarke et al. |
| 2006/0257481 A1 | 11/2006 | Gurney et al. |
| 2007/0026067 A1 | 2/2007 | Yam et al. |
| 2007/0032461 A1* | 2/2007 | Adorini ............ C07C 401/00 514/167 |
| 2007/0122477 A1 | 5/2007 | Bishop et al. |
| 2007/0190146 A1 | 8/2007 | Roger et al. |
| 2008/0109983 A1 | 5/2008 | Davis |
| 2008/0134937 A1 | 6/2008 | Yang |
| 2008/0317764 A1 | 12/2008 | Huber et al. |
| 2009/0137536 A1 | 5/2009 | Mazess et al. |
| 2009/0176748 A1* | 7/2009 | Tabash ............ A61K 9/4858 514/167 |
| 2009/0311316 A1 | 12/2009 | Bishop et al. |
| 2011/0182986 A1 | 7/2011 | Speirs et al. |
| 2011/0300210 A1 | 12/2011 | Swanson et al. |
| 2014/0088202 A1 | 3/2014 | Cade et al. |
| 2014/0248400 A1 | 9/2014 | Phonchareon et al. |
| 2015/0119472 A1 | 4/2015 | Shuai et al. |
| 2015/0119473 A1 | 4/2015 | Shuai et al. |

FOREIGN PATENT DOCUMENTS

| | | |
|---|---|---|
| EP | 0 508 756 A1 | 10/1992 |
| EP | 0 387 808 B1 | 5/1993 |
| EP | 1 165 061 B1 | 10/2005 |
| EP | 2 148 661 B1 | 12/2012 |
| JP | 08-92098 A | 9/1973 |
| JP | 58-032823 | 2/1983 |
| JP | 04-208225 A | 7/1992 |
| JP | 07-242550 A | 9/1995 |
| JP | 08-092098 A | 4/1996 |
| JP | 10-158171 A | 6/1998 |
| JP | 2004-175750 A | 6/2004 |
| JP | 2005-513419 A | 5/2005 |
| WO | WO-1991/012807 A1 | 9/1991 |
| WO | WO-1991/016899 A1 | 11/1991 |
| WO | WO-1994/000128 A1 | 1/1994 |
| WO | WO-96/001621 A1 | 1/1996 |
| WO | WO-1996/000074 A1 | 1/1996 |
| WO | WO-1996/031215 A1 | 10/1996 |
| WO | WO-1997/011053 A1 | 3/1997 |
| WO | WO-1998/018610 A1 | 5/1998 |
| WO | WO-98/29105 A2 | 7/1998 |
| WO | WO-1999/011272 A1 | 3/1999 |
| WO | WO-2000/021504 A1 | 4/2000 |
| WO | WO-2000/035419 A2 | 6/2000 |
| WO | WO-00/61123 A2 | 10/2000 |
| WO | WO-2001/037808 A1 | 5/2001 |
| WO | WO-2003/039521 A1 | 5/2003 |
| WO | WO-2003/039572 A1 | 5/2003 |
| WO | WO-2003/047595 A1 | 6/2003 |
| WO | WO-03/088976 A1 | 10/2003 |
| WO | WO-2004/028515 A1 | 4/2004 |
| WO | WO-2004/058235 A2 | 7/2004 |
| WO | WO-2004/080467 A2 | 9/2004 |
| WO | WO-2004/098617 A2 | 11/2004 |
| WO | WO-2004/101554 A1 | 11/2004 |
| WO | WO-2004/110391 A2 | 12/2004 |
| WO | WO-2005/011652 A2 | 2/2005 |
| WO | WO-2005/123120 A1 | 12/2005 |

(56) References Cited

FOREIGN PATENT DOCUMENTS

| | | |
|---|---|---|
| WO | WO-2006/052452 A1 | 5/2006 |
| WO | WO-2006/059180 A2 | 6/2006 |
| WO | WO-2006/113505 A2 | 10/2006 |
| WO | WO-2007/039193 A1 | 4/2007 |
| WO | WO-2007/039569 A2 | 4/2007 |
| WO | WO-2007/047327 A2 | 4/2007 |
| WO | WO-2007/050724 A2 | 5/2007 |
| WO | WO-2007/050975 A2 | 5/2007 |
| WO | WO-2007/053608 A2 | 5/2007 |
| WO | WO-2007/068287 A1 | 6/2007 |
| WO | WO-2007/092755 A2 | 8/2007 |
| WO | WO-2007/146004 A1 | 12/2007 |
| WO | WO-2008/008608 A2 | 1/2008 |
| WO | WO-2008/043449 A1 | 4/2008 |
| WO | WO-2008/134512 A1 | 11/2008 |
| WO | WO-2008/134523 A1 | 11/2008 |
| WO | WO-2009/047644 A2 | 4/2009 |
| WO | WO-2009/101132 A1 | 8/2009 |
| WO | WO-2009/101137 A1 | 8/2009 |
| WO | WO-2010/011906 A1 | 1/2010 |
| WO | WO-2010/034342 A1 | 4/2010 |
| WO | WO-2011/031621 A2 | 3/2011 |
| WO | WO-2011/095388 A1 | 8/2011 |
| WO | WO-2012/018329 A1 | 2/2012 |
| WO | WO-2012/076429 A1 | 6/2012 |
| WO | WO-2012/091569 A1 | 7/2012 |
| WO | WO-2012/117236 A1 | 9/2012 |
| WO | WO-2012/145491 A2 | 10/2012 |
| WO | WO-2014/202754 A1 | 12/2014 |

OTHER PUBLICATIONS

Barger-Lux M.J. et al., "Vitamin D and Its Major Metabolites: Serum Levels After Graded Oral Dosing in Healthy Men" *Osteoporosis International*, United Kingdom, 8(3):222-230 (1998).

Barreto et al., "25-Hydroxyvitamin $D_3$, the Prohormone of 1,25-Dihydroxyvitamin $D_3$, Inhibits the Proliferation of Primary Prostatic Epithelial Cells," *Cancer Epidemiol, Biomarkers & Prevention*, 9:265-270 (2000).

Beckman, et al., "Up-Regulation of the Intestinal 1, 25-Dihydroxyvitamin D Receptor During Hypervitaminosis D: A Comparison Between Vitamin D2 and Vitamin D31," Biochemical and Biophysical Research Communications, vol. 169, No. 3, pp. 910-915 (Jun. 29, 1990).

Beer et al., "Pharmacokinetics and Tolerability of a Single Dose of DN-101, a New Formulation of Calcitriol, in Patients with Cancer," *Clin. Cancer Res.*, 11:7794-7799 (2005).

Bell et al., "Evidence that 1,25-Dihydroxyvitamin D3 Inhibits the Hepatic Production of 25-Hydroxyvitamin D in Man," *J. Clin. Invest.*, 74:1540-1544 (1984).

Belostotsky et al., "A single high dose of ergocalciferol can be used to boost 25-hydroxyvitamin D levels in children with kidney disease," *Pediatr Nephrol*, 24:625-626 (2009).

Bianchi et al., "No Difference in Intestinal Strontium Absorption After an Oral or an Intravenous 1,25(OH)2D3 Bolus in Normal Subjects," *J. Bone Miner. Res.*, 14:1789-1795 (1999).

Blair et al., "Prevalence of vitamin D [25(OH)D] deficiency and effects of supplementation with ergocalciferol (vitamin D2) in stage 5 chronic kidney disease patients." *J.Ren Nutr.*, 18: 375-382 (2008).

Bordier et al., "Evolution of renal osteodystrophy: Correlation of bone histomorphometry and serum mineral and immunoreactive parathyroid hormone values before and after treatment with calcium carbonate or 25-hydroxycholecalciferol," *Kidney Int Suppl*, 2:S102-S112 (1975).

Bouillon et al., "Influence of dialysate calcium concentration and vitamin D on serum parathyroid hormone during repetitive dialysis," *Kidney Int.*, 7:422-432 (1975).

Brossard et al. "Influence of Glomerular Filtration Rate on Non-(1-84) Parathyroid Hormone (PTH) Detected by Intact PTH Assays," *Clinical Chemistry*, 46(5):697-703 (2000).

Brown et al., "Vitamin D Analogues for Secondary Hyperparathyroidism," Nephrol Dial Transplant, 17[Suppl. 10]:10-19 (2002).

Buccianti et al., "Effects of Calcifediol Treatment on the Progression of Renal Osteodystrophy during Continuous Ambulatory Peritoneal Dialysis," *Nephron*, 56:353-356 (1990).

Budavari (ed.), *Merck Index: an Encyclopedia of Chemicals, Drugs, and Biologicals*, 11th Edition, Merck & Co., 9927-9930 (1989).

Bulla et al., "Renal bone disorders in children: therapy with vitamin D3 or 1,25-dihydroxycholecalciferol," *Proc.Eur.Dial.Transplant. Assoc.*, 16: 644-648 (1979).

Chandra et al., "Cholecalciferol (vitamin D3) therapy and vitamin D insufficiency in patients with chronic kidney disease: a randomized controlled pilot study," *Endocr.Pract.*, 14: 10-17 (2008).

Claris-Appiani et al., "Phosphate-Induced PTH Stimulation and Calcitriol Treatment in Children with Early Chronic Renal Insufficiency," *J. Bone Miner. Met.*, 12:S91-S97 (1994).

Coburn, "An Update on Vitamin D as Related to Nephrology Practice: 2003," *Kidney International*, vol. 64, Supplement 87, pp. S125-S130 (2003).

Coburn, et al., "Use of Active Vitamin D Sterols in Patients with Chronic Kidney Disease, Stages 3 and 5," *Kidney International*, vol. 63, Supplement 85, pp. S49-S53 (2003).

Coen et al., "1,25(OH)2D3 and 25-OHD3 in the Treatment of Renal Osteodystrophy: Comparison of Combined Versus 1,25(OH)2D3 Administration Alone," *Miner. Electrolyte Metab.*, 9:19-27 (1983).

Coen et al., "25-hydroxycholecalciferol in the treatment of renal osteodystrophy in haemodialysed patients," *Int J Artificial Organs*, 2(6): 278-281 (1979).

Cohen-Solal et al., "Non-Aluminic Adynamic Bone Disease in Non-Dialyzed Uremic Patients: A New Type of Osteopathy Due to Overtreatment?" *Bone*, 13:1-5 (1992).

Collet et al. "Modified-Release Peroral Dosage Forms," Aulton (ed.), Pharmaceutics: The Science of Dosage Forms, Churchill Livingston, London, pp. 289-305 (2002).

Colodro et al., "Effect of 25-Hydroxy-Vitamin D3 on Intestinal Absorption of Calcium in Normal Man and Patients With Renal Failure," *Metabolism*, 27(6):745-753 (1978).

Cooke et al., "Vitamin D-Binding Protein (Gc-Globulin): Update 1995," *Endocrine Rev.*, 4:125-128 (1995).

Coyne et al., "Paricalcitol Capsule for the Treatment of Secondary Hyperparathyroidism in Stages 3 and 4 CKD," *American Journal of Kidney Diseases*, 47(2):263-276 (2006).

Daisley-Kydd et al., "Calcitriol in the Management of Secondary Hyperparathyroidism of Renal Failure," *Pharmacotherapy.*, 16:619-630 (1996).

Davies, M. et al. The Absorption and Metabolism of Vitamin D3 from Parenteral Injection Sites, Proceedings of the Workshop on Vitamin D, 4th, Vitam. D: Basic Res. Its Clin. Appl. (1979), abstract.

DB-Pharma, "Dedrogyl 15 Mg/10ML Calcifediol Oral Drops, Solution," Marketing Authorization No. 317 863.2 (2000).

DeLuca, "Treatment of renal osteodystrophy with 25-hydroxycholecalciferol," *Arch Intern Med*, 126(5):896-899 (1970).

Deroisy et al., "Comparison of the Short-Term Effects of Three Oral Calcium-Vitamin D Formulations and Placebo on Calcium Metabolism," *Curr. Ther. Res.*, 59:370-378 (1998).

DeVille et al., "Effect of Ergocalciferol Supplementation on Serum Parathyroid Hormone and Serum 25-Hydroxyvitamin D in Chronic Kidney Disease," *Nephrology*, 11:555-559 (2006).

*Dietary Reference Intakes for Calcium, Phosphorus, Magnesium, Vitamin D, and Fluoride*, Standing Committee on the Scientific Evaluation of Dietary Reference Intakes, Food and Nutrition Board, Institute of Medicine, National Academy Press, Washington DC, pp. 250-287 (1997).

*Dietary Supplement Fact Sheet: Vitamin D*, National Institutes of Health, Office of Dietary Supplements (last update: Aug. 5, 2005), retrieved from <URL: http:ods.od.nih.gov/factsheets/vitamind.asp> on Aug. 31, 2007.

*Disease and Vitamin D*, University of California Riverside, retrieved from Internet, <URL: <http://vitamind.ucr.edu/disease.html>> (last update: May 19, 1999).

(56) References Cited

OTHER PUBLICATIONS

Disintegration, chapter 701; Dissolution, chapter 711; Distilling Range, chapter 721; Drug Release, chapter 724; Electrophoresis, chapter 726; pp. 276-292, in: U.S. Pharmacopeia vol. 30.
Dogan et al., "Effect of depot oral cholecalciferol treatment on secondary hyperparathyroidism in stage 3 and stage 4 chronic kidney diseases patients," *Ren Fail.*, 30: 407-410 (2008).
Drueke et al., Recurrence of hyperparathyroidism from autografted parathyroid fragments in uremic patients in spite of administration of 25(OH)D3 and 1a(OH)D3. In: Vitamin D. Basic Research and its Clinical Application, (Eds. Norman AW, Schaefer K, Herrath Dv, Grigoleit HG, Coburn JW, DeLuca HF, Mawer EB, and Suda T), pp. 791-794. Willem de Gruyter, New York (1979).
Dusso et al, "Metabolic Clearance Rate and Production Rate of Calcitriol in Uremia," *Kidney Int.*, 35 860-864 (1989).
Dusso et al., "Extra-renal production of calcitriol in chronic renal failure," *Kidney Int.*, 34:368-375 (1988).
Dusso et al., "Extrarenal Production of Calcitrol in Normal and Uremic Humans," *Journal of Clinical Endocrinology and Metabolism*, 72(1):157-164 (1991).
Eastwood et al., "Biochemical and histological effects of 1,25 dihydroxycholecalciferol (1,25-DHCC) in the osteomalacia of chronic renal failure," *J Urol Nephrol* (Paris,) 80(12): 984-985 (1974).
Eastwood et al., "The contrasting effects on bone histology of vitamin D and of calcium carbonate in the osteomalacia of chronic renal failure," *Clin Sci Molec Med*, 47:23-42 (1974).
Eastwood et al., "The Effect of 25-Hydroxy Vitamin D3 in the Osteomalacia of Chronic Renal Failure," *Clin. Sci. Molec. Med.*, 52:499-508 (1977).
Fernandez et al., "Guidelines for Dosing of Intravenous Calcitriol in Dialysis Patients with Hyperparathyroidism," *Nephrol. Dial. Transplant.*, 11:96-101 (1996).
Fournier et al., "1 alpha hydroxycholecalciferol and 25 hydroxycholecalciferol in renal bone disease." *Proc. Eur. Dial. Transplant. Assoc.* 12: 227-36 (1976).
Fournier et al., "1alpha-hydroxycholecalciferol and 25-hydroxycholecalciferol in renal bone disease," *Calcif. Tissue Res.* Suppl. 226-35 (1975).
Fournier et al., "Advances in Nephrology from the Necker Hospital" *Adv. Nephroi Necker Hosp.* 21:237-306 (1992).
Fournier et al., "Comparison of 1α-hydroxycholecalciferol and 25-hydroxycholecalciferol in the treatment of renal osteodystrophy: Greater effect of 25-hydroxycholecalciferol on bone mineralization" Kidney International 15:196-204 (1979).
Fournier et al., "Current Status of the Management of Renal Osteodystrophy" *Proceedings of the European Dialysis and Transplant Association* 15:547-568 (1978).
Fournier et al., "Importance of Vitamin D Repletion in Uraemia," *Nephroi Dial Transplant*, 14(4):819-823 (1999).
Fournier et al., "Low doses of calcitriol or calcium carbonate for the prevention of hyperparathyroidism in predialysis patients?" *Nephrol Dial Transplant* 11(7):1493-1495 (1996).
Fournier et al., "Present-Day Concepts in the Treatment of Chronic Renal Failure" *Contrib Nephrol*. 71:64-80 (1989).
Fournier et al., "Preventing Renal Bone Disease in Moderate Renal Failure with CaCO3 and 25(OH) Vitamin D3," *Kidney Int.*, 33:S178-S279 (1988).
Fournier et al., "Renal Osteodystrophy in Dialysis Patients: Diagnosis and Treatment," *Artificial Organs*, 22:530-557 (1998).
Fournier et al., "Renal Osteodystrophy: Pathophysiology and Treatment" *Hormone Res.* 20:44-58 (1984).
Fournier et al., "The Approach to the Treatment of Secondary Hyperparathyroidism in Early Renal Failure" *Am. J. Nephrol* 8:170-172 (1988).
Fournier et al., "Traitement vitaminique D et ostéodystrophies rénales: indications et modalitiés" Nephrologie 16(2):165-190 (1995) [journal in French].

Fournier, "Vitamin D: Biochemical, Chemical, and Clinical Aspects Related to Calcium Metabolism," Vitamin D: Proceedings of the Third Workshop on Vitamin D, Asilomar, Pacific Grove, CA, USA 667-669 (1977).
Friedman et al. "The Role of Vitamin D in Mild to Moderate Chronic Kidney Disease," *Trends in Endocrinology & Metab,.* 13(5):189-194 (2002).
Frohling et al., "Serum 25-hydroxyvitamin D in patients with chronic renal failure on long-term treatment with high doses of vitamin D2." *Nephron* 26: 116-120 (1980).
Frost et al., "Histomorphometric Changes in Trabecular Bone of Renal Failure Patients Treated with Calcifediol," *Metab. Bone Dis. & Rel. Res.*, 2:285-295 (1981).
Gallagher et al., "Comparison of the Histological Effect and Metabolism of 25-(OH)D and 1,25-(OH)2D in Rat Bone," p. 399-401, IN: Norman, *Vitamin D: Basic Research and its Clinical Application: Proceedings of the Fourth Workshop on Vitamin D*, Berlin, West Germany, Feb. 1979.
Ghazali et al., "Is low plasma 25-(OH) vitamin D a major risk factor for hyperparathyroidism and Looser's zones independent of calcitriol?" *Kidney International* 55:2169-2177 (1999).
Gibson, ed., Product optimisation. *Pharmaceutical Preformulation and Formulation: A Practical Guide from Candidate Drug Selection to Commercial Dosage Form*, 295-8 (2004).
Haddad et al., "Acute Administration of 25-Hydroxycholecalciferol in Man," *J. Clin. Endocrinol. Metab.*, 42:284-289 (1976).
Haddad et al., "Human Serum Binding Capacity and Affinity for 25-Hydroxyergocalciferol and 25-Hydroxycholecalciferol," *J. Clin. Endocrinol. Metab.*, 43:86-91 (1976).
Haddad et al., "Natural and Synthetic Sources of Circulating 25-Hydroxyvitamin D in Man," *Nature*, 244:515-517 (1973).
Haddad, "Plasma Vitamin D-binding Protein (Gc-Globulin): Multiple Tasks," *J. Steroid Biochem. Molec. Biol.*, 53:579-582 (1995).
Haddad, "Seasonal Diminution of Vitamin D Stores in the United States: Can Darker Winters Lead to Lighter Bones?" *Trends Endocrinol. Metab.*, 7:209-212 (1996).
Haddad, "Traffic, Binding and Cellular Access of Vitamin D Sterols," *Bone and Mineral Res.*, Elsevier, 5:281-308 (1987).
Haddad, "Vitamin D—Solar Rays, The Milky Way, or Both?" *NEJM*, 326:1213-1215 (1992).
Haldimann et al., "Effect of an Oral Dose of 25-Hydroxyvitamin D3 on Its Blood Levels in Patients with the Nephrotic Syndrome," *J Clin Endocrinology and Metabolism*, 50(3): 470-474 (1980).
Halloran et al., "Plasma Vitamin D Metabolite Concentrations in Chronic Renal Failure: Effect of Oral Administration of 25-Hydroxyvitamin D3," *J. Clin. Endocrin. & Metab.*, 59:1063-1069 (1984).
Hamida et al., "Hyperparathyroïdie secondaire ál insuffisance rénale" Annales d'Endocrin-ologie 55:147-158 (1994) [reference in French].
Hannula et al., "Constant, But Not Pulsed Calcitriol Suppresses Hemodialysis Patients' Antigen-Induced Lymphocyte Proliferation," *Nephron*, 86:139-144 (2000).
Hari et al., "Vitamin D insufficiency and effect of cholecalciferol in children with chronic kidney disease," *Pediatr.Nephrol,.* 25: 2483-2488 (2010).
Hay et al., "Vitamin D2 in Vertebrate Evolution," *Comp. Biochem. Physiol. B*, 56:375-380 (1977).
Hodson et al., "Treatment of childhood renal osteodystrophy with calcitriol or ergocalciferol," *Clin Nephrology*, 24(4): 192-200 (1985).
Holick, "Vitamin D Deficiency in CKD: Why Should We Care?" *Am. J. Kidney Dis.*, 45:1119-1121 (2005).
Holick, "Vitamin D Status: Measurement, Interpretation and Clinical Application," *Ann Epidemiol*, 19(2):73-78 (2009).
Hollis, "Circulating 25-Hydroxyvitamin D Levels Indicative of Vitamin D Sufficiency: Implications for Establishing a New Effective Dietary Intake Recommendation for Vitamin D," *J. Nutr.* 135: 317-322 (2005).
Horst et al., "A Sensitive Competitive Protein Binding Assay for Vitamin D in Plasma," *Steroids*, 37:581-592 (1981).

(56) References Cited

OTHER PUBLICATIONS

Horst et al., "Discrimination in the Metabolism of Orally Dosed Ergocalciferol and Cholecalciferol by the Pig, Rat and Chick," *Biochem. J.*, 204:185-189 (1982).
Horst et al., "Rat cytochrome P450C24 (CYP24) does not metabolize 1,25-dihydroxyvitamin D2 to calcitroic acid," *J. Cell Biochem.*, 88:282-285 (2003).
Hottelart et al., "Ostéodystrophie rénale (2): son traitement chez l'insuffisant rénal avant la dialyse" Nephrologie 21(6):275-282 (2000) [reference in French].
Houghton et al., "The Case Against Ergocalciferol (Vitamin D2) as a Vitamin Supplement," *Am. J. Clin. Nutr.*, 84:694-697 (2006).
Hunt, et al., "A Comparison of the Toxicity of Ergocalciferol and Cholecalciferol in Rhesus Monkeys (Macaca mulatta)," J. Nutrition, 102:975-986 (1972).
Hussar, "New Drugs of 1999," *J. Am. Pharmacist. Assoc.* 40(2):181-229 (2000).
International Search Report for Application No. PCT/US2007/061521, dated Jul. 17, 2007.
International Search Report issued in connection with International Application No. PCT/US2008/061579 dated Aug. 21, 2008 (5 pages).
Ishimura et al., "Serum Levels of 1,25-Dihydroxyvitamin D, 24,25-Dihydroxyvitamin D, and 25-Hydroxyvitamin D in Nondialyzed Patients with Chronic Renal Failure," *Kidney Int.*, 55:1019-1027 (1999).
Jara et al., "Effect of Calcitriol Treatment and Withdrawal on Hyperparathyroidism in Haemodialysis Patients with Hypocalcaemia," *Nephrol. Dial. Transplant.*, 16:1009-1016 (2001).
Jean et al., "Daily Oral 25-Hydroxycholecalciferol Supplementation for Vitamin D Deficiency in Haemodialysis Patients: Effects on Mineral Metabolism and Bone Markers," *Nephrol. Dial. Transplant*, 23:3670-3676 (2008).
Jean et al., "Evidence for Persistent Vitamin D 1-Alpha-Hydroxylation in Hemodialysis Patients: Evolution of Serum 1,25-Dihydroxycholecalciferol after 6 Months of 25-Hydroxycholecalciferol Treatment" *Nephron. Clin. Pract.* 110:c58-c65 (2008).
Jean et al., "Monthly cholecalciferol administration in hemodialysis patients: a simple and efficient strategy for vitamin D supplementation" *Nephrol. Dial. Transplant* 24(12):3799-3805 (2009).
Jones, "Pharmacokinetics of vitamin D toxicity," *Am. J. Clin. Nutr.* 88(suppl): 582S-6S (2008).
Jones., "Expanding the Role for Vitamin D in Chronic Kidney Disease: Importance of Blood 25-OH-D Levels and Extra-Renal 1α-Hydroxylase in the Classical and Nonclassical Actions of 1α, 25-Dihydroxyvitamin D3," *Seminars in Dialysis*, 20(4):316-324 (2007).
K/DOQI Clinical Practice Guidelines for Bone Metabolism and Disease in Chronic Kidney Disease, National Kidney Foundation, *Am. J. Kidney Dis.*, 42 (Supplement 3):1-202 (2003).
Kajihara et al., "Novel Method to Control Release of Lipophilic Drugs with High Potency from Silicone," *Chem. Pharm. Bull.*, 51:11-14 (2003).
Kalantar-Zadeh et al., "Clinical Outcomes with Active versus Nutritional Vitamin D Compounds in Chronic Kidney Disease" *Clin J Am Soc Nephrol.* 4(9):1529-1539 (2009).
Kanis et al., "Rate of Reversal of Hypercalcaemia and Hypercalciuria Induced by Vitamin D and Its 1-alpha-Hydroxylated Derivatives," *BMJ*, 1:78-81 (1977).
Kim, *Advanced Pharmaceutics: Physicochemical Principles*, pp. 362-392, Boca Raton, Fla: CRC Press (2004).
Kleinman et al., "Effects of Calcifediol on Calcified Tissue in Uremia," *Arch Intern Med*, 138: 864-865 (1978).
Kobayashi et al., "2β-(3-Hydroxyproxy)-α,25-Dihydroxyvitamin $D_3$ (ED-71), Preventive and Therapeutic Effects on Bone Mineral Loss in Ovariectomized Rats," *Bioorganic & Medicinal Chemistry Letters*, 3(9):1815-1819 (1993).

Kooienga et al., "The effect of combined calcium and vitamin D3 supplementation on serum intact parathyroid hormone in moderate CKD," *Am.J.Kidney Dis,*. 53: 408-416 (2009).
Koshikawa, et al., "Clinical Effect of Intravenous Calcitriol Administration on Secondary Hyperparathyroidism," Nephron; 90:413-423 (2002).
LaClair et al., "Prevalence of Calcidiol Deficiency in CKD: A Cross-Sectional Study Across Latitudes in the United States," *Am. J. Kidney Dis.*, 45:1026-1033 (2005).
Lafage et al., "Ketodiet, Physiological Calcium Intake and Native Vitamin D Improve Renal Osteodystrophy," *Kidney Int.*, 42:1217-1225 (1992).
Lambert et al., "Evidence for Extrarenal Production of 1-alpha,25-Dihydroxyvitamin D in Man," *J. Clin. Invest.*, 69:722-725 (1982).
Lambrey et al., "24, 25 Dihydroxycalciferol: Assay in Non-Anephric Patients on Chronic Haemodialysis and Assessment of it's Possible Pathophysiological Role in Renal Osteodystrophy" *Proc Eur Dial Transplant Assoc.* 17:548-556 (1980).
Lambrey, "Possible Link Between Changes in Plasma 24,25-Dihydroxyvitamin D and Healing of Bone Resorption in Dialysis Osteodystrophy" *Metab. Bone Dis. & Rel. Res.* 4:25-30 (1982).
Langman et al., "25-Hydroxyvitamin D3 (Calcifediol) Therapy of Juvenile Renal Osteodystrophy: Beneficial Effect on Linear Growth Velocity," *J. Pediatrics*, 100:815-820 (1982).
Larrosa M. et al., Long-Term Treatment of Hypovitaminosis D. Calcidol or Cholecalciferol? *Annals of the Rheumatic Diseases*, vol. 64, No. Suppl. 3, Jul. 2005, p. 366.
Lau et al., "Vitamin D Therapy of Osteoporosis: Plain Vitamin D Therapy Versus Active Vitamin D Analog (D-Hormone) Therapy," *Calcif. Tissue Int.*, 65:295-306 (1999).
Lehmann et al., "Coating of Tablets and Small Particles with Acrylic Resins by Fluid Bed Technology," *Int. J. Pharm. Tech. & Prod. Mfr.*, 2:31-43 (1981).
Letteri et al., "Effects of 25-Hydroxycholecalciferol on Calcium Metabolism in Chronic Renal Failure" Adv. Exp. Med. Biol. 81:591-601 (1977).
Lips et al., "A Global Study of Vitamin D Status and Parathyroid Function in Postmenopausal Women with Osteoporosis: Baseline Data from the Multiple Outcomes of Raloxifene Evaluation Clinical Trial," *The Jour. of Clin. Endo. & Meta.*, 86(3):1212-1221 (2001).
Lomonte et al., "Are Low Plasma Levels of 25-(OH) Vitamin D a Major Risk Factor for Hyperparathyroidism Independent of Calcitriol in Renal Transplant Patients?" *J. Nephrol.*, 18:96-101 (2005).
Lund et al., "Serum 1,25-Dihydroxycholecalciferol in Anephric. Haemodialyzed and Kidney-transplanted Patients," *Nephron*, 25:30-33 (1980).
Maierhofer et al., "Synthesis and Metabolic Clearance of 1,25-Dihydroxyvitamin D as Determinants of Serum Concentrations: a Comparison of Two Methods" Journal of Clinical Endocrinology and Metabolism 53:472-475 (1981).
Manni et al., "Oral Calcitriol: Comparison Between the Same Weekly Dose Administered as a Single vs. Two Divided Pulsed Doses in Secondary Hyperparathyroidism of Chronic Renal Failure," *Ital. J Mineral Electrolyte Metab.*, 11:61-64 (1997).
Matsushita et al., "Clinical effects of 25-hydroxycholecalciferol in patients with chronic renal failure," *J Nutr Sci Vitaminol*, 23:257-261 (1977).
Mazouz et al., "Risk factors of renal failure progression two years prior to dialysisis" Clinical Nephrology 51(6):355-366 (1999).
Mazur, "Effects of 25-OHD3 on Renal Function in Pediatric Patients with Chronic Renal Failure," *Mineral Electrolyte Metab.* 10:351-358 (1984).
Memmos et al., "Response of uremic osteoid to vitamin D," *Kidney Int*, 21(Suppl. 11): S50-S54 (1982).
Menon et al., "Vitamin D insufficiency and hyperparathyroidism in children with chronic kidney disease," Pediatr Nephrol, 23:1831-1836 (2008).
Messa et al., "Direct In Vivo Assessment of Parathyroid Hormone-Calcium Relationship Curve in Renal Patients," *Kidney Int.*, 46:1713-1720 (1994).

(56) References Cited

OTHER PUBLICATIONS

Moe et al., "A randomized trial of cholecalciferol versus doxercalciferol for lowering parathyroid hormone in chronic kidney disease," *Clin.J.Am.Soc.Nephrol.* 5: 299-306 (2010).
Moe et al., "Safety and Efficacy of Pulse and Daily Calcitriol in Patients on CAPD: A Randomized Trial," *Nephrol. Dial. Transplant.*, 13:1234-1241 (1998).
Morris, "Vitamin D: A Hormone for All Seasons—How Much is Enough?" *Clin. Biochem. Rev.*, 26:21-32 (2005).
Muindi et al., "Pharmacokinetics of Liquid Calcitriol Formulation in Advanced Solid Tumor Patients: Comparison with Caplet Formulation," *Cancer Chemother. Pharmacol.*, 56:492-496 (2005).
Naik et al., "Effects of Vitamin D Metabolites and Analogues on Renal Function," *Nephron*, 28:17-25 (1981).
Nakanishi et al., "The Roles of Vitamin D in Secondary Hyperparathyroidism," [journal in Japanese] 52:1107-1112 (2004).
Oksa et al., "Effects of long-term cholecalciferol supplementation on mineral metabolism and calciotropic hormones in chronic kidney disease," *Kidney Blood Press Res.*, 31: 322-329 (2008).
Parfitt et al., "Calcitriol But No Other Metabolite of Vitamin D is Essential for NormalBone Growth and Development in the Rat," *J. Clin. Invest.*, 73:576-586 (1984).
Peacock et al., "Effect of Calcium or 25OH Vitamin D3 Dietary Supplementation on Bone Loss at the Hip in Men and Women over the Age of 60" *The Journal of Clinical Endocrinology & Metabolism*, 85(9):3011-3019 (2007).
Phadnis et al., "Direct, Rapid Effects of 25-Hydroxyvitamin D3 on Isolated Intestinal Cells," *J. Cell. Biochem.*, 90:287-293 (2003).
Pourgholami et al., "1, 25-Dihydroxyvitamin D3 Dissolved in Lipiodol Produces a Sustained Antiproliferative Effect in the Human Hepatoblastoma Cell Line HepG2," *Anticancer Res.*, 20:723-728 (2000).
Pourgholami et al., "In Vitro Antiproliferative Activity of a Medium-Chain Triglyceride Solution of 1, 25-Dihydroxyvitamin $D_3$ in HepG2 Cells," *Anticancer Res.*, 20:4257-4260 (2000).
Rapuri, P.B. et al., "Effect of Vitamins D2 and D3 Supplement Use on Serum 25-OHD Concentration in Elderly Women in Summer and Winter," Calcified Tissue International, 74(2):150-156 (2004).
Recker et al., "The Efficacy of Calcifediol in Renal Osteodystrophy," *Arch. Intern. Med.*, 138:857-863 (1978).
Reddy et al., Abstracts Sixth Annual Scientific Meeting of the American Society for Bone and Mineral Research, 36:524 (1984).
Reichel et al., "Calcium Metabolism in Early Chronic Renal Failure: Implications for the Pathogenesis of Hyperparathyroidism," *Nephrol. Dial. Transplant.*, 6:162-169 (1991).
Reichel et al., "Intermittent Versus Continuous Administration of 1,25-dihydroxyvitamin D3 in experimental renal hyperparathyroidism," *Kidney Int.*, 44:1259-1265 (1993).
Reichel, "Current treatment options in secondary renal hyperparathyroidism," *Nephrol Dial Transplant* 21:23-28 (2006).
Ritter et al., "25-Hydroxyvitamin D3 suppresses PTH synthesis and secretion by bovine parathyroid cells," *Kidney Int.*, 70:654-659 (2006).
Rucker et al., "Vitamin D insufficiency and treatment with oral vitamin D3 in northern-dwelling patients with chronic kidney disease," *J.Nephrol.* 22: 75-82 (2009).
Russell et al., "Therapeutic Effects of 25-Hydroxyvitamin D3 on Renal Osteodystrophy," *Mineral Electrolyte Metab.*, 1:129-138 (1978).
Rutherford et al., "Effect of 25-Hydroxycholecalciferol on Calcium Absorption in Chronic Renal Disease," Kidney International, 8:320-324 (1975).
Saab et al., "Prevalence of Vitamin D Deficiency and the Safety and Effectiveness of Monthly Ergocalciferol in Hemodialysis Patients," *Nephron Clin. Pract.*, 105:c132-c138 (2007).
Sanchez, "Prevention and Treatment of Renal Osteodystrophy in Children With Chronic Renal Insufficiency and End-Stage Renal Disease," *Seminars in Nephrology*, 21:441-450 (2001).
Sebert et al. "Comparative effects of equal doses of vitamin D2 and vitamin D3 for the correction of vitamin D deficiency in the elderly" in Norman et al. (eds.), Vitamin D—Gene Regulation, Structure—Function Analysis and Clinical Application: Proceedings of the Eighth Workshop on Vitamin d Paris, France, pp. 765-766, New York: Walter De Gruyter Inc. (1991).
Sebert et al., "Effets a Long Terme D'Une Association De 25-Hydroxycholécalciférol et de 1-Alpha-Hydroxycholécalciférol Sur L'Ostéodystrophie Des Hémodialysés Chroniques" Rev. Rhum Mal Osteoartic 48(7-9):535-541 (1981).
Sebert et al., "Limit by Hyperphosphatemia of the Usefulness of Vitamin D Metabolites (1 alpha-Hydroxycholecalciferol and 25-Hydroxycholecalciferol) in the Treatment of Renal Osteodystrophy," *Metab. Bone Dis. & Rel. Res.*, 2:217-222 (1980).
Sekkarie, "The Impact of Over-the-counter Vitamin D Supplementals on Vitamin D and Parathyroid Hormone Levels in Chronic Kidney Disease," *Clin. Nephrology*, 65:91-96 (2006).
Shah et al., "Prevalence and correction of 25(OH) vitamin D deficiency in peritoneal dialysis patients," *Peritoneal Dialysis Int.*, 25:362-366 ( 2005).
Sjoden, et al., "1α-Hydroxyvitamin D2 is Less Toxic than 1α-Hydroxyvitamin D3 in the Rat," Society for Experimental Biology and Medicine, 179: 432-436 (1985).
Skelly et al., In vitro and in vivo testing an correlation for oral controlled/modified-release dosage forms. *Pharm. Res.*, 7(9):975-82 (1990).
Somerville et al., "Resistance to Parathyroid Hormone in Renal Failure: Role of Vitamin D Metabolites," *Kidney Int.*, 14:245-254 (1978).
Sommerfeldt et al., "Metabolism of Orally Administered [3H]Ergocalciferol and [3H]Cholecalciferol by Dairy Calves," *J. Nutr.*, 113:2595-2600 (1983).
Stamp et al., "Comparison of Oral 25-Hydroxycholecalciferol, Vitamin D, and Ultraviolet Light as Determinants of Circulating 25-Hydroxyvitamin D," *The Lancet*, 1341-1343 (Jun. 25, 1977).
Stein et al., "An Update on the Therapeutic Potential of Vitamin D Analogues," *Expert Opin. Investig. Drugs*, 12:825-840 (2003).
Stubbs et al., "Cholecalciferol supplementation alters calcitriol-responsive monocyte proteins and decreases inflammatory cytokines in ESRD," *J.Am.Soc.Nephrol.*, 21: 353-361 (2010).
Stumpf, "The Dose Makes the Medicine," *Drug Discovery Today*, 11:550-555 (2006).
Szycher, *Szycher's Dictionary of Biomaterials and Medical Devices*, pp. 20, 48, 127, Lancaster, Penn: Technomic Publishing Co., Inc. (1992).
Sömjen et al., "Nonhypercalcemic Analogs of Vitamin D Stimulate Creatine Kinase B Activity in Osteoblast-Like ROS 17/2.8 Cells and Up-Regulate Their Responsiveness to Estrogens," *Steroids*, 63:340-343 (1998).
Taylor et al., "Interrelationship of Serum 25-Hydroxyvitamin D3 and 1,25-Dihydroxyvitamin D in Juvenile Renal Osteodystrophy after Therapy with 25-Hydroxyvitamin D3," *Metab. Bone Dis. & Rel. Res.*, 4:255-261 (1982).
Taylor et al., "The absence of 24,25-dihydroxycholecalciferol in anephric patients," *Clin.Sci.Mol.Med.Suppl.*, 55: 541-547 (1978).
Taylor, CM, 24,25-Dihydroxyvitamin D in Human Serum. In: Vitamin D. Basic Research and Clinical Applications, pp. 197-203. Walter de Gruyter, New York (1979).
Teitelbaum et al., "Calcifediol in Chronic Renal Insufficiency" *JAMA* 235(2):164-167 (1976).
Teitelbaum et al., "Tetracycline fluorescence in uremic and primary hyperparathyroid bone," *Kidney Int.*, 12:366-372 (1977).
Thomas et al., "Hypovitaminosis D in Medical Inpatients," *NEJM*, 338:777-783 (1998).
Thombre, "Assessment of the feasibility of oral controlled release in an exploratory development setting," *Drug Discovery Today*, 10(17): 1159-1166 (2005).
Tokmak et al., "High-dose cholecalciferol to correct vitamin D deficiency in haemodialysis patients," *Nephrol.Dial. Transplant.*, 23: 4016-4020 (2008).
Trakarnvanich et al., "Effect of high dose ergocalciferol in chronic kidney disease patients with 25-hydroxyvitamin D deficiency," *J.Med.Assoc.Thai.* 93: 885-891 (2010).

(56) References Cited

OTHER PUBLICATIONS

Van Weelden et al., "Apoptotic Regression of MCF-7 Xenografts in Nude Mice Treated with the Vitamin $D_3$ Analog, EB1089," *Endocrinology*, 139:2102-2110 (1998).
Verberckmoes et al., "Osteodystrophy of Dialysed Patients Treated with Vitamin D," *Proc Eur Dial Transplant Assoc.*, 10(0): 217-226 (1973).
Vieth, "What is the optimal vitamin D status for health?" *Prog. Biophys. Mol. Biol.*, 92:26-32 (2006).
Wise (ed.), *Handbook of Pharmaceutical Controlled Release Technology*, "An Overview of Controlled Release Systems," Chapter 22, pp. 431-445, 461-463; Research and Development Aspects of Oral Controlled-Release Dosage Forms, Chapter 23, pp. 465-473, New York: Marcel Dekker, Inc. 3 (2000).
Witmer et al., "Effects of 25-hydroxycholecalciferol on bone lesions of children with terminal renal failure" *Kidney International* 10:395-408 (1976).
Written Opinion for Application No. PCT/US2007/061521, dated Jul. 17, 2007.
Written Opinion for Application No. PCT/US2008/061579, dated Aug. 21, 2008.
Written Opinion for Application No. PCT/US2014/28132, dated Jun. 17, 2014.
Zerwekh et al., "Extra-Renal Production of 24,25-Dihydroxyvitamin D in Chronic Renal Failure During 25 Hydroxyvitamin D3 Therapy," *Kidney Int.*, 23:401-406 (1983).
Zisman et al., "Impact of Ergocalciferol Treatment of Vitamin D Deficiency on Serum Parathyroid Hormone Concentrations in Chronic Kidney Disease," *Am. J. Nephrol.*, 27:36-43 (2007).
Zucchelli et al., "Therapeutic effects of 25-hydroxycholecalciferol and sodium etidronate on renal osteodystrophy," *Mineral.Electrolyte Metab.* 7: 86-96 (1982).
"Modern Pharmaceutics" 4th ed., Marcel Dekker, Inc., New York, NY, p. 16-21 (2002).
Alvarez et al., "Vitamin D Supplementation in Pre-Dialysis Chronic Kidney Disease," *Dermato-Endocrinology*, 4(2):118-127 (2012).
Binkley et al., "Laboratory Reporting of 25-Hydroxyvitamin D Results: Potential for Clinical Misinterpretation," *Clinical Chemistry*, 52(11);2124-2125 (2006).
Boudville et al., "Renal Function and 25-Hydroxyvitamin D Concentrations Predict Parathyroid Hormone Levels in Renal Transplant Patients," *Nephrol Dial Transplant*, 21:2621-2624 (2006).
Brown et al., "The Vitamin D Prodrugs $1\alpha(OH)D_2$, $1\alpha(OH)D_3$ and BCI-210 Suppress PTH Secretion by Bovine Parathyroid Cells," *Nephrol Dial Transplant*, 21:644-650 (2006).
Coburn et al., "Doxercalciferol Safely Suppresses PTH Levels in Patients with Secondary Hyperparathyroidism Associated with Chronic Kidney Disease Stages 3 and 4," *Am. J. Kidney Dis.*, 43(5):877-890 (2004).
Fritsche et al., "Regulation of 25-Hydroxyvitamin $D_3$-$1\alpha$-Hydroxylase and Production of $1\alpha,25$-Dihydroxyvitamin $D_3$ by Human Dendritic Cells," *Blood*, 102(9):3314-3316 (2003).
Granja et al., "Studies on the Opening of Dioxanone and Acetal Templates and Application to the Synthesis of $1\alpha,25$-Dihydroxyvitamin $D_2^1$," *J. Org. Chem.*, 58:124-131 (1993).
Gómez-Alonso et al., "Vitamin D Status and Secondary Hyperparathyroidism: The Importance of 25-Hydroxyvitamin D Cut-Off Levels," *Kidney International*, 63(Supp. 85):S44-S48 (2003).
Prescribing information for Hectorol® (doxercalciferol capsules), Genzyme (2011).
Japanese Office Action for Application No. 2008-553520, dated Jul. 24, 2013.
Khachane et al., "Novel Sustained Release Drug Delivery System: Review," *IJPRD*, 3(12):1-14 (2012).
Kinoshita et al., "1,25-Dihydroxyvitamin D Suppresses Circulating Levels of Parathyroid Hormone in a Patient with Primary Hyperparathyroidism and Coexistent Sarcoidosis," *J. Clin. Endo. & Metabol.*, 90(12):6727-6731 (2005).

Kobayashi et al., "Variation of 25-Hydroxyvitamin D3 and 25-Hydroxyvitamin D2 Levels in Human Plasma Obtained from 758 Japanese Healthy Subjects," *J. Nutr. Sci. Vitaminol (Tokyo)*, 29(3):271-281 (1983). Abstract Only.
Martin et al., "19-Nor-1-$\alpha$-25-Dihydroxyvitamin $D_2$ (Paricalcitol) Safely and Effectively Reduces the Levels of Intact Parathyroid Hormone in Patients on Hemodialysis," *J. Am. Soc. Nephrol.*, 9:1427-1432 (1998).
Minutes of US FDA E&M Advisory Committee Meeting of Oct. 4, 1979 for Calderol® calcifediol capsules.
Morris, "Cats Discriminate Between Cholecalciferol and Ergocalciferol," *J. Anim. Physiol. a. Anim. Nutr.*, 86:229-238 (2002).
Norman et al. (eds.), *Vitamin D—Gene Regulation, Structure—Function Analysis and Clinical Application: Proceedings of the Eighth Workshop on Vitamin d* Paris, France, pp. 765-766, New York: Walter De Gruyter Inc. (1991).
Notice of allowance dated Jul. 10, 2012, in EPO application 08746908.6.
Patel et al., "Glomerular Filtration Rate is a Major Determinant of the Relationship Between 25-Hydroxyvitamin D and Parathyroid Hormone," *Calcif. Tissue Int.*, 80:221-226 (2007).
Perrie, Pharmaceutics: Drug Delivery and Targeting, Second Edition, Chapter 1 (2012).
Prescribing Information for Calderol® calcifediol capsules (1988).
Prosecution History for U.S. Appl. No. 11/549,001, filed Oct. 12, 2006.
Prosecution History for U.S. Appl. No. 13/244,945, filed Sep. 26, 2011.
Rambeck et al., "Biological Activity of $1\alpha,25$-Dihydroxyergocalciferol in Rachitic Chicks and in Rats," *IZVIAK*, 54(2/3):135-139 (1984).
Rix et al., "Effect of 18 Months of Treatment with Alfacalcidol on Bone in Patients with Mild to Moderate Chronic Renal Failure," *Nephrol Dial Transplant*, 19:870-876 (2004).
Schmidt, "Measurement of 25-Hydroxyvitamin D Revisited," *Clinical Chemistry*, 52(12):2304-2305 (2006).
Shi et al., "Preparation of Chitosan/Ethylcellulose Complex Microcapsule and its Application in Controlled Release of Vitamin $D_2$," *Biomaterials*, 23:4469-4473 (2002).
Singh et al., "C-3 Epimers Can Account for a Significant Proportion of Total Circulating 25-Hydroxyvitamin D in Infants, Complicating Accurate Measurement and interpretation of Vitamin D Status," *J. Clin. Endo. & Metabol.*, 91(8):3055-3061 (2006).
Slatopolsky et al., "Differential Effects of 19-nor-1,25-$(OH)_2D_2$ and $1\alpha$-Hydroxyvitamin $D_2$ on Calcium and Phosphorus in Normal and Uremic Rats," *Kidney International*, 62:1277-1284 (2002).
Sosa et al., "The Effect of 25-dihydroxyvitamin D on the Bone Mineral Metabolism of Elderly Women with Hip Fracture," *Rheumatology*, 39:1263-1268 (2000).
Stamp, "Intestinal Absorption of 25-hydroxycholecalciferol," *The Lancet*, 121-123 (1974).
Tuohimaa et al., "Both High and Low Levels of Blood Vitamin D are Associated with a Higher Prostate Cancer Risk: A Longitudinal, Nested Case-Control Study in the Nordic Countries," Int. J. Cancer, 108(1):104-108 (2004).
US FDA Clinical Review and Evaluation of NDA for Calderol® calcifediol capsules (believed to be available circa 1983).
US FDA Summary of Basis of Approval for Calderol® calcifediol capsules (believed to be available circa 1980).
Vieth, "Vitamin D Supplementation, 25-Hydroxyvitamin D Concentrations, and Safety," *Am. J. Clin. Nutr.*, 69:842-856 (1999).
Wootton, "Improving the Measurement of 25-Hydroxyvitamin D," *Clin Biochem Rev*, 26:33-36 (2005).
Yanoff et al., "The Prevalence of Hypovitaminosis D and Secondary Hyperparathyroidism in Obese Black Americans," *Clin. Endocrinol. (Oxf)*, 64(5):523-529 (2006).
Prescribing information for Zemplar® (paricalcitol) Capsules, Abbott (2011).

\* cited by examiner

Figure 5

| Characteristics | Placebo<br>N=29 | 30μg<br>N=12 | 60μg<br>N=16 | 90μg<br>N=14 |
|---|---|---|---|---|
| Baseline (ng/mL) | | | | |
| Mean (SD) | 16.23 (8.29) | 16.21 (7.34) | 19.79 (8.69) | 18.37 (9.77) |
| Median | 12.87 | 17.24 | 21.21 | 16.65 |
| Min, Max | 4.35, 30.43 | 5.02, 25.83 | 5.83, 32.45 | 6.67, 38.86 |
| $C_{max}$ (ng/mL)[1] | | | | |
| Mean (SD) | 3.58 (3.61) | 27.75 (8.21) | 60.33 (18.97) | 85.69 (26.90) |
| Median | 2.97 | 28.13 | 60.77 | 76.04 |
| Min, Max | -0.58, 13.83 | 10.75, 43.39 | 30.31, 89.54 | 55.44, 146.35 |
| $AUC_{0-6wk}$ (ng·d/mL) | | | | |
| Mean (SD) | 9.19 (85.66) | 689.15 (238.14) | 1477.80 (360.22) | 2060.95 (586.86) |
| Median | 22.62 | 657.19 | 1472.18 | 1896.27 |
| Min, Max | -171.75, 214.62 | 303.97, 1208.29 | 685.75, 2141.08 | 1316.39, 3206.31 |
| $t_{max}$ (d)[1] | | | | |
| Mean (SD) | 34.97 (30.79) | 37.75 (10.41) | 41.13 (5.24) | 42.50 (5.06) |
| Median | 23.00 | 42.50 | 43.00 | 43.00 |
| Min, Max | 1.00, 87.00 | 8.00, 44.00 | 29.00, 45.00 | 35.00, 56.00 |
| $t_{1/2}$ (d)[1] | | | | |
| Mean (SD) | - (-) | 25.32 (13.98) | 32.67 (8.59) | 49.62 (51.09) |
| Median | - | 24.06 | 30.85 | 36.32 |
| Min, Max | -, - | 5.16, 49.35 | 19.44, 48.11 | 23.15, 224.03 |

[1] Data are up to EOS
Abbreviations: Min: minimum; Max, maximum

| Characteristics | Placebo<br>N=29 | 30μg<br>N=12 | 60μg<br>N=16 | 90μg<br>N=14 |
|---|---|---|---|---|
| Baseline (pg/mL) | | | | |
| Mean (SD) | 23.14 (12.51) | 18.47 (7.97) | 20.96 (6.56) | 21.38 (7.70) |
| Median | 18.57 | 15.52 | 18.73 | 21.02 |
| Min, Max | 7.00, 52.07 | 5.07, 30.67 | 12.77, 33.63 | 10.70, 36.63 |
| $C_{max}$ (pg/mL)¹ | | | | |
| Mean (SD) | 9.07 (7.99) | 18.05 (20.24) | 16.58 (9.30) | 23.71 (13.63) |
| Median | 7.30 | 9.95 | 17.35 | 20.92 |
| Min, Max | -1.57, 34.13 | 3.53, 78.37 | -10.33, 29.90 | 5.50, 48.30 |
| $AUC_{0-6wk}$ (pg·d/mL) | | | | |
| Mean (SD) | -44.08 (262.50) | 252.70 (390.07) | 198.86 (295.73) | 396.03 (291.81) |
| Median | -12.17 | 165.83 | 290.33 | 393.36 |
| Min, Max | -726.25, 509.95 | -112.18, 1295.40 | -593.93, 553.00 | 72.05, 1188.60 |
| $t_{max}$ (d)¹ | | | | |
| Mean (SD) | 21.55 (16.86) | 30.67 (8.12) | 25.19 (10.81) | 26.64 (13.30) |
| Median | 23.00 | 30.00 | 22.50 | 23.00 |
| Min, Max | 1.00, 44.00 | 16.00, 42.00 | 8.00, 43.00 | 7.00, 44.00 |

¹Data are up to EOS
Abbreviations: Min: minimum; Max, maximum

| Characteristics | Placebo N=29 | 30µg N=12 | 60µg N=16 | 90µg N=14 |
|---|---|---|---|---|
| Baseline[1] (pg/mL) | | | | |
| Mean (SD) | 144.62 (67.47) | 156.28 (57.92) | 118.46 (25.89) | 155.88 (58.51) |
| Median | 130.63 | 161.22 | 113.78 | 135.08 |
| Min, Max | 64.10, 323.27 | 81.03, 253.97 | 82.23, 167.85 | 96.33, 291.25 |
| $C_{min}$ (pg/mL) | | | | |
| Mean (SD) | -38.80 (33.35) | -67.84 (36.71) | -63.09 (21.57) | -86.04 (37.39) |
| Median | -32.63 | -62.48 | -63.33 | -80.51 |
| Min, Max | -133.03, -3.90 | -140.27, -29.83 | -104.77, -24.83 | -184.10, -41.27 |
| $AUC_{0-6wk}$ (pg·d/mL) | | | | |
| Mean (SD) | 176.02 (1575.81) | -896.76 (1215.80) | -1322.53 (723.32) | -1560.91 (820.99) |
| Median | 180.95 | -1029.50 | -1325.92 | -1303.40 |
| Min, Max | -3059.00, 4463.65 | -2812.60, 1457.05 | -2228.40, -177.45 | -3743.70, -575.75 |
| $t_{min}$ (d) | | | | |
| Mean (SD) | 21.14 (14.21) | 32.08 (8.53) | 29.38 (10.39) | 32.29 (12.61) |
| Median | 21.00 | 32.50 | 32.00 | 37.00 |
| Min, Max | 1.00, 44.00 | 15.00, 42.00 | 8.00, 43.00 | 8.00, 44.00 |

[1] Baseline is the average of visits 1 (or 2 if washout), 3, and 4.

STABILIZED MODIFIED RELEASE VITAMIN D FORMULATION AND METHOD OF ADMINISTERING SAME

CROSS-REFERENCE TO RELATED APPLICATION

The benefit under 35 U.S.C. §119(e) of U.S. Provisional Patent Application Ser. No. 61/801,896 filed Mar. 15, 2013, is hereby claimed and the disclosure thereof is incorporated herein by reference.

BACKGROUND

Field of the Disclosure

The disclosure relates generally to controlled release pharmaceutical compositions. More particularly, the invention relates to controlled-release formulations for delivery of a vitamin D compound for intestinal absorption, such as a 25-hydroxyvitamin D compound, which are shelf-stable over time.

Brief Description of Related Technology

The Vitamin D metabolites known as 25-hydroxyvitamin $D_2$ and 25-hydroxyvitamin $D_3$ (collectively referred to as "25-hydroxyvitamin D") are fat-soluble steroid prohormones that contribute to the maintenance of normal levels of calcium and phosphorus in the bloodstream. The prohormone 25-hydroxyvitamin $D_2$ is produced from Vitamin $D_2$ (ergocalciferol) and 25-hydroxyvitamin $D_3$ is produced from Vitamin $D_3$ (cholecalciferol), primarily by one or more enzymes located in the liver. The two prohormones also can be produced outside of the liver from Vitamin $D_2$ and Vitamin $D_3$ (collectively referred to as "Vitamin D") in certain cells, such as enterocytes, which contain enzymes identical or similar to those found in the liver.

The 25-hydroxyvitamin D prohormones are further metabolized in the kidneys into potent Vitamin D hormones. The prohormone 25-hydroxyvitamin $D_2$ is metabolized into $1\alpha,25$-dihydroxyvitamin $D_2$; likewise, 25-hydroxyvitamin $D_3$ is metabolized into $1\alpha,25$-dihydroxyvitamin $D_3$ (calcitriol). Production of these active hormones from the 25-hydroxyvitamin D prohormones also can occur outside of the kidney in cells which contain the required enzyme(s).

Controlled release formulations of 25-hydroxyvitamin $D_2$ and/or 25-hydroxyvitamin $D_3$ can be administered to treat 25-hydroxyvitamin D insufficiency and deficiency without supraphysiological surges in intraluminal, intracellular and blood levels of 25-hydroxyvitamin D and their consequences; without causing substantially increased catabolism of the administered 25-hydroxyvitamin D; and, without causing serious side effects associated with Vitamin D supplementation, namely Vitamin D toxicity. The controlled release formulations effectively lower PTH levels without undesirable increases in serum calcium and serum phosphorus and are therefore useful for treating secondary hyperparathyroidism, for example in CKD patients. See International Patent Application Nos. PCT/US2007/061521 and PCT/US2008/061579 and U.S. patent application Ser. No. 12/109,983, incorporated herein by reference.

The controlled released compositions provide substantially increased absorption of 25-hydroxyvitamin D via transport on DBP and decreased absorption via transport in chylomicrons. The compositions also provide maintenance of substantially constant blood levels of 25-hydroxyvitamin D during a 24-hour post-dosing period. By providing a gradual, sustained and direct release of 25-hydroxyvitamin $D_2$/25-hydroxyvitamin $D_3$ and absorption preferentially to circulating DBP (rather than to chylomicrons), blood, intraluminal and intracellular 25-hydroxyvitamin D concentration spikes, i.e., supraphysiologic levels and related unwanted catabolism can be mitigated or eliminated. Furthermore, by providing a gradual and sustained release, serum levels of 25-hydroxyvitamin D can be increased and maintained more predictably than by administration of immediate release formulations, allowing for a consistent dosage and reducing or eliminating the need for frequent patient monitoring.

To deliver the benefits of controlled release formulations of 25-hydroxyvitamin D to patients, there is a need for stabilized pharmaceutical compositions that retain the desired dissolution properties of the formulation, for extended periods of time, e.g., after shipping and storage.

SUMMARY

The present invention comprises a controlled release Vitamin D formulation comprising a vitamin D compound and a cellulosic compound.

The present invention also comprises a storage-stabilized formulation for controlled release of a vitamin D compound in the gastrointestinal tract of a subject which ingests the formulation. In one aspect, the stabilized formulation comprises one or both of 25-hydroxyvitamin $D_2$ and 25-hydroxyvitamin $D_3$ and a stabilizing agent or stabilizing compound, e.g. a cellulosic compound. The stabilized formulations of the invention with the recited stabilizing agent(s) can have improved or relatively improved "storage stability", or stability following aging, as well as one or more additional characteristics including improved physical, chemical and biological properties when compared to the disclosed formulations that do not contain such agents. The claimed formulations are thus suitable as therapeutics that possess a long shelf life as well as improved bioavailability compared to aged, unstable formulations.

In one embodiment, the stabilized formulation includes one or both of 25-hydroxyvitamin $D_2$ and 25-hydroxyvitamin $D_3$, a lipophilic matrix (e.g. a wax matrix), and a stabilizing agent (e.g., a cellulosic compound). In one aspect, a stabilized formulation includes one or both of 25-hydroxyvitamin $D_2$ and 25-hydroxyvitamin $D_3$, a wax matrix, and a cellulosic stabilizing agent. In another aspect, the formulation includes one or both of 25-hydroxyvitamin $D_2$ and 25-hydroxyvitamin $D_3$, a wax matrix, and an effective amount of a cellulosic compound to maintain an advantageous degree of stabilization described herein.

In one type of embodiment, the stabilized formulation comprises a mixture of an active-loaded wax matrix comprising one or both of 25-hydroxyvitamin $D_2$ and 25-hydroxyvitamin $D_3$ and a cellulosic stabilizing agent, wherein the formulation releases an amount of 25-hydroxyvitamin D during in vitro dissolution after exposure to storage conditions of at least one month at 25° C. and 60% relative humidity that varies at all dissolution testing time points by 30% or less compared to the amount released at the same dissolution time points during in vitro dissolution conducted on fresh product.

In one type of embodiment, the formulation is an improvement formulation for controlled release of a vitamin D compound. In one aspect, the improvement comprises admixing a stabilizing agent into a formulation for controlled release of a vitamin D compound in the gastrointestinal tract of a subject which ingests the formulation. In another aspect, the improvement comprises an effective amount of a cellulosic compound admixed into a formulation for controlled release of a vitamin D compound in the gastrointestinal tract of a subject which ingests the formulation to provide an advantageous degree of stability described herein.

In one embodiment, the invention comprises a stable sustained release vitamin D formulation comprising 25-hydroxyvitamin $D_2$ or 25-hydroxyvitamin $D_3$ or combinations thereof and sustained release excipients wherein said formulation has a dissolution profile X at $T_0$ that retains this profile according to the formula $X=T_0+/-30\%$ over storage conditions selected from room temperature and ambient humidity, or 25° C. and 60% RH, or 40° C. and 75% RH, for example.

Further aspects and advantages will be apparent to those of ordinary skill in the art from a review of the following detailed description, taken in conjunction with the drawings. While the compositions and methods are susceptible of embodiments in various forms, the description hereafter includes specific embodiments with the understanding that the disclosure is illustrative, and is not intended to limit the invention to the specific embodiments described herein.

For the compositions and methods described herein, optional features, including but not limited to components, compositional ranges thereof, substituents, conditions, and steps, are contemplated to be selected from the various aspects, embodiments, and examples provided herein.

BRIEF DESCRIPTION OF THE DRAWINGS

FIG. 1 shows the dissolution profile of formulations according to the disclosure after storage for 0 to 24 months at 25° C. and 60% relative humidity. The dissolution time in hours is depicted on the x-axis and the mean percent of 25-hydroxyvitamin $D_3$ dissolved is shown on the y-axis.

FIG. 2 shows the dissolution profile of formulations according to the disclosure after storage for 0 to 6 months at 40° C. and 75% relative humidity. The dissolution time in hours is depicted on the x-axis and the mean percent of 25-hydroxyvitamin $D_3$ dissolved is shown on the y-axis.

FIG. 3 shows the dissolution profile of formulations after storage for 0 to 12 months at 25° C. and 60% relative humidity. The dissolution time in hours is depicted on the x-axis and the mean % Label Claim of 25-hydroxyvitamin $D_3$ released is shown on the y-axis.

FIG. 5 shows the resulting summary baseline-adjusted PK parameters for calcifediol concentrations by treatment group (PK population) for the patients described in Example 4 treated with a formulation according to the disclosure.

DETAILED DESCRIPTION

Figure 1A:
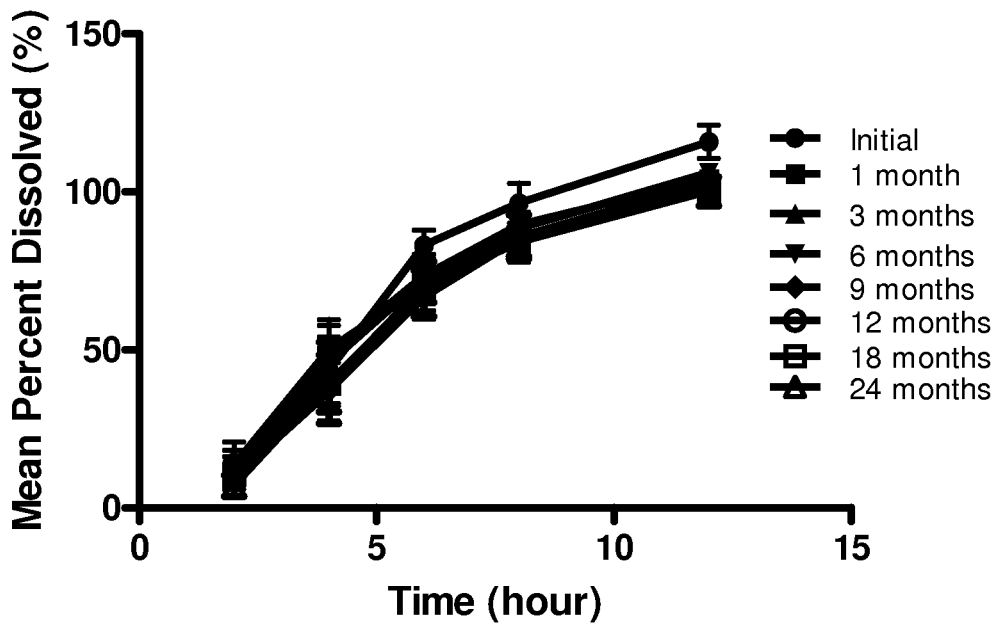
FIGS. 1A, 1B, and 1C show the dissolution profile of formulations comprising 30 μg, 60 μg, and 90 μg of 25-hydroxyvitamin $D_3$, respectively.

As used herein, the terms "controlled release," and "modified release" are used interchangeably and refer to the release of the administered vitamin D compound in a way that deviates from immediate release. As used herein, the terms "sustained release" and "extended release" are used interchangeably and refer to the release of the administered vitamin D compound over a longer period of time than a comparable immediate release formulation, resulting in serum concentrations of the vitamin D compound that remain elevated over baseline for a longer period of time than for a comparable immediate release formulation. The foregoing terms optionally include delayed release characteristics. For example, a delayed release type of controlled release formulation will be characterized by Cmax at a time greater than Cmax for an immediate release formulation. As another example, the release of a 25-hydroxyvitamin D compound will preferably be at such a rate that total serum or blood levels of 25-hydroxyvitamin D are maintained or elevated above predosing levels for an extended period of time, e.g. 4 to 24 hours or even longer.

As used herein, the term "cellulosic compound" can include cellulose $(C_6H_{10}O_5)_n$ or a derivative of cellulose, unless specified otherwise. A "cellulose ether" is a cellulose derivative that has been chemically modified to result in partial or complete etherification of the hydroxyl groups in the cellulose molecule. Examples of cellulose derivatives which can be used as stabilizing agents include, but are not limited to, celluloronic acid, carboxy methyl cellulose, ethyl cellulose, hydroxyethyl cellulose, hydroxyl propyl cellulose, hydroxyl propyl methylcellulose, methyl cellulose, polyanionic cellulose, and combinations thereof, for example. Different grades of each cellulosic compound or stabilizing agent, corresponding to variations in, e.g., molecular weight, viscosity, solubility, and hydration, are also encompassed by the terms.

Any vitamin D compound suitable for prophylactic and/or therapeutic use, and combinations thereof, are contemplated for inclusion in the formulation described herein. Vitamin D, 25-hydroxyvitamin D, 1,25-dihydroxyvitamin D, and other metabolites and analogs of Vitamin D are also useful as active compounds in pharmaceutical compositions. Specific examples include, but are not limited to, Vitamin $D_3$ (cholecalciferol), Vitamin $D_2$ (ergocalciferol), 25-hydroxyvitamin D$_3$, 25-hydroxyvitamin D$_2$, 25-hydroxyvitamin D$_4$, 25-hydroxyvitamin D$_5$, 25-hydroxyvitamin D$_7$, 1α,25-dihydroxyvitamin D$_3$, 1α,25-dihydroxyvitamin D$_2$, 1α,25-dihydroxyvitamin D$_4$, and vitamin D analogs (including all hydroxy and dihydroxy forms), including 1,25-dihydroxy-19-nor-vitamin D$_2$, and 1α-hydroxyvitamin D$_3$. In one type of embodiment, the vitamin D compound includes one or more hydroxy forms, such as a combination of 25-hydroxyvitamin D$_3$ and 25-hydroxyvitamin D$_2$.

A type of vitamin D compound particularly contemplated for use in the formulation disclosed herein can include 25-hydroxyvitamin D$_2$, 25-hydroxyvitamin D$_3$, or a combination thereof. 25-hydroxyvitamin D$_3$, is particularly contemplated. As used herein, the term 25-hydroxyvitamin D refers to one or more of 25-hydroxyvitamin D$_3$, 25-hydroxyvitamin D$_2$, 25-hydroxyvitamin D$_4$, 25-hydroxyvitamin D$_5$, or 25-hydroxyvitamin D$_7$, and it is contemplated that in any reference thereto a preferred embodiment is one or more of 25-hydroxyvitamin D$_3$ and 25-hydroxyvitamin D$_2$, preferably 25-hydroxyvitamin D$_3$. Thus, in any and all formulations described herein, it is specifically contemplated that the active can include one or both of 25-hydroxyvitamin D$_2$ and 25-hydroxyvitamin D$_3$, particularly 25-hydroxyvitamin D$_3$. In the disclosure herein, the vitamin D compound (or combination thereof) is also referred to as the "active" part of the formulation (or "active" agents), as distinguished from the controlled release matrix, the stabilizing agent, and other excipients. In the pharmacokinetic testing reported herein with samples that used 25-hydroxyvitamin D$_3$ as the active, references to 25-hydroxyvitamin D should be interpreted to mean 25-hydroxyvitamin D$_3$, and all pharmacokinetic (PK) results associated with (e.g., $t_{max}$, $C_{max}$, AUC) should be understood to be based on 25-hydroxyvitamin D$_3$.

As used herein, a "stabilized" formulation refers to a formulation exhibiting a stable in vitro dissolution profile (according to any of the parameters described further herein) and controlled release (e.g., sustained release) of a vitamin D compound in vivo, for a time following initial manufacture, e.g. following actual shelf storage or accelerated stability storage conditions. The release of the active ingredient can be measured using a suitable in vitro dissolution method, such as one of the methods already known in the art. In principle, any of the dissolution studies described in the United States Pharmacopeia, USP 29-NF 24, Dissolution <711> physical tests and determinations, United States Pharmacopeial Convention, Inc., Rockville, Md., 2006, pp. 2673-2682; European Pharmacopoeia 2.9.3 Dissolution Test for Solid Dosage Forms, or the Japanese Pharmacopoeia 6.10 Dissolution Test, can be used to determine if a formulation is stable. For purposes of the present invention, the in vitro dissolution method is United States Pharmacopeia, USP 29-NF 24, Dissolution <711> physical tests and determinations, United States Pharmacopeial Convention, Inc., Rockville, Md., 2006, pp. 2673-2682, using Apparatus 2 (paddle method), as described in the Examples below.

As used herein, $t_{max}$ (or Tmax) is defined as the time for the plasma concentration of the active compound to reach its maximum in a dose interval following administration of a formulation according to the invention. When administering a single 25-hydroxyvitamin D compound, for example 25-hydroxyvitamin D$_3$, tmax is defined as the time for the plasma concentration of serum 25-hydroxyvitamin D$_3$ to reach its maximum in a dose interval following administration of the formulation, unless specified otherwise.

Consistent with the NKF K/DOQI Guidelines, as used herein Vitamin D sufficiency is defined as serum 25-hydroxyvitamin D levels ≥30 ng/mL, Vitamin D insufficiency is defined as serum 25-hydroxyvitamin D of 16-30 ng/mL, mild Vitamin D deficiency is defined as serum 25-hydroxyvitamin D of 5-15 ng/mL, and severe Vitamin D deficiency is defined as serum 25-hydroxyvitamin D below 5 ng/mL.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

It is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc., are expressly enumerated in this specification. As another example, a stated concentration of about 20% is intended to include values from 19.5% up to 20.5%. These are only examples of what is specifically intended.

Disclosed herein are formulations for controlled release of a Vitamin D compound in the gastrointestinal tract of a subject which ingests the formulation. The formulation will include a vitamin D compound as described herein, a matrix component that releasably binds the vitamin D compound and controllably releases the vitamin D compound (e.g., a lipophilic matrix), and a stabilizer (e.g. a cellulosic compound).

A stabilized formulation according to the disclosure herein, following storage for a period of time, releases an amount of 25-hydroxyvitamin D in in vitro dissolution that does not substantially differ from the dissolution of the same formulation just after manufacturing and prior to storage. For example, in one embodiment, a formulation releases an amount of 25-hydroxyvitamin D during in vitro dissolution after exposure to storage conditions of two months at 25° C. and 60% relative humidity that varies at any given dissolution time point after four hours by 30% or less compared to the amount released at the same dissolution time point during in vitro dissolution conducted prior to exposing the formulation to the storage conditions (i.e., freshly-produced product).

The table below provides examples of advantageous degrees of storage stability contemplated for embodiments of the invention following storage at 25° C. and 60% RH, and alternatively at 40° C. and 75% RH for various times following initial manufacturing, and at various times in during dissolution testing. The degrees of storage stability are expressed in terms of the maximum deviation from nominal active potency, i.e. maximum % change from LC. Alternative embodiments of maximum deviation are also provided.

| Time (h) | 1 month | 3 mos. | 6 mos. | 9 mos. | 12 mos. | 18 mos. | 24 mos. |
|---|---|---|---|---|---|---|---|
| \multicolumn{8}{c}{storage at 25° C. and 60% RH} |
| 2 | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% |
| 4 | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% |
| 6 | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% |
| 8 | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% |
| 12 | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% |
| \multicolumn{8}{c}{storage at 40° C. and 75% RH} |
| 2 | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% |
| 4 | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% |
| 6 | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% |
| 8 | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% |
| 12 | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% | 30%, or 25%, or 20%, or 15%, or 10% |

In one type of embodiment, the formulation will have advantageous degrees of stability described in the table immediately above at multiple time points throughout the dissolution testing, e.g. at least at both 2 and 4 hour time points, optionally also at the 6 hour time point, further optionally also at the 8 hour time point, and further optionally also at the 12 hour time point, such that the dissolution profile after storage follows the dissolution profile of fresh product. Alternatively, the formulation will have advantageous degrees of stability described in the table immediately above at least at the 2, 6, and 12 hour time points. Alternatively, the formulation will have advantageous degrees of stability described in the table immediately above at least at the 4, 8, and 12 hour time points. Alternatively, the formulation will have advantageous degrees of stability described in the table immediately above at least at the 2, 4, and 6, hour time points. Alternatively, the formulation will have advantageous degrees of stability described in the table immediately above at least at the 4, 6, 8, and 12 hour time points, or at all times of 4 hours and thereafter.

In any and all of the embodiments described in the table immediately above, it is contemplated that the deviation can be positive (more release) or negative (less release) with respect to the fresh product. In one type of embodiment, it is contemplated that the deviation will be in the negative (less release) direction at multiple time points. Still further, in one type of embodiment it is contemplated that the deviation in dissolution release would have been negative (less release) at multiple time points but for the presence of the stabilizing agent in the formulation.

In any of the embodiments contemplated herein, the dissolution release profile of the formulation can have the characteristics of any one of the examples provided herein below. For example, the formulation can be characterized by a dissolution release profile providing a release of vitamin D compound of less than 30% at 2 hours, greater than 45% at 6 hours, and greater than 80% at 12 hours, and further optionally less than 60% at 6 hours.

In another type of embodiment, the formulation can be characterized by an in vitro dissolution profile providing release of vitamin D compound of less than 30% at 100 to 140 minutes, greater than 45% at 5 to 7 hours, and greater than 80% at 11 to 13 hours. In another type of embodiment, the formulation can be characterized by an in vitro dissolution profile providing release of vitamin D compound of less than 30% at 2 hours, greater than 45% at 6 hours, and greater than 80% at 12 hours. In these types of embodiments, optionally the release of vitamin D compound at 5 to 7 hours is less than 60%, or at 6 hours is less than 60%.

In another type of embodiment, the formulation can be characterized by an in vitro dissolution profile providing release of vitamin D compound of about 20% to about 40% at 2 hours, at least 35% at 6 hours, and at least 70% at 12 hours. In another type of embodiment, the formulation can be characterized by an in vitro dissolution profile providing release of vitamin D compound of about 25% to about 35% at 2 hours, at least 40% at 6 hours, and at least 75% at 12 hours. In these types of embodiments, optionally the release of vitamin D compound is 75% or less at 6 hours, or 65% or less at 6 hours, or 60% or less at 6 hours, for example.

In any of the embodiments described herein, the stabilized formulation can be characterized by a $t_{max}$ following administration of the dosage form to a human patient, of at least 4 hours, or at least 8 hours, or at least 12 hours, or at least 18 hours, or at least 20 hours, or at least 24 hours, or at least 28 hours, for example in a range of 4 to 96 hours, or in a range of 18 to 30 hours, or in a range of 13 to 28 hours, or is 28 hours, for example.

In any of the embodiments contemplated herein a formulation comprising 25-hydroxyvitamin D can be characterized by providing a baseline-adjusted $C_{max}$ per microgram of 25-hydroxyvitamin D in a range of about 0.0133 ng/mL to about 0.04 ng/mL when administered to an adult human.

In any of the methods contemplated herein, the method can include administering a stabilized sustained release dosage form comprising a 25-hydroxyvitamin D compound to a human patient, comprising administering an effective amount of the formulation to the patient to provide a baseline-adjusted $C_{max}$ of at least about 0.2 ng/mL and optionally less than 110 ng/mL, and further optionally 24 ng/mL or less, for example in a range of about 0.2 to about 24 ng/mL.

In any of the methods contemplated herein, the method can include administering a stabilized sustained release dosage form comprising a 25-hydroxyvitamin D compound to a human patient, comprising administering an effective amount of the formulation to the patient to provide a baseline-adjusted $AUC_{0-inf}$ of at least 52 ng*h/mL, and optionally less than 34,500 ng*h/mL, and further optionally about 12,000 ng*h/mL or less, for example in a range of about 52 ng*h/mL to about 12,000 ng*h/mL.

In any of the embodiments described herein, it is contemplated that the stabilized formulation, following storage, can be bioequivalent to the freshly-made product. Thus, for example, the stabilized formulation, following storage, can provide an area under the curve for the active (or serum total 25-hydroxyvitamin D), AUC (e.g., $AUC_{0-inf}$ or $AUC_{0-t}$) within a 90% confidence interval, or within 80% to 125% of the mean, or within 80% to 120% of the mean of the fresh product. In addition or in the alternative, the stabilized formulation, following storage, can provide a maximum serum concentration of the active (or serum total 25-hydroxyvitamin D), $C_{max}$ (e.g., $C_{max}$ absolute, or $C_{max}$ compared to baseline) within a 90% confidence interval, or within 80% to 125% of the mean, or within 80% to 120% of the mean, of the fresh product.

In one embodiment, a stabilized formulation comprises one or both of 25-hydroxyvitamin $D_2$ and 25-hydroxyvitamin $D_3$, a wax matrix, and a cellulosic compound. In one aspect, a stabilized formulation comprises one or both of 25-hydroxyvitamin $D_2$ and 25-hydroxyvitamin $D_3$, a wax matrix, and a cellulosic stabilizing agent. In another aspect, the formulation comprises one or both of 25-hydroxyvitamin $D_2$ and 25-hydroxyvitamin $D_3$, a wax matrix, and an effective amount of a cellulosic compound to provide an advantageous degree of stability as described herein, e.g. with respect to the table immediately above or consistent with any of the Examples described below. For example, the amount can be effective to provide a difference of 30% or less between the amount of active released during in vitro dissolution after exposure to storage conditions of at least one month at 25° C. and 60% relative humidity at a dissolution time point and the amount released at the same dissolution time point during in vitro dissolution conducted prior to exposing the formulation to the storage conditions, while a comparative formulation lacking the stabilizing agent would result in a greater difference in dissolution release following the same storage conditions.

In one aspect, the formulation is an improved formulation for controlled release of a vitamin D compound in the gastrointestinal tract of a subject which ingests the formulation. In one embodiment, the improvement comprises admixing a cellulosic stabilizing agent into a formulation for controlled release of a vitamin D compound in the gastrointestinal tract of a subject which ingests the formulation. In another embodiment, the improvement comprises an effective amount of a cellulosic compound admixed into a formulation for controlled release of a vitamin D compound in the gastrointestinal tract of a subject which ingests the formulation to provide an advantageous degree of stability as described herein, e.g. with respect to the table immediately above or consistent with any of the Examples described below. For example, the amount can be effective to provide a difference of 30% or less between the amount of active released during in vitro dissolution after exposure to storage conditions of at least one month at 25° C. and 60% relative humidity at a dissolution time point and the amount released at the same dissolution time point during in vitro dissolution conducted prior to exposing the formulation to the storage conditions, while a comparative formulation lacking the stabilizing agent would result in a greater difference in dissolution release following the same storage conditions.

The stabilizing agents can include cellulose compounds. Examples of cellulose compounds and stabilizing agents for use in the stabilized formulations of the disclosure can include, but are not limited to, celluloronic acid, carboxy methyl cellulose, ethyl cellulose, hydroxyl ethyl cellulose, hydroxyl propyl cellulose, hydroxyl propyl methyl cellulose, methylcellulose, polyanionic cellulose, and combinations thereof. Also contemplated are one or more of poloxamers (e.g., polaxamer 407), poly (ethylene oxide) polymers (e.g., Dow's POLYOX polymers), povidones, and fumed silicas (e.g., AEROSIL 200, Evonik Industries AG, Essen, Germany). The stabilizer, e.g. a cellulosic compound, preferably is present in an amount of at least about 5% of the formulation, based on the total weight of the formulation excluding any additional coatings or shells (wt %). For example, the cellulosic compound can be present in an amount of at least 5 wt % of the formulation, or at least 10 wt % of the formulation, or at least 15 wt % of the formulation, or greater than 5 wt % of the formulation, or greater than 10 wt % of the formulation, or greater than 15 wt % of the formulation. Suitable ranges include 5 wt % to 30 wt %, 10 wt % to 20 wt %, 10 wt % to 15 wt %, 5 wt % to 15 wt %, and 7.5 wt % to 12.5 wt. %. Examples include about 5 wt %, about 6 wt %, about 7 wt %, about 8 wt %, about 9 wt %, about 10 wt %, about 11 wt %, about 12 wt %, about 13 wt %, about 14 wt %, and about 15 wt %. It will be understood that the stabilizing agent referred to herein is an agent that stabilizes the dissolution release profile (and thus also the in vivo release profile) against substantial change over time during storage conditions, e.g. typical shelf storage conditions. Other agents which are known in the art as preservatives for preventing degradation of the active component itself are not intended to be encompassed within the terms "stabilizing agent" and "stabilizer" although such preservatives are also contemplated for use in the formulations of the present invention.

In one class of embodiments, the cellulosic compound is a cellulose ether. Examples of cellulose ethers include, but are not limited to, methylcellulose, hydroxyl propyl methylcellulose, hydroxyl ethyl methylcellulose, hydroxyl ethyl cellulose, hydroxyl propyl cellulose, and combinations thereof.

Hydroxyl propyl methylcellulose (HPMC) is particularly contemplated. The HPMC can be characterized by one or more of the following features, which are specifically contemplated individually and in combinations. The % methyoxyl component in the HPMC can be in a range of 19 to 24. The % hydroxypropyl component can be in a range of 7 to 12. The apparent viscosity (2% solution in water at 20° C.) can be at least 50,000 cP, or at least 80,000 cP, or in a range of about 80 to 120,000 cP, or 3000 to 120,000 cP, or 11,000 to 120,000 cP, or 80,000 to 120,000 cP. Particularly, the apparent viscosity (2% solution in water at 20° C.) can be in a range of 80,000 to 120,000 cP. The pH (1% solution in water) can be in a range of 5.5 to 8.0. For example, a suitable hydroxyl propyl methylcellulose having all of the foregoing properties, including an apparent viscosity (2% solution in water at 20° C.) in a range of 80,000 to 120,000 cP, is METHOCEL K100M CR (Dow Wolff Cellulosics, Midland, Mich.).

In one type of embodiment, the cellulosic compound will be insoluble in the matrix formulation at the melt point of the primary components of the matrix, e.g., at 65° C. or in a range of 60° C. to 75° C.

In one type of embodiment, the cellulosic compound will be hydrophilic.

The pharmaceutical formulations according to the disclosure comprising one of more of 25-hydroxyvitamin $D_2$ and 25-hydroxyvitamin $D_3$ and a cellulosic compound have unexpectedly improved stability compared to formulations lacking a cellulosic compound. In one embodiment, a stabilized formulation according to the disclosure comprises a mixture of an active-loaded lipophilic matrix comprising one or both of 25-hydroxyvitamin $D_2$ and 25-hydroxyvitamin $D_3$ and a cellulosic stabilizing agent, wherein the formulation releases an amount of 25-hydroxyvitamin D during in vitro dissolution after exposure to storage conditions of at least one month at 25° C. and 60% relative humidity that varies at any given dissolution time point by 30% or less compared to the amount released at the same dissolution time point during in vitro dissolution conducted on freshly-made product.

Formulations that are not stabilized exhibit changes in the amount of active ingredient released after the composition is stored for a period of time, as shown in the Examples below. An unstabilized formulation releases an amount of 25-hydroxyvitamin D following exposure to storage conditions that can vary at a given dissolution time point, for example by more than 30% compared to the amount released at the same dissolution time point during in vitro dissolution conducted on freshly-made product. The changes may be an increase or decrease in the dissolution rate at a given time point, and such changes produce a dissolution profile whose curve is distinct from the shape of the initial dissolution profile. An unstabilized formulation also exhibits different in vivo effects compared to a stabilized formulation according to the disclosure, following storage as described herein, e.g. following 3 months or more of storage at 25° C. and 60% RH. A stabilized formulation demonstrates different clinical pharmacokinetic parameters, such as improved bioavailability, compared to an unstabilized formulation, following storage as described herein, e.g. following 3 months or more of storage at 25° C. and 60% RH. A stabilized formulation according to the disclosure can have a base formulation which is storage unstable, combined with a stabilizing agent which renders the formulation storage stable as described herein.

The matrix that releasably binds and controllably releases the active component can be, for example, a lipophilic matrix, including a wax matrix. A wax matrix can provide a formulation which is solid or semi-solid at room temperature and solid, semi-solid, or liquid at body temperature, preferably semi-solid or liquid at body temperature. In one aspect, the wax matrix comprises a controlled release agent, an emulsifier, and an absorption enhancer.

Examples of controlled release agents suitable for use include, but are not limited to, waxes, including synthetic waxes, microcrystalline wax, paraffin wax, carnauba wax, and beeswax; polyethoxylated castor oil derivatives, hydrogenated vegetable oils, glyceryl mono-, di- or tribehenates; long-chain alcohols, such as stearyl alcohol, cetyl alcohol, and polyethylene glycol; and mixtures of any of the foregoing. Non-digestible waxy substances, such as hard paraffin wax, are preferred.

The controlled release agent can be present in an amount of at least 5 wt % of the formulation, or greater than about 5 wt % of the formulation. For example, depending on the controlled release agent used, the controlled release agent can comprise at least 5 wt % of the formulation or at least 10 wt % of the formulation, or at least 15 wt % of the formulation, or at least 20 wt % of the formulation, or at least 25 wt % of the formulation, or greater than 5 wt % of the formulation, or greater than 10 wt % of the formulation, or greater than 15 wt % of the formulation, or greater than 20 wt % of the formulation, and or greater than 25 wt % of the formulation. The controlled release agent can be present in an amount 50 wt % or less, 40 wt % or less, 35 wt % or less, or 30 wt % or less. Suitable ranges include 5 wt % to 40 wt %, 10 wt % to 30 wt % and 15 wt % to 25 wt %. Examples include about 15 wt %, about 16 wt %, about 17 wt %, about 18 wt %, about 19 wt %, about 20 wt %, about 21 wt %, about 22 wt %, about 23 wt %, about 24 wt %, and about 25 wt %.

Examples of emulsifiers suitable for use in the formulation include, but are not limited to, lipophilic agents having an HLB of less than 7, such as mixed fatty acid monoglycerides; mixed fatty acid diglycerides; mixtures of fatty acid mono- and diglycerides; lipophilic polyglycerol esters; glycerol esters including glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan esters including sorbitan monostearate, sorbitan sesquioleate; fatty acids and their soaps including stearic acid, palmitic acid, and oleic acid; and mixtures thereof glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan esters including sorbitan monostearate, sorbitan sesquioleate; fatty acids and their soaps including stearic acid, palmitic acid, and oleic acid; and mixtures thereof.

A preferred lipoidic agent is selected from glycerides and derivatives thereof. Preferred glycerides are selected from the group consisting of medium or long chain glycerides, caprylocaproyl macrogolglycerides, and mixtures thereof.

Preferred medium chain glycerides include, but are not limited to, medium chain monoglycerides, medium chain diglycerides, caprylic/capric triglyceride, glyceryl monolaurate, glyceryl monostearate, caprylic/capric glycerides, glycerylmonocaprylate, glyceryl monodicaprylate, caprylic/capric linoleic triglyceride, and caprylic/capric/succinic triglyceride.

Monoglycerides having a low melting point are preferred for making the formulation. Preferred monoglycerides include but are not limited to, glyceryl monostearate, glyceryl monopalmitate, glyceryl monooleate, glyceryl monocaprylate, glyceryl monocaprate, glyceryl monolaurate, etc., preferably glycerol monostearate (GMS). GMS is a natural emulsifying agent. It is oil soluble, but poorly soluble in water. GMS has an HLB value of 3.8. The lipophilic emulsifier can be present in an amount in a range of about 10 wt % to about 40 wt %, or about 20 wt % to about 25 wt %, for example. Other examples include about 20 wt %, about 21 wt %, about 22 wt %, about 23 wt %, about 24 wt %, and about 25 wt %.

Examples of suitable absorption enhancers include, but are not limited to, caprylocaproyl macrogolglycerides such as polyethylene glycosylated glycerides, also known as polyglycolized glycerides or PEGylated glycerides. PEGylated glycerides which may be employed in the composition include, but are not limited to, mixtures of monoglycerides, diglycerides, and triglycerides and monoesters and diesters of polyethylene glycol, polyethylene glycosylated almond glycerides, polyethylene glycosylated corn glycerides, and polyethylene glycosylated caprylic/capric triglyceride. The absorption enhancer can have an HLB value from 13 to 18, or from 13 to 15.

One preferred absorption enhancer is known under the trade name GELUCIRE (Gattefossé Corporation, Paramus, N.J., USA). GELUCIRE is a well known excipient which is a family of fatty acid esters of glycerol and PEG esters, also known as polyglycolized glycerides. GELUCIRE is used in various applications including preparing sustained release pharmaceutical compositions. GELUCIRE compounds are inert, semi-solid waxy materials which are amphiphilic and are available with varying physical characteristics such as melting point, HLB, and solubilities in various solvents. They are surface active in nature and disperse or solubilize in aqueous media forming micelles, microscopic globules or vesicles. They are identified by their melting point/HLB value. The melting point is expressed in degrees Celsius. One or a mixture of different grades of GELUCIRE excipient may be chosen to achieve the desired characteristics of melting point and/or HLB value. A preferred GELUCIRE composition is GELUCIRE 44/14, a mixture of lauroyl macrogolglycerides and lauroyl polyoxylglycerides that has a melting point of 44° C. and a HLB of 14. The absorption enhancer can be present in an amount of about 5 wt % to about 20 wt %, or about 8 wt % to about 15 wt %, for example. Other examples include about 8 wt %, about 9 wt %, about 10 wt %, about 11, wt % about 12 wt %, about 13 wt %, about 14 wt %, and about 15 wt %.

The low melting points of the wax matrix provide a means of incorporating the pharmaceutically active ingredients, e.g. the vitamin D compound such as 25-$D_2$, 25-$D_3$, or both, at temperatures from about 0° C. to about 50° C. above the melting point of the wax matrix and then filling the melt (solution and/or dispersion) in suitable capsules. The capsules can be of any variety that is compatible with the temperature of the melt fill, including soft or hard gelatin capsules, and animal or vegetable gelatin capsules. The melt solidifies inside the capsules upon cooling to room temperature.

In one aspect, a stabilized formulation may further comprise an oily vehicle for the 25-hydroxyvitamin $D_2$ and/or 25-hydroxyvitamin $D_3$. Any pharmaceutically-acceptable oil can be used. Examples include animal (e.g., fish), vegetable (e.g., soybean), and mineral oils. The oil preferably will readily dissolve the 25-hydroxyvitamin D compound used. Preferred oily vehicles include non-digestible oils, such as mineral oils, particularly liquid paraffins, and squalene. The oily vehicle can be present at a concentration in a range about 10 wt % to about 50 wt % of the formulation, or about 15 wt % to about 45 wt %, or about 20 wt % to about 40 wt %, or about 30 wt % to about 40 wt %, for example. In one type of embodiment, a suitable liquid paraffin can be characterized by one or more of the following parameters: specific gravity about 0.88 to 0.89; kinematic viscosity (40° C.) about 64 cSt to about 70 cSt; molecular weight 424; % paraffinic hydrocarbons about 59; and pour point −24° C. The ratio between the wax matrix and the oily vehicle can be optimized in order to achieve the desired rate of release of the vitamin D compound. Thus, if a heavier oil component is used, relatively less of the wax matrix can be used, and if a lighter oil component is used, then relatively more wax matrix can be used.

The stabilized controlled release compositions in accordance with the invention preferably are designed to contain concentrations of 25-hydroxyvitamin $D_2$ and/or 25-hydroxyvitamin $D_3$ of 1 to 1000 μg per unit dose, for example, and are prepared in such a manner as to effect controlled or substantially constant release of the 25-hydroxyvitamin $D_2$/25-hydroxyvitamin $D_3$, optionally into the ileum of the gastrointestinal tract, of humans or animals over an extended period of time. Example dosages include 1 μg to 1000 μg per unit dose, 1 μg to 600 μg, 1 μg to 400 μg, 1 μg to 200 μg, 1 μg to 100 μg, 5 μg to 90 μg, 30 μg to 80 μg, 20 μg to 60 μg, 30 μg to 60 μg, 35 μg to 50 μg, 5 μg to 50 μg, and 10 μg to 25 μg, for example 20 μg, 25 μg, 30 μg, 40 μg, 50 μg, 60 μg, 70 μg, 80 μg, 90 μg, and 100 μg.

In one preferred class of embodiments, the controlled release formulation releases at least 70%, more preferably at least 80% of the vitamin D compound within the first 24 hours after dosing.

Advantageously, 25-hydroxyvitamin $D_2$, 25-hydroxyvitamin $D_3$ or combinations thereof together with other therapeutic agents can be administered, e.g. orally, in accordance with the above described embodiments in dosage amounts of from 1 to 100 μg per day, for example. In one type of embodiment, the dose will be selected to provide an average rise in serum 25-hydroxyvitamin $D_3$ of about 1 to 3 ng/ml in a dose interval.

In embodiments, the formulations described herein can be administered to raise and preferably also maintain blood 1,25-dihydroxyvitamin D levels at 25 pg/mL, 30 pg/mL, or higher, e.g. 25-65 pg/mL for an extended period, for example at least one month, at least three months, at least six months, or longer.

In one aspect, the formulations described herein can be administered to patients to lower or maintain lowered serum parathyroid hormone levels, preferably an amount that lowers PTH levels by at least 30%, or alternatively the amount needed to reduce serum levels of PTH to the target range for the CKD stage (e.g., for Stage 3 is 35-70 pg/mL (equivalent to 3.85-7.7 pmol/L), for Stage 4 is 70-110 pg/mL (equivalent to 7.7-12.1 pmol/L), and for Stage 5 is 150-300 pg/mL (equivalent to 16.5-33.0 pmol/L) (defined in K/DOQI Guideline No. 1)).

In another aspect, the formulations according to the disclosure herein can be administered to a patient suffering from hyperparathyroidism secondary to chronic kidney disease (e.g., Stage 3 or 4, or Stage 3, 4 or 5) to lower the serum PTH level.

The dosages described herein are contemplated for any of the therapeutic methods described herein. It will be appreciated that the actual preferred amount of a vitamin D compound in a specific case will vary according to the particular compositions formulated, the mode of application, and the particular situs being treated. Dosages can be determined using conventional considerations, e.g., by customary comparison of the differential activity of the hormone and of a known agent, e.g. by means of an appropriate conventional pharmacological protocol.

The specific doses for each particular patient can depend on a wide variety of factors, for example, on the age, body weight, general state of health, sex, on the diet, on the timing and mode of administration, on the rate of excretion, and on medicaments used in combination and the severity of the particular disorder to which the therapy is applied.

Patients in need of vitamin D supplementation include healthy subjects and subjects at risk for vitamin D insufficiency or deficiency, for example, subjects with Stage 1, 2, 3, 4 or 5 CKD; infants, children and adults that do not drink vitamin D fortified milk (e.g. lactose intolerant subjects, subjects with milk allergy, vegetarians who do not consume milk, and breast fed infants); subjects with rickets; subjects with dark skin (e.g., in the U.S., 42% of African American women between 15 and 49 years of age were vitamin D deficient compared to 4% of white women); the elderly (who have a reduced ability to synthesize vitamin D and also are more likely to stay indoors); institutionalized adults (who are likely to stay indoors, including subjects with Alzheimer's disease or mentally ill); subjects who cover all exposed skin (such as members of certain religions or cultures); subjects who always use sunscreen (e.g., the application of sunscreen with a Sun Protection Factor (SPF) value of 8 reduces production of vitamin D by 95%, and higher SPF values may further reduce vitamin D); subjects with fat malabsorption syndromes (including but not limited to cystic fibrosis, cholestatic liver disease, other liver disease, gallbladder disease, pancreatic enzyme deficiency, Crohn's disease, inflammatory bowel disease, sprue or celiac disease, or surgical removal of part or all of the stomach and/or intestines); subjects with inflammatory bowel disease; subjects with Crohn's disease; subjects who have had small bowel resections; subjects with gum disease; subjects taking medications that increase the catabolism of vitamin D, including phenytoin, fosphenytoin, phenobarbital, carbamazepine, and rifampin; subjects taking medications that reduce absorption of vitamin D, including cholestyramine, colestipol, orlistat, mineral oil, and fat substitutes; subjects taking medications that inhibit activation of vitamin D, including ketoconazole; subjects taking medications that decrease calcium absorption, including corticosteroids; subjects with obesity (vitamin D deposited in body fat stores is less bioavailable); subjects with osteoporosis; patients who have low bone mineral density and osteoporosis; and/or postmenopausal women. According to the Institute of Medicine's report on the Dietary Reference Intakes for vitamin D, food consumption data suggest that median intakes of vitamin D for both younger and older women are below current recommendations; data suggest that more than 50% of younger and older women are not consuming recommended amounts of vitamin D.

Optionally excluded from the methods of the invention described herein are therapeutic treatment of subjects suffering from renal osteodystrophy (including osteomalacia and osteitis fibrosa cystica).

In other aspects, the compositions and methods of the invention are useful for prophylactic or therapeutic treatment of vitamin D-responsive diseases, i.e., diseases where vitamin D, 25-hydroxyvitamin D or active vitamin D (e.g., 1,25-dihydroxyvitamin D) prevents onset or progression of disease, or reduces signs or symptoms of disease. Such vitamin D-responsive diseases include cancer (e.g., breast, lung, skin, melanoma, colon, colorectal, rectal, prostate and bone cancer). 1,25-dihydroxyvitamin D has been observed to induce cell differentiation and/or inhibit cell proliferation in vitro for a number of cells. Vitamin D-responsive diseases also include autoimmune diseases, for example, type I diabetes, multiple sclerosis, rheumatoid arthritis, polymyositis, dermatomyositis, scleroderma, fibrosis, Grave's disease, Hashimoto's disease, acute or chronic transplant rejection, acute or chronic graft versus host disease, inflammatory bowel disease, Crohn's disease, systemic lupus erythematosis, Sjogren's Syndrome, eczema and psoriasis, dermatitis, including atopic dermatitis, contact dermatitis, allergic dermatitis and/or chronic dermatitis. Vitamin D-responsive diseases also include other inflammatory diseases, for example, asthma, chronic obstructive pulmonary disease, polycystic kidney disease, polycystic ovary syndrome, pancreatitis, nephritis, hepatitis, and/or infection. Vitamin D-responsive diseases have also been reported to include hypertension and cardiovascular diseases. Thus, the invention contemplates prophylactic or therapeutic treatment of subjects at risk of or suffering from cardiovascular diseases, for example, subjects with atherosclerosis, arteriosclerosis, coronary artery disease, cerebrovascular disease, peripheral vascular disease, myocardial infarction, myocardial ischemia, cerebral ischemia, stroke, congestive heart failure, cardiomyopathy, obesity or other weight disorders, lipid disorders (e.g. hyperlipidemia, dyslipidemia including associated diabetic dyslipidemia and mixed dyslipidemia hypoalphalipoproteinemia, hypertriglyceridemia, hypercholesterolemia, and low HDL (high density lipoprotein)), metabolic disorders (e.g. Metabolic Syndrome, Type II diabetes mellitus, Type I diabetes mellitus, hyperinsulinemia, impaired glucose tolerance, insulin resistance, diabetic complication including neuropathy, nephropathy, retinopathy, diabetic foot ulcer and cataracts), and/or thrombosis.

Diseases which can benefit from a modulation in the levels of vitamin D compounds, include, but are not limited to: (i) in the parathyroid—hypoparathyroidism, pseudo-hypo-parathyroidism, secondary hyperparathyroidism; (ii) in the pancreas—diabetes; (iii) in the thyroid—medullary carcinoma; (iv) in the skin—psoriasis; wound healing; (v) in the lung—sarcoidosis and tuberculosis; (vi) in the kidney—chronic kidney disease, hypophosphatemic VDRR, vitamin D dependent rickets; (vii) in the bone—anticonvulsant treatment, fibrogenisis imperfecta ossium, osteitis fibrosa cystica, osteomalacia, osteoporosis, osteopenia, osteosclerosis, renal osteodytrophy, rickets; (viii) in the intestine—glucocorticoid antagonism, idopathic hypercalcemia, malabsorption syndrome, steatorrhea, tropical sprue; and (ix) autoimmune disorders.

In embodiments of the invention, the disease that benefits from a modulation in the levels of vitamin D compounds are selected from cancer, dermatological disorders (for example, psoriasis), parathyroid disorders (for example, hyperparathyroidism and secondary hyperparathyroidism), bone disorders (for example, osteoporosis) and autoimmune disorders.

The formulation can be prepared by procedures well within the capabilities of the ordinary skilled artisan. For example, the components of the matrix (e.g. wax and oily vehicle) can be melted, if necessary, to provide a flowable liquid thereby making it easier to obtain a homogeneous mixture. The active (e.g., 25-hydroxyvitamin $D_2$ and/or 25-hydroxyvitamin $D_3$) is added to the liquid carrier, for example dissolved in an alcohol such as anhydrous ethanol, and the ingredients are mixed to provide a homogeneous mixture. In one type of embodiment, the stabilizer can be added after all matrix components (e.g., waxes and oils) are blended and prior to combination with the active. The mixture can be cooled and stored prior to later division into unit dosage forms, such as filled gelatin capsules.

In one type of method, a portion of the oily vehicle, controlled release agent, and emulsifier are heated to a relatively high temperature (e.g., 65° C.) and mixed prior to adding an absorption enhancer, followed by additional mixing until homogenous, then cooling to an intermediate elevated temperature (e.g., 50° C. to 55° C.). In a separate vessel, an antioxidant preservative and the remainder of the oily vehicle are mixed and heated to an intermediate elevated temperature (e.g., 50° C.), then combined and mixed with the wax mixture until a homogenous solution is obtained. Next, the stabilizer is added, with mixing. Next, a solution of the vitamin D compound(s) in alcohol is combined with the homogenous waxy solution, mixed until a homogenous solution is obtained, preferably filled into capsules, and then cooled to room temperature. In another preferred method, a portion of the oily vehicle, controlled release agent, and emulsifier are heated at a temperature of 55° C. to 60° C. and mixed prior to adding an absorption enhancer, followed by additional mixing until homogenous. In a separate vessel, an antioxidant preservative, the remainder of the oily vehicle, and the stabilizer are mixed and heated to a temperature of 55° C. to 60° C., then combined and mixed with the wax mixture until a homogenous solution is obtained. Next, a solution of vitamin D compound in alcohol is combined with the homogenous waxy solution, mixed until a homogenous solution is obtained, preferably filled into capsules, and then cooled to room temperature.

The formulation preferably is placed in capsules prior to administration to the patient in need of treatment. Such capsules may be hard or soft, and soft capsules are particularly contemplated. The formulation may be filled into gelatin capsules using standard capsule filling machinery, such as by melting the formulation and injection-filling it into soft capsule shells. Example soft capsule shells include VEGICAPS and OPTISHELL technologies (Catalent, Somerset, N.J., USA). In the alternative, the formulation can be made into a unit dosage form by any other suitable processes, for example to yield tablets, sachets, dragees, suppositories, or the like.

In one type of embodiment, the formulation is prepared for and administered by oral delivery. In another type of embodiment, the formulation is prepared for and administered as a suppository, e.g. a rectal suppository.

The formulation and methods of use and making are contemplated to include embodiments including any combination of one or more of the additional optional elements, features, and steps further described below, unless stated otherwise.

Thus, in one type of embodiment, the formulation further includes a preservative, such as an antioxidant. Butylated hydroxytoluene (BHT) is preferred.

In another type of embodiment, the vitamin D compound is administered in combination with one or more other therapeutic agents.

If the vitamin D compound is administered in combination with one or more other therapeutic agents, the proportions of each of the compounds in the combination being administered will be dependent on the particular disease state being addressed. For example, one may choose to administer 25-hydroxyvitamin $D_2$ and/or 25-hydroxyvitamin $D_3$ (e.g., orally) with one or more calcium salts (intended as a calcium supplement or dietary phosphate binder), bisphosphonates, calcimimetics, nicotinic acid, iron, phosphate binders, cholecalciferol, ergocalciferol, active Vitamin D sterols, glycemic and hypertension control agents, various antineoplastic agents and inhibitors of CYP24 and other cytochrome P450 enzymes that can degrade vitamin D agents. In addition, one may choose to intravenously administer 25-hydroxyvitamin $D_2$ and/or 25-hydroxyvitamin $D_3$ with cholecalciferol, ergocalciferol, active Vitamin D sterols, glycemic and hypertension control agents, various antineoplastic agents and inhibitors of CYP24 and other cytochrome P450 enzymes that can degrade vitamin D agents. In practice, higher doses of the compounds of the present invention are used where therapeutic treatment of a disease state is the desired end, while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art.

As described above, the formulation is preferably filled into gelatin capsules, but it may also be administered in neat form, or with one or more external coating layers, such as an enteric coating. It is also contemplated that the formulation can be pressed into tablets, and in such cases one or more tablet pressing excipients may be included.

In the compositions and methods described herein, preferred steps, preferred components, preferred compositional ranges thereof, and preferred combinations of the foregoing, can be selected from the various specific examples provided herein. For example, a preferred formulation includes 25-hydroxyvitamin D (e.g., about 30 μg, about 60 μg, or about 90 μg 25-hydroxyvitamin $D_3$), about 2 wt % (e.g., 2.32 wt %)

anhydrous ethanol, about 10 wt % (e.g., 9.75 wt %) GELUCIRE 44/14, about 20 wt % (e.g., 20.00 wt. %) hard paraffin, about 23 wt % (e.g., 22.55 wt %) GMS, about 35 wt % (e.g., 35.36 wt %) liquid paraffin or mineral oil, about 10 wt % HPMC, and optionally a small amount of preservative (e.g., 0.02 wt % BHT). A variation on this formulation will include about 15% (e.g., 15.29 wt %) HPMC and about 30 wt % (e.g., 29.88 wt %) liquid paraffin or mineral oil.

EXAMPLES

The following Examples illustrate specific formulations and methods for their preparation. The Examples are provided for illustration and are not intended to limit the scope of the invention.

In vitro dissolution testing in the Examples was performed using USP Apparatus 2 (paddle method) as described in USP 29-NF 24, general chapter <711> Dissolution, using the Dissolution Medium described below. In general, the method proceeds according to the following steps. Place the stated volume of the Dissolution Medium (±1%) in the vessel of the specified apparatus, assemble the apparatus, equilibrate the Dissolution Medium to 37±0.5°, and remove the thermometer. Place the dosage units in the apparatus, taking care to exclude air bubbles from the surface of the dosage units, and immediately operate the apparatus at the specified rate. At each of the times stated, withdraw specimens from a zone midway between the surface of the Dissolution Medium and the top of the rotating blade, not less than 1 cm from the vessel wall. Replace the aliquots withdrawn for analysis with equal volumes of fresh Dissolution Medium at 37° or. Keep the vessel covered for the duration of the test, and verify the temperature of the mixture under test at suitable times. Perform the analysis using a suitable assay method, ultra performance liquid chromatography (UPLC) in this case.

Six capsules of each formulation were tested per time point. The Dissolution Medium was 0.05 M pH 6.8 phosphate buffer/1% sodium dodecyl sulfate dissolution medium at 37±0.5° C., and the apparatus was operated at 100 rotations per minute. Samples were taken at 2, 4, 6, 8, and 12 hours and the 25-hydroxyvitamin D content of each sample was determined using UPLC.

Example 1—In Vitro Dissolution of Unstabilized Sustained Release Formulations of 25-Hydroxyvitamin D The dissolution of a formulation made from a mixture of 90 μg of 25-hydroxyvitamin $D_3$, 19.98 wt % hard paraffin, 37.85 wt % GMS, 9.76 wt % GELUCIRE 44/14, 2.36 wt % anhydrous ethanol, 29.88 wt % liquid paraffin, and 0.02 wt % BHT (Comparative Formulation 1) was tested. The formulation did not comprise a cellulosic compound. The mean amount of 25-hydroxyvitamin $D_3$ released, calculated as a mean percentage of the nominal drug loading per dosage form (mean % of label claim, % LC) at T=0 and after controlled storage of the formulation at 5° C. and ambient humidity for up to 12 months are summarized in the table below. It was determined that the samples were stored for a period of about 3 months at a temperature in a range of 15° C. to 30° C. and ambient humidity, prior to testing. Thus, the sample which should have represented time zero is labeled as T=$0_p$ (pseudo time zero), and it should be understood that the nominal 1 month, 3 month, 6 month, 9 month, and 12 month aged samples also experienced the approximately 3-month aging period just described. To provide a more accurate baseline, a fresh batch of the same type of samples was prepared and tested without any aging; this data is labeled as T=$0_f$ to indicate fresh samples. The coefficient of variation (% CV) is also reported. The percent change from the initial amount of 25-hydroxyvitamin $D_3$ released by T=$0_p$ and T=$0_f$ lots is provided in brackets and double brackets, respectively.

| | | | Dissolution Following Storage at 5° C./Ambient Humidity | | | | |
|---|---|---|---|---|---|---|---|
| Time (hours) | T = $0_p$ pseudo | T = $0_f$ fresh | 1 Month (% CV) [% change from T = $0_p$] [[% change from T = $0_f$]] | 3 Months (% CV) [% change from T = $0_p$] [[% change from T = $0_f$]] | 6 months (% CV) [% change from T = $0_p$] [[% change from T = $0_f$]] | 9 months (% CV) [% change from T = $0_p$] [[% change from T = $0_f$]] | 12 months (% CV) [% change from T = $0_p$] [[% change from T = $0_f$]] |
| 2 | 6.1 (29.6) | 22.1 (17.2) | 8.9 (13.4) [45.9] [[59.7]] | 15.7 (27.4) [157.4] [[29.0]] | 9.1 (23) [49.2] [[58.8]] | 15.2 (47.2) [149.2] [[31.2]] | 12.7 (16.8) [108.2] [[42.5]] |
| 4 | 14.5 (15.7) | 52.0 (4.6) | 20.7 (19.1) [42.8] [[60.2]] | 22.3 (15.6) [53.8] [[57.1]] | 22.9 (7.1) [57.9] [[56.0]] | 25.2 (19.2) [73.8] [[51.5]] | 24.7 (13.5) [70.3] [[52.5]] |
| 6 | 27.6 (21.2) | 77.9 (4.6) | 35.7 (9.6) [29.3] [[54.2]] | 33.5 (2.6) [21.4] [[57.0]] | 34.1 (7.1) [23.6] [[56.2]] | 36.2 (20.5) [31.2] [[53.5]] | 34.8 (14.6) [26.1] [[55.3]] |
| 8 | 45.7 (23.6) | 96.8 (2.9) | 53.0 (9.9) [16.0] [[45.2]] | 47.4 (3.7) [3.7] [[51.0]] | 46.8 (6) [2.4] [[51.7]] | 47.8 (18.6) [4.6] [[50.6]] | 46.4 (8.9) [1.5] [[52.1]] |
| 12 | 89.7 (15.6) | 112.3 (1.6) | 100.0 (4.8) [11.5] [[11.0]] | 78.9 (8.1) [12.0] [[29.7]] | 76.9 (5.7) [14.3] [[31.5]] | 74.1 (17.3) [17.4] [[34.0]] | 78.8 (5.3) [12.2] [[29.8]] |

The dissolution of Comparative Formulation 1 after storage at 25° C. and 60% relative humidity for 0 to 12 months was tested. The results are summarized in the table below.

Dissolution Following Storage at 25° C./60% Relative Humidity

| Dissolution Time (hours) | T = 0$_p$ pseudo | T = 0$_f$ fresh | 1 Month (% CV) [% change from T = 0$_p$] [[% change from T = 0$_f$]] | 3 Months (% CV) [% change from T = 0$_p$] [[% change from T = 0$_f$]] | 6 months (% CV) [% change from T = 0$_p$] [[% change from T = 0$_f$]] | 9 months (% CV) [% change from T = 0$_p$] [[% change from T = 0$_f$]] | 12 months (% CV) [% change from T = 0$_p$] [[% change from T = 0$_f$]] |
|---|---|---|---|---|---|---|---|
| 2 | 6.1 (29.6) | 22.1 (17.2) | 7.6 (7.7) [24.6] [[65.6]] | 10.8 (15.7) [77.0] [[51.1]] | 8.5 (19.2) [39.3] [[61.5]] | 10.8 (15.8) [77.0] [[51.1]] | 13.5 (24.7) [121.3] [[38.9]] |
| 4 | 14.5 (15.7) | 52.0 (4.6) | 18.7 (18.6) [29.0] [[64.0]] | 22.8 (23.7) [57.2] [[56.2]] | 17.9 (11.9) [23.4] [[65.6]] | 21.4 (5.5) [47.6] [[58.8]] | 24.5 (17.4) [69.0] [[52.9]] |
| 6 | 27.6 (21.2) | 77.9 (4.6) | 27.1 (22.7) [1.8] [[65.2]] | 30.7 (29.6) [11.2] [[60.6]] | 23.8 (11.6) [13.8] [[69.4]] | 27.0 (7.3) [2.2] [[65.3]] | 30.0 (15.7) [8.7] [[61.5]] |
| 8 | 45.7 (23.6) | 96.8 (2.9) | 37.1 (18.1) [18/8] [[61.7]] | 40.6 (29.9) [11.2] [[58.1]] | 28.5 (13.2) [37.6] [[70.6]] | 32.3 (6.4) [29.3] [[66.6]] | 35.6 (14.7) [22.1] [[63.2]] |
| 12 | 89.7 (15.6) | 112.3 (1.6) | 61.6 (16.6) [31.3] [[45.1]] | 53.0 (32.2) [40.9] [[52.8]] | 38.5 (12.2) [57.1] [[65.7]] | 38.9 (6) [56.6] [[65.4]] | 44.2 (12.2) [50.7] [[60.6]] |

The dissolution of Comparative Formulation 1 after storage at 40° C. and 75% relative humidity for 0, 1, 3, and 6 months was tested. The results are summarized in the table below.

Dissolution Following Storage at 40° C./75% Relative Humidity

| Dissolution Time (hours) | T = 0$_p$ pseudo | T = 0$_f$ fresh | 1 Month (% CV) [% change from T = 0$_p$] [[% change from T = 0$_f$]] | 3 Months (% CV) [% change from T = 0$_p$] [[% change from T = 0$_f$]] | 6 Months (% CV) [% change from T = 0$_p$] [[% change from T = 0$_f$]] |
|---|---|---|---|---|---|
| 2 | 6.1 (29.6) | 22.1 (17.2) | 11.7 (50) [91.8] [[47.1]] | 16.9 (36.3) [177.0] [[23.5]] | 1.8 (75) [70.5] [[91.9]] |
| 4 | 14.5 (15.7) | 52.0 (4.6) | 52.0 (45.1) [258.6] [[0]] | 59.8 (31.3) [312.4] [[15.0]] | 36.2 (21.8) [149.7] [[30.4]] |
| 6 | 27.6 (21.2) | 77.9 (4.6) | 87.0 (21.5) [215.2] [[11.7]] | 97.8 (24) [254.3] [[25.5]] | 76.7 (12.3) [177.9] [[1.5]] |
| 8 | 45.7 (23.6) | 96.8 (2.9) | 107.3 (8.1) [134.8] [[10.8]] | 110.9 (13) [142.7] [[14.6]] | 101.2 (6.1) [121.4] [[4.5]] |
| 12 | 89.7 (15.6) | 112.3 (1.6) | 118.7 (1.7) [32.3] [[5.7]] | 115.1 (3.7) [28.3] [[2.5]] | 112.6 (2.1) [25.5] [[0.3]] |

Without intending to be bound by any particular theory, the increase in the extent of dissolution following storage at 40° C. compared to the pseudo T=0 values is believed to be due to a combination of the aging effect described above on the pseudo T=0 samples tested, and a temperature-dependent phase change in the formulation when stored at 40° C.

Aged product according to Comparative Formulation 1 was heat cured and then subject to dissolution testing. Curing consists of applying a heat treatment and has been shown to stabilize pharmaceutical formulations (see, e.g., U.S. Pat. No. 6,645,527). Comparative Formulation 1 (aged samples) was heated at 40° C. for 72 hours for curing, and then was stored at room temperature for 8 weeks. Release of 25-hydroxyvitamin $D_3$ from the cured formulation was tested after storage for 0, 2, 4, and 8 weeks at room temperature. The results are summarized in the table below.

Dissolution Following Curing at 40° C. for 72 Hours

| Dissolution Time (hours) | T = 0 | 2 weeks % LC [% change] | 4 weeks % LC [% change] | 8 weeks % LC [% change] |
|---|---|---|---|---|
| 2 | 17.4 | 12.4 [28.7] | 11.4 [34.5] | 8.2 [52.9] |
| 4 | 53.3 | 46.4 [12.9] | 40.1 [24.8] | 26.6 [50.1] |
| 6 | 86.2 | 76.2 [11.6] | 69.0 [20.0] | 44.8 [48.0] |
| 8 | 103.8 | 102.0 [1.7] | 95.8 [7.7] | 66.6 [35.8] |
| 12 | 115.7 | 110.5 [4.5] | 119.8 [3.5] | 103.3 [10.7] |

Example 2—In Vitro Dissolution of Stabilized Controlled Release Formulations of 25-Hydroxyvitamin D The dissolution of a sustained release formulation comprising 90 µg of 25-hydroxyvitamin $D_3$, 19.88 wt % hard paraffin, 15.29 wt % hydroxypropyl methylcellulose, 22.55 wt % GMS, 9.76 wt % GELUCIRE 44/14, 2.36 wt % anhydrous ethanol, 29.88 wt % liquid paraffin, and 0.02 wt % BHT (Example Formulation A) was tested after 0 to 11 weeks of storage at room temperature. The results are summarized in the table below.

| Dissolution Following Storage at Room Temperature/Ambient Humidity | | | |
|---|---|---|---|
| Dissolution Time (hours) | T = 0 | 3 weeks % LC [% change] | 11 weeks % LC [% change] |
| 2 | 15.45 | 14.20 [8.1%] | 12.08 [21.8%] |
| 4 | 36.3 | 38.80 [6.9%] | 37.13 [2.3%] |
| 6 | 56.9 | 62.70 [10.2%] | 59.51 [4.6%] |
| 8 | 71.1 | 71.90 [1.1%] | 69.76 [1.9%] |
| 12 | 89.4 | 91.20 [2.0%] | 89.90 [0.6%] |

The dissolution of a sustained release formulation comprising 90 µg of 25-hydroxyvitamin $D_3$, 19.88 wt % hard paraffin, 10.00 wt % hydroxyl propyl methylcellulose, 22.55 wt % GMS, 9.76 wt % GELUCIRE 44/14, 2.36 wt % anhydrous ethanol, 35.17 wt % liquid paraffin, and 0.02 wt % BHT (Example Formulation B) was tested after 0 to 26 weeks of storage at room temperature. The results are summarized in the table below.

| Dissolution Following Storage at Room Temperature/Ambient Humidity | | | |
|---|---|---|---|
| Dissolution Time (hours) | T = 0 | 6 weeks % LC [% change] | 13 weeks % LC [% change] | 26 weeks % LC [% change] |
| 2 | 30.15 | 25.40 [15.8%] | 25.20 [16.4%] | 21.10 [30.0%] |
| 4 | 58.55 | 51.90 [11.4%] | 51.80 [11.5%] | 45.20 [22.8%] |
| 6 | 72.1 | 74.40 [3.2%] | 73.00 [1.2%] | 67.63 [6.2%] |
| 8 | 80.55 | 84.30 [4.7%] | 84.50 [4.9%] | 77.30 [4.0%] |

-continued

| Dissolution Following Storage at Room Temperature/Ambient Humidity | | | |
|---|---|---|---|
| Dissolution Time (hours) | T = 0 | 6 weeks % LC [% change] | 13 weeks % LC [% change] | 26 weeks % LC [% change] |
| 12 | 91.8 | 94.10 [2.5%] | 94.40 [2.8%] | 91.16 [0.7%] |

Example Formulation B demonstrated a substantially stable dissolution profile following storage for at least 26 weeks at room temperature.

The stability of stabilized formulations comprising 30 µg (Example Formulation C), 60 µg (Example Formulation D), or 90 µg (Example Formulation E) of 25-hydroxyvitamin $D_3$ was tested using storage conditions of 25° C. and 60% relative humidity and 40° C. and 75% relative humidity. The compositions of Example Formulations C to E are summarized in the table below:

| Component | Amount |
|---|---|
| 25-hydroxyvitamin $D_3$ | 30 µg, 60 µg, or 90 µg |
| Paraffin Wax | 20.00 wt % |
| Mineral Oil | 35.36 wt % |
| Hydroxy propyl Methylcellulose K100M CR (METHOCEL) | 10.00 wt % |
| Glycerol monostearate | 22.55 wt % |
| Lauroyl macrogolglycerides and polyoxylglycerides (GELUCIRE 44/14) | 9.75 wt % |
| Anhydrous Alcohol | 2.32 wt % |
| BHT | 0.02 wt % |
| Soft Capsule Shell (VEGICAPS) | |

Figure 1B:
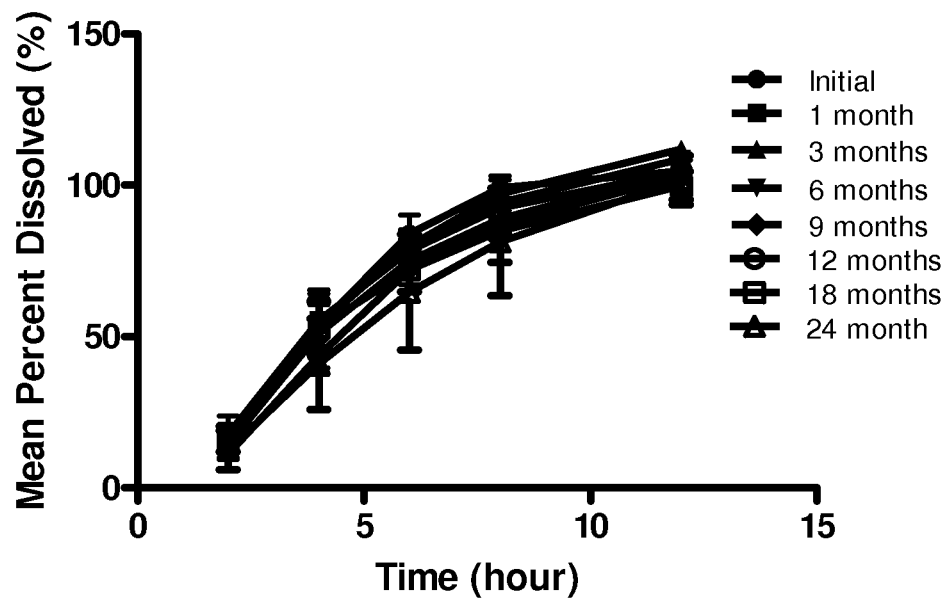
Figure 1C:
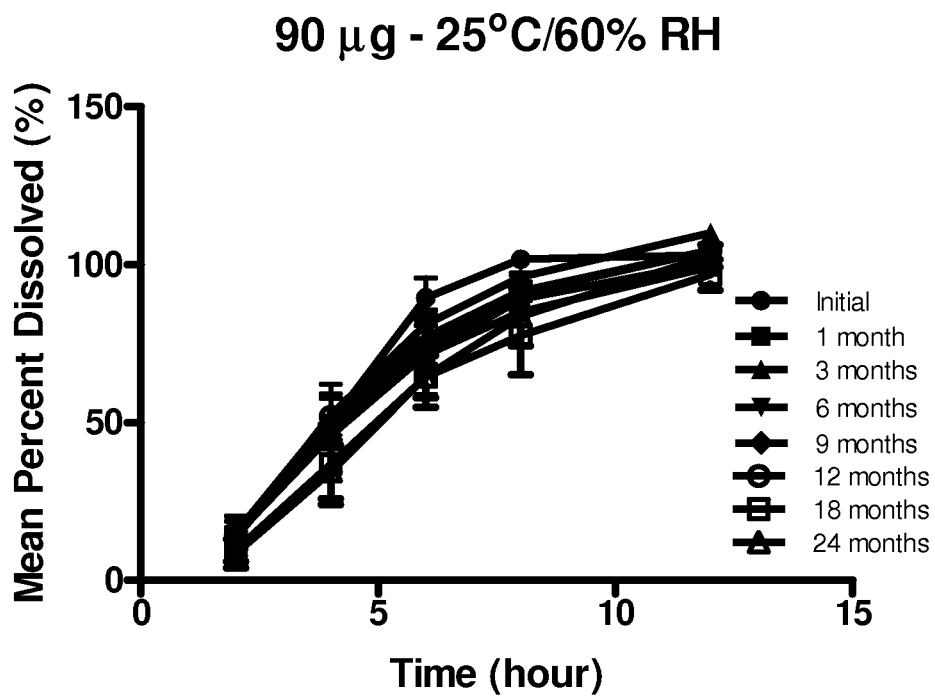

The formulations exhibited substantially stable dissolution profiles following storage at 25° C. and 60% relative humidity for at least 24 months (FIG. 1). The dissolution results (% LC and % CV) are summarized in the table below.

| Dissolution Following Storage at 25° C./60% Relative Humidity | | | | | | | | |
|---|---|---|---|---|---|---|---|---|
| Time (hours) | T = 0 % LC (% CV) | 1 month % LC (% CV) | 3 mos. % LC (% CV) | 6 mos. % LC (% CV) | 9 mos. % LC (% CV) | 12 mos. % LC (% CV) | 18 mos. % LC (% CV) | 24 mos. % LC (% CV) |
| 30 µg 25-hydroxyvitamin $D_3$ (Example Formulation C) | | | | | | | | |
| 2 | 10.1 (16.1) | 12.9 (25.2) | 14.0 (48.5) | 9.6 (38.3) | 10.5 (18.2) | 13.5 (35.8) | 10.6 (26.5) | 7.0 (47.8) |
| 4 | 43.6 (12.7) | 48.8 (10.9) | 45.9 (29.9) | 36.8 (25) | 37.2 (11.1) | 50.2 (14.8) | 39.3 (22.9) | 39.6 (32.3) |
| 6 | 83.1 (5.7) | 73.4 (9.2) | 72.4 (7.5) | 71.4 (6.8) | 66.7 (10.6) | 70.6 (11.5) | 70.1 (7.2) | 69.3 (12.6) |
| 8 | 96.4 (6.5) | 89.6 (4.4) | 88.4 (4.7) | 88.4 (5.7) | 85.2 (4.9) | 85.4 (9) | 84 (5.1) | 85.7 (8.2) |
| 12 | 115.8 (4.5) | 104.2 (1.9) | 105.6 (1.4) | 106.1 (1.6) | 101.5 (1.5) | 100.8 (3.9) | 100.2 (4.5) | 103 (2.6) |
| 60 µg 25-hydroxyvitamin $D_3$ (Example Formulation D) | | | | | | | | |
| 2 | 17.5 (20) | 16.3 (27.4) | 16.1 (25.3) | 17.7 (34.7) | 11.2 (20.2) | 14.3 (29.1) | 16.1 (25.8) | 12.4 (52.3) |
| 4 | 53.6 (19.6) | 55.1 (18.8) | 53.8 (12.8) | 55.3 (17.9) | 43.7 (14) | 51 (22.5) | 52.9 (16.7) | 41 (36.6) |
| 6 | 83.9 (7.5) | 78.7 (8.3) | 79.9 (6.6) | 78.4 (4.7) | 72.2 (7.1) | 75 (13) | 72 (9.9) | 64.7 (29.6) |
| 8 | 99.2 (3.9) | 94.3 (5.2) | 97.2 (4.8) | 92.5 (3.3) | 87 (5.5) | 88.9 (6.3) | 84.9 (12.3)* | 81.3 (21.7) |
| 12 | 104.8 (3.3) | 108.7 (1.8) | 111.9 (1.1) | 104.5 (0.5) | 103.1 (0.8) | 104.7 (1.4) | 99.8 (4.6)* | 101.7 (8) |

Dissolution Following Storage at 25° C./60% Relative Humidity

| Time (hours) | T = 0 % LC (% CV) | 1 month % LC (% CV) | 3 mos. % LC (% CV) | 6 mos. % LC (% CV) | 9 mos. % LC (% CV) | 12 mos. % LC (% CV) | 18 mos. % LC (% CV) | 24 mos. % LC (% CV) |
|---|---|---|---|---|---|---|---|---|
| 90 µg 25-hydroxyvitamin $D_3$ (Example Formulation E) | | | | | | | | |
| 2 | 14.9 (19.9) | 14.9 (8.6) | 13.3 (41.2) | 13.5 (23.4) | 14.3 (30.4) | 15 (35.1) | 9.5 (37.1) | 8.5 (53.2) |
| 4 | 49.9 (16.4) | 46.9 (10.2) | 52.4 (18.5) | 49.7 (16.4) | 45.9 (25.6) | 51.8 (14) | 36.8 (34.5) | 34.4 (24.9) |
| 6 | 89.4 (7.2) | 71.4 (4.1) | 81.1 (5.6) | 74.2 (11.1) | 71.6 (17.6) | 77 (4.9) | 64.4 (10.3) | 64.5 (15.1) |
| 8 | 101.7 (2.5) | 84.9 (2.8) | 96.1 (2.3) | 90.8 (6.4) | 89 (9.4) | 91.6 (3.3) | 77.4 (15.7) | 83.6 (11.2) |
| 12 | 103 (2.1) | 99.3 (2.4) | 110 (1.3) | 104.4 (1.1) | 100.5 (2.4) | 104.6 (0.3) | 96.8 (5) | 102.8 (3.4) |

*4 replicates instead of 6

The percent change between the amount of 25-hydroxyvitamin $D_3$ released following aging compared to the initial amount released is summarized in the table below.

| Time (h) | 1 month % change | 3 mos. % change | 6 mos. % change | 9 mos. % change | 12 mos. % change | 18 mos. % change | 24 mos. % change |
|---|---|---|---|---|---|---|---|
| 30 µg 25-hydroxyvitamin $D_3$ (Example Formulation C) | | | | | | | |
| 2 | 27.7% | 38.6% | 5.0% | 4.0% | 33.7% | 5.0% | 30.7% |
| 4 | 11.9% | 5.3% | 15.6% | 14.7% | 15.1% | 9.9% | 9.2% |
| 6 | 11.7% | 12.9% | 14.1% | 19.7% | 15.0% | 15.6% | 16.6% |
| 8 | 7.1% | 8.3% | 8.3% | 11.6% | 11.4% | 12.9% | 11.1% |
| 12 | 10.0% | 8.8% | 8.4% | 12.3% | 13.0% | 13.5% | 11.1% |
| 60 µg 25-hydroxyvitamin $D_3$ (Example Formulation D) | | | | | | | |
| 2 | 6.9% | 8.0% | 1.1% | 36.0% | 18.3% | 8.0% | 29.1% |
| 4 | 2.8% | 0.4% | 3.2% | 18.5% | 4.9% | 1.3% | 23.5% |
| 6 | 6.2% | 4.8% | 6.6% | 13.9% | 10.6% | 14.2% | 22.9% |
| 8 | 4.9% | 2.0% | 6.8% | 12.3% | 10.4% | 14.4% | 18.0% |
| 12 | 3.7% | 6.8% | 0.3% | 1.6% | 0.1% | 4.8% | 3.0% |
| 90 µg 25-hydroxyvitamin $D_3$ (Example Formulation E) | | | | | | | |
| 2 | 0.0% | 10.7% | 9.4% | 4.0% | 0.7% | 36.2% | 43.0% |
| 4 | 6.0% | 5.0% | 0.4% | 8.0% | 3.8% | 26.3% | 31.1% |
| 6 | 20.1% | 9.3% | 17.0% | 19.9% | 13.9% | 28.0% | 27.9% |
| 8 | 16.5% | 5.5% | 10.7% | 12.5% | 9.9% | 23.9% | 17.8% |
| 12 | 3.6% | 6.8% | 1.4% | 2.4% | 1.6% | 6.0% | 0.2% |

Figure 2A:
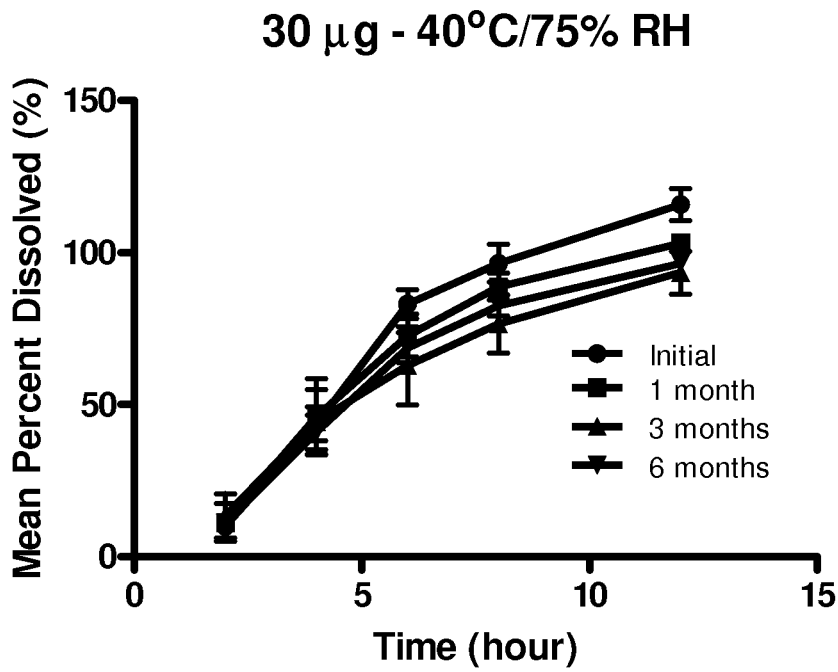
FIGS. 2A, 2B, and 2C show the dissolution profile of formulations comprising 30 μg, 60 μg, and 90 μg of 25-hydroxyvitamin $D_3$, respectively.
Figure 2B:
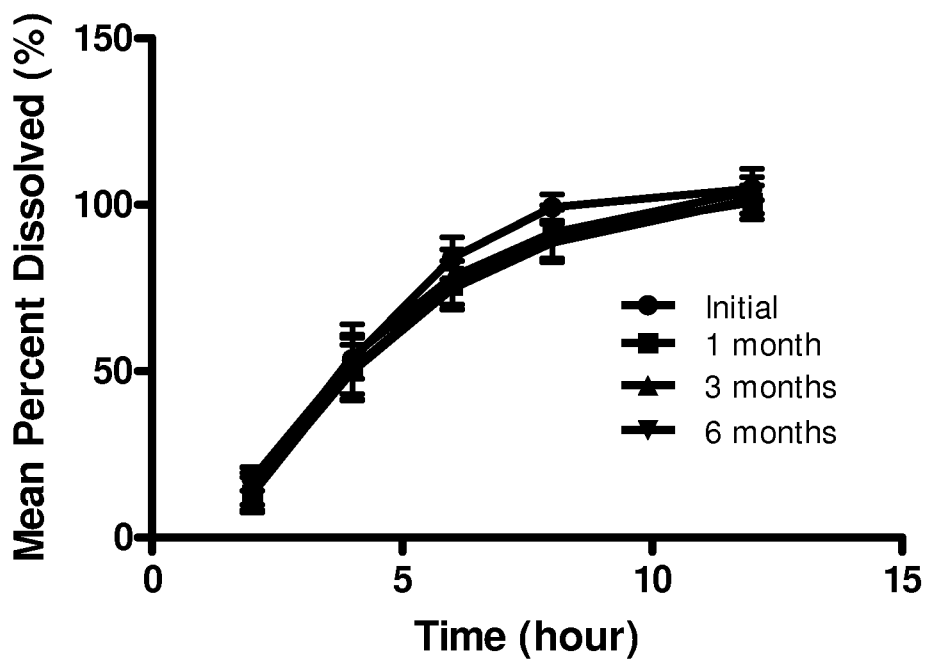
Figure 2C:
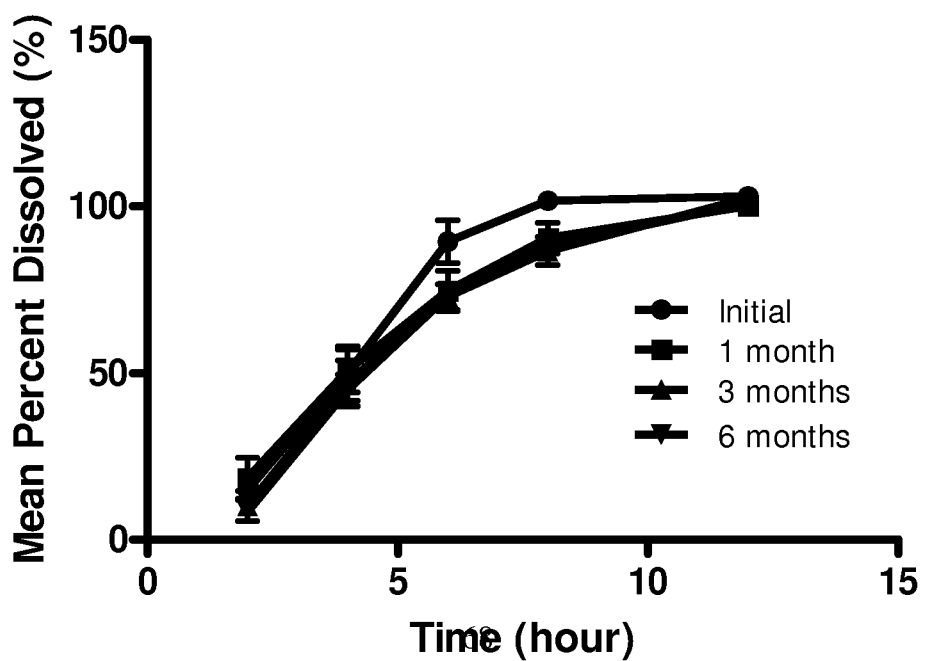

Example Formulations C to E also exhibited substantially stable dissolution profiles following storage at 40° C. and 75% RH for at least 6 months (FIG. 2). The dissolution results are summarized in the table below.

Dissolution Following Storage at 40° C./75% Relative Humidity

| Time (hours) | Initial % LC (% CV) | 1 month % LC (% CV) | 3 months % LC (% CV) | 6 months % LC (% CV) |
|---|---|---|---|---|
| 30 µg 25-hydroxyvitamin $D_3$ (Example Formulation C) | | | | |
| 2 | 10.1 (16.1) | 11.3 (54.3) | 13.5 (53.8) | 11.1 (14.8) |
| 4 | 43.6 (12.7) | 46 (27.1) | 44.4 (23.9) | 40.9 (13.9) |
| 6 | 83.1 (5.7) | 72.7 (9.7) | 62.8 (20.4) | 68.7 (7.3) |
| 8 | 96.4 (6.5) | 88.7 (5) | 76.5 (12.5) | 82.5 (4.1) |
| 12 | 115.8 (4.5) | 103.1 (0.9) | 93.4 (7.6) | 96.4 (2.8) |
| 60 µg 25-hydroxyvitamin $D_3$ (Example Formulation D) | | | | |
| 2 | 17.5 (20) | 12.9 (40.7) | 15.5 (37) | 13.9 (40) |
| 4 | 53.6 (19.6) | 50.7 (18.5) | 54.4 (12) | 49.8 (16.3) |
| 6 | 83.9 (7.5) | 75.8 (9.7) | 78.3 (10.6) | 74.7 (8.1) |
| 8 | 99.2 (3.9) | 91.2 (7.9) | 91.6 (9.1) | 88.5 (6.5) |
| 12 | 104.8 (3.3) | 100.7 (5.1) | 104.1 (6.5) | 101.5 (2.3) |
| 90 µg 25-hydroxyvitamin $D_3$ (Example Formulation E) | | | | |
| 2 | 14.9 (19.9) | 18.5 (32.5) | 10.2 (44.6) | 8.3 (34.7) |

-continued

Dissolution Following Storage at 40° C./75% Relative Humidity

| Time (hours) | Initial % LC (% CV) | 1 month % LC (% CV) | 3 months % LC (% CV) | 6 months % LC (% CV) |
|---|---|---|---|---|
| 4 | 49.9 (16.4) | 50.7 (12..8) | 47 (14.6) | 44.8 (10.6) |
| 6 | 89.4 (7.2) | 74.7 (8) | 72.9 (5.2) | 73 (3.4) |
| 8 | 101.7 (2.5) | 90.5 (5) | 86.6 (4.8) | 87.9 (3) |
| 12 | 103 (2.1) | 100.1 (1.4) | 102.5 (1.6) | 101.0 (1.9) |

The percent change between the amount of 25-hydroxyvitamin $D_3$ released following exposure to storage conditions compared to the initial amount released is summarized in the table below.

| Time (hours) | 1 month % change | 3 months % change | 6 months % change |
|---|---|---|---|
| 30 μg 25-hydroxyvitamin $D_3$ (Example Formulation C) | | | |
| 2 | 11.9% | 33.7% | 9.9% |
| 4 | 5.5% | 1.8% | 6.2% |
| 6 | 12.5% | 24.4% | 17.3% |
| 8 | 8.0% | 20.6% | 14.4% |
| 12 | 11.0% | 19.3% | 16.8% |
| 60 μg 25-hydroxyvitamin $D_3$ (Example Formulation D) | | | |
| 2 | 26.3% | 11.4% | 20.6% |
| 4 | 5.4% | 1.5% | 7.1% |
| 6 | 9.7% | 6.7% | 11.0% |
| 8 | 8.1% | 7.7% | 10.8% |
| 12 | 3.9% | 0.7% | 3.1% |
| 90 μg 25-hydroxyvitamin $D_3$ (Example Formulation E) | | | |
| 2 | 24.2% | 31.5% | 44.3% |
| 4 | 1.6% | 5.8% | 10.2% |
| 6 | 16.4% | 18.5% | 18.3% |
| 8 | 11.0% | 14.8% | 13.6% |
| 12 | 2.8% | 0.5% | 1.9% |

Figure 3A:
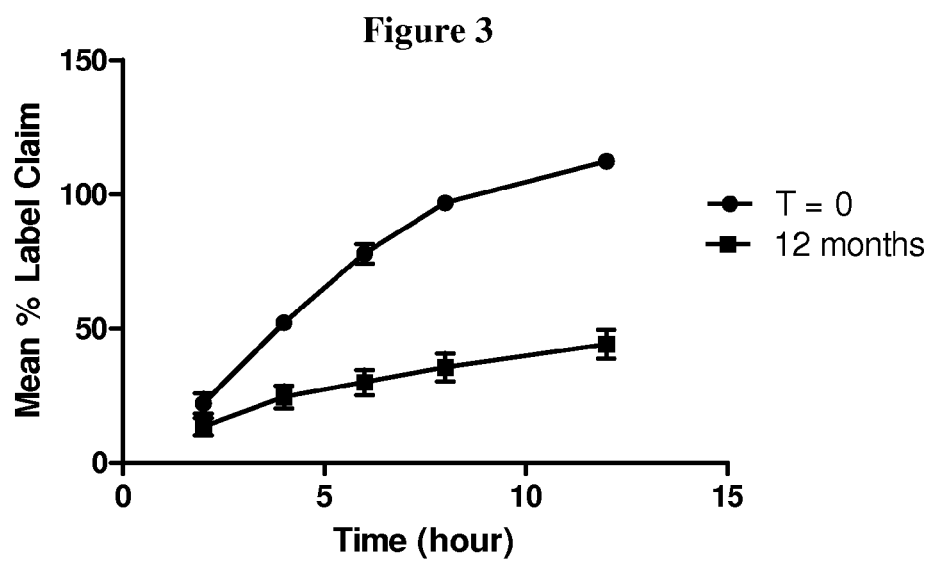
FIG. 3A shows the dissolution profile of a comparative formulation that does not contain a cellulosic compound.
Figure 3B:
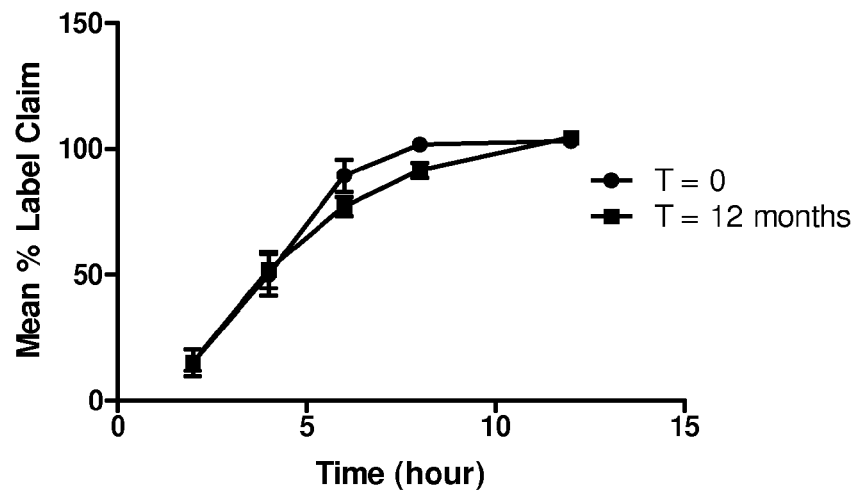
FIG. 3B shows the dissolution profile of a stabilized formulation according to the disclosure.

The stability of Comparative Formulation 1, which does not contain a cellulosic compound, and Example Formulation E comprising hydroxyl propyl methylcellulose was evaluated following storage for 12 months at 25° C. and 60% relative humidity (FIG. 3). The dissolution results are summarized in the table below.

Dissolution Following Storage at 25° C./60% Relative Humidity

| | Comparative Formulation 1 | | Example Formulation E | |
|---|---|---|---|---|
| Dissolution Time (hours) | Initial % LC | 12 months % LC | Initial % LC | 12 months % LC |
| 2 | 22.1 | 13.5 | 14.9 | 15.0 |
| 4 | 52.2 | 24.5 | 49.9 | 51.8 |
| 6 | 77.9 | 30.0 | 89.4 | 77.0 |
| 8 | 96.8 | 35.6 | 101.7 | 91.6 |
| 12 | 112.3 | 44.2 | 103.0 | 104.6 |

The percent change between the amount of 25-hydroxyvitamin $D_3$ released following exposure to storage conditions compared to the initial amount released is summarized in the table below.

| Dissolution Time (hours) | Comparative Formulation 1 % change from initial | Example Formulation E % change from initial |
|---|---|---|
| 2 | 38.9% | 0.7% |
| 4 | 53.1% | 3.8% |
| 6 | 61.5% | 13.9% |
| 8 | 63.2% | 9.9% |
| 12 | 60.6% | 1.6% |

Example 3—In Vivo Results for Unstabilized and Stabilized Controlled Release Formulations In vivo studies were conducted to evaluate the clinical pharmacokinetics of unstabilized and stabilized controlled release formulations of 25-hydroxyvitamin $D_3$ in human subjects. In Study A, 28 subjects with stage 3 or stage 4 CKD, secondary hyperparathyroidism (stage 3: 70-1000 pg/mL iPTH; stage 4: 110-1000 pg/mL iPTH), and vitamin D insufficiency (serum total baseline 25-hydroxyvitamin D of 15 ng/mL to 29 ng/mL) received a single oral dose of a controlled release capsule comprising 450 μg or 900 μg of 25-hydroxyvitamin $D_3$, 20.00 wt % hard paraffin, 37.85 wt % GMS, 9.75 wt % GELUCIRE 44/14, 2.32 wt % anhydrous ethanol, 30.06 wt % mineral oil, and 0.02 wt % BHT (Comparative Formulation 3) or a single intravenous dose of 448 μg 25-hydroxyvitamin $D_3$ in an ethanol solution. None of the formulations comprised a cellulosic compound.

The serum concentration of 25-hydroxyvitamin $D_3$ increased gradually following the administration of an oral dose. The increase in 25-hydroxyvitamin $D_3$ was dose proportional and reached an approximate mean maximum observed serum concentration (Cmax) of 32 ng/mL following the administration of the 900 μg capsule. The time at which Cmax occurred (Tmax) was approximately 13 hours post-dose. In contrast, concentrations of 25-hydroxyvitamin $D_3$ increased rapidly following the administration of the i.v. dose. Peak serum levels were achieved immediately following administration of the i.v. dose (Tmax=0.5 hours) and reached an approximate mean Cmax of 134 ng/mL. The bioavailability of the oral doses was approximately 6 to 11%. The terminal half-life ($t_{1/2}$) of 25-hydroxyvitamin $D_3$ following the administration of the oral dose was approximately 12 to 22 days. No adverse effects on serum calcium or phosphorous, or urine calcium were observed in any treatment group.

The mean serum total 1,25-dihydroxyvitamin D rose rapidly following the administration of the i.v. injection, increasing from pre-treatment baseline by approximately 13 pg/mL by 6 hours post-dose. In contrast, mean serum total 1,25-dihydroxyvitamin D increased dose proportionally and gradually by approximately 7 pg/mL by 48 hours post-dose following the administration of the 900 μg capsule.

Serum iPTH showed no meaningful change over the first 96 hours after the i.v. dose was administered. In contrast, serum PTH declined gradually following dosing, reaching a maximum suppression of approximately 20% from pretreatment baseline for subjects who received the 900 μg capsule. The observed pharmacokinetic parameters for all the treatment groups are summarized in the table below.

| Parameter | | 450 μg po (N = 9) n Mean (SD) Median Range | | 900 μg po (N = 9) n Mean (SD) Median Range | | 448 μg iv (N = 9) n Mean (SD) Median Range |
|---|---|---|---|---|---|---|
| | | | PK/PD Population Observed 25-hydroxyvitamin $D_3$ | | | |
| $AUC_{0-42\ days}$ (ng*h/mL) | 9 | 13353.12 (10606.74) 12196.45 888.39, 32885.95 | 9 | 21563.95 (9165.53) 17940.11 9292.88, 38631.91 | 9 | 43463.51 (12589.57) 47115.66 23340.59, 63006.78 |
| $AUC_{0-last}$ (ng*h/mL) | 9 | 13353.12 (10606.47) 12196.45 888.39, 32885.95 | 9 | 21563.95 (9165.53) 17940.11 9292.88, 38631.91 | 9 | 43463.51 (12589.75) 47115.66 23340.59, 63006.78 |
| $AUC_{0-inf}$ (ng*h/mL) | 9 | 81511.71 (103037.08) 54967.57 4927.95, 333366.90 | 9 | 122901.73 (114168.13) 79902.04 25729.84, 378935.59 | 9 | 137955.58 (66746.71) 123580.87 39282.49, 243322.76 |
| $C_{max}$ (ng/mL) | 9 | 25.18 (10.134) 20.52 15.35, 42.24 | 9 | 31.54 (15.765) 30.12 12.21, 67.01 | 9 | 133.99 (19.311) 133.68 91.71, 160.91 |
| $C_{last}$ (ng/mL) | 9 | 18.11 (7.846) 15.84 10.30, 29.80 | 9 | 19.08 (7.611) 21.37 7.30, 27.93 | 9 | 35.07 (12.330) 36.91 12.68, 53.39 |
| $t_{max}$ (h) | 9 | 13.11 (9.597) 10.00 6.00, 36.00 | 9 | 13.56 (9.989) 10.00 2.00, 30.00 | 9 | 0.49 (0.638) 0.25 0.083, 2.00 |
| $\lambda_z$ ($h^{-1}$) | 9 | 0.0015 (0.0028) 0.0003 0.0001, 0.0087 | 9 | 0.0003 (0.0002) 0.0004 0.0001, 0.0005 | 9 | 0.0005 (0.0002) 0.0004 0.0002, 0.0008 |
| $R^2$ | 9 | 0.89 (0.130) 0.96 0.662, 1.000 | 9 | 0.90 (0.169) 0.99 0.523, 0.998 | 9 | 0.91 (0.090) 0.93 0.730, 1.000 |
| $t_{1/2}$ (h) | 9 | 2477.72 (2581.24) 2483.61 79.24, 8615.11 | 9 | 3228.63 (2734.74) 1937.32 1300.13, 9646.71 | 9 | 1775.86 (779.13) 1694.69 871.46, 3297.78 |
| $V_d$ (L/ng) | 9 | 49.42 (18.30) 50.93 23.20, 72.76 | 9 | 45.06 (19.38) 40.080 20.77, 87.51 | 9 | 20.35 (7.42) 19.550 13.04, 32.68 |
| CL (L/ng*h) | 9 | 0.0499 (0.0155) 0.0182 0.0030, 0.2029 | 9 | 0.0155 (0.0119) 0.0125 0.0026, 0.0389 | 9 | 0.0095 (0.0065) 0.0081 0.0041, 0.0255 |
| F | NA | 0.306 (NA) NA NA | NA | 0.247 (NA) NA NA | NA | 1.000 (NA) NA NA |

The baseline-adjusted pharmacokinetic parameters for all the treatment groups are summarized in the table below.

| Parameter | | 450 μg po (N = 9) n Mean (SD) Median Range | | 900 μg po (N = 9) n Mean (SD) Median Range | | 448 μg iv (N = 9) n Mean (SD) Median Range |
|---|---|---|---|---|---|---|
| $AUC_{0-42\ days}$ (ng*h/mL) | 9 | 1394.89 (1911.41) 605.42 48.87, 4956.68 | 8 | 4525.43 (3123.29) 4801.54 148.07, 8843.74 | 9 | 19609.07 (5319.01) 18764.48 11066.02, 28611.05 |
| $AUC_{0-last}$ (ng*h/mL) | 9 | 1257.30 (2047.74) 48.87 −325.43, 4956.68 | 8 | 4274.27 (3488.40) 4801.54 −877.99, 8843.74 | 9 | 19609.07 (5319.01) 18764.48 11066.02, 28611.05 |
| $AUC_{0-inf}$ (ng*h/mL) | 9 | 3318.90 (4606.89) 547.25 50.78, 9878.03 | 8 | 6791.49 (5224.54) 6872.86 285.04, 14979.17 | 9 | 34543.75 (22103.97) 26962.25 16868.97, 89126.53 |
| $C_{max}$ (ng/mL) | 9 | 6.90 (4.266) 5.70 2.93, 14.87 | 8 | 14.17 (9.884) 12.30 2.55, 35.59 | 9 | 110.33 (14.536) 111.08 76.63, 127.40 |
| $C_{last}$ (ng/mL) | 9 | 2.36 (2.257) 2.05 0.16, 5.49 | 8 | 2.64 (1.784) 3.01 0.42, 5.40 | 9 | 11.40 (5.648) 9.01 5.84, 22.86 |
| $t_{max}$ (h) | 9 | 13.11 (9.597) 10.00 6.00, 36.00 | 8 | 15.00 (9.621) 10.00 8.00, 30.00 | 9 | 0.49 (0.638) 0.25 0.083, 2.00 |
| $\lambda_z$ ($h^{-1}$) | 6 | 0.018 (0.359) 0.0042 0.0008, 0.0910 | 7 | 0.0020 (0.0013) 0.0016 0.0008, 0.0037 | 9 | 0.0011 (0.0005) 0.0010 0.0004, 0.0021 |
| $R^2$ | 6 | 0.92 (0.101) 0.96 0.743, 0.999 | 6 | 0.99 (0.020) 0.99 0.948, 1.000 | 9 | 0.92 (0.086) 0.95 0.720, 0.999 |

| Parameter | 450 µg po (N = 9) n Mean (SD) Median Range | | 900 µg po (N = 9) n Mean (SD) Median Range | | 448 µg iv (N = 9) n Mean (SD) Median Range | |
|---|---|---|---|---|---|---|
| $t_{1/2}$ (h) | 6 | 307.86 (336.42) 165.72 7.61, 914.23 | 6 | 522.96 (320.80) 530.00 189.84, 879.31 | 9 | 745.86 (437.65) 663.43 337.37, 1834.71 |
| $V_d$ (L/ng) | 6 | 340.42 (269.11) 249.77 80.51, 771.79 | 6 | 82.92 (29.70) 77.11 39.96, 127.06 | 9 | 32.94 (11.00) 29.70 24.28, 58.95 |
| CL (L/ng*h) | 6 | 4.588 (7.525) 2.119 0.101, 19.692 | 6 | 0.141 (0.080) 0.1200 0.0668, 0.2860 | 9 | 0.036 (0.014) 0.037 0.011, 0.059 |
| F | NA | 0.064 (NA) NA NA | NA | 0.109 (NA) NA NA | NA | 1.000 (NA) NA NA |

In Study B, 20 healthy subjects with mean baseline serum 25-hydroxyvitamin D of about 24 ng/mL (range 11 ng/mL to 45 ng/mL) received a single oral dose of a stabilized controlled release capsule comprising 900 µg of 25-hydroxyvitamin $D_3$, 20.00 wt % hard paraffin, 10.00 wt % HPMC, 22.55 wt % GMS, 9.75 wt % GELUCIRE 44/14, 2.32 wt % anhydrous ethanol, 35.36 wt % mineral oil, and 0.02 wt % BHT (Example Formulation F) or a single intravenous dose of 448 µg 25-hydroxyvitamin $D_3$ in an ethanol solution.

The gradual increase in 25-hydroxyvitamin $D_3$ levels was demonstrated by the prolonged Tmax following administration of the stabilized oral formulation compared to the i.v. dose. The pharmacokinetic profile following administration of the stabilized oral formulation demonstrated a gradual increase in 25-hydroxyvitamin $D_3$ concentrations, with a mean Tmax of 28 hours, while avoiding rapid increases in blood levels in the majority of subjects. Administration of the i.v. dose resulted in a rapid increase in 25-hydroxyvitamin $D_3$ concentrations in all subjects. The avoidance of the rapid increase in 25-hydroxyvitamin $D_3$ levels was highlighted by the marked difference in the observed $C_{max}$ between the treatment groups. The Cmax following the oral dose was 58 ng/mL, compared to a Cmax of 153 ng/mL following the i.v. dose.

The exposure to 25-hydroxyvitamin $D_3$ following administration of the controlled release capsule was approximately two-fold lower than following the i.v. dose despite the oral dose being approximately two-fold higher, resulting in a bioavailability of approximately 25%. The $t_{1,2}$, clearance (CL) and volume of distribution (Vd) appeared to be similar between treatment groups. The values for $t_{1,2}$ and CL were consistent with the reported prolonged elimination of 25-hydroxyvitamin $D_3$. In addition, the Vd values suggested that 25-hydroxyvitamin $D_3$ was maintained in systemic circulation, likely highly bound to the DBP. The observed pharmacokinetic parameters for all the treatment groups are summarized in the table below.

| Parameter | 900 µg CTAP101 Capsules (N = 10) | 448 µg CTAP101 Injection (N = 10) |
|---|---|---|
| $AUC_{0-t}$ (ng · h/mL) | | |
| Mean (SD) | 21545.2 (7054.02) | 25274.44 (7206.93) |
| Median | 19904.00 | 25810.85 |
| Minimum, Maximum | 10176.40, 35885.02 | 8434.02, 35382.55 |
| $AUC_{0-inf}$ (ng · h/mL) | | |
| Mean (SD) | 77945.13 (55896.15) | 55234.52 (27268.64) |
| Median | 58974.22 | 51247.29 |
| Minimum, Maximum | 19504.43, 194796.33 | 22979.18, 119865.38 |
| $C_{max}$ (ng/mL) | | |
| Mean (SD) | 57.657 (39.3810) | 153.029 (20.8620) |
| Median | 37.925 | 152.890 |
| Minimum, Maximum | 24.43, 146.86 | 125.94, 185.33 |
| $t_{max}$ (h) | | |
| Mean (SD) | 28.100 (27.4000) | 0.272 (0.2910) |
| Median | 21.000 | 0.167 |
| Minimum, Maximum | 4.00, 96.00 | 0.05, 1.00 |
| $t_{1/2}$ (h) | | |
| Mean (SD) | 1389.40 (1144.48) | 660.23 (415.82) |
| Median | 1042.60 | 607.65 |
| Minimum, Maximum | 557.32, 4173.67 | 238.46, 1733.68 |
| $\lambda_z$ (h$^{-1}$) | | |
| Mean (SD) | 0.00072 (0.00036) | 0.00136 (0.00071) |
| Median | 0.00067 | 0.00115 |
| Minimum, Maximum | 0.00017, 0.00124 | 0.00040, 0.00291 |
| CL (L/h) | | |
| Mean (SD) | 0.0064 (0.0027) | 0.0098 (0.0046) |
| Median | 0.0066 | 0.0087 |
| Minimum, Maximum | 0.0018, 0.0098 | 0.0037, 0.0195 |
| Vd (L) | | |
| Mean (SD) | 9.27 (0.97) | 7.50 (1.19) |
| Median | 9.39 | 7.24 |
| Minimum, Maximum | 7.93, 10.49 | 6.02, 9.77 |
| $R^2$ | | |
| Mean (SD) | 0.80 (0.24) | 0.92 (0.075) |
| Median | 0.88 | 0.94 |
| Minimum, Maximum | 0.25, 0.99 | 0.74, 1.0 |
| F* | | |
| Mean (SD) | 0.42 (0.14) | N/A |
| Median | 0.39 | N/A |
| Minimum, Maximum | 0.20, 0.71 | N/A |

*average of individual subjects' bioavailabilities
Abbreviations: N/A, not applicable The baseline-adjusted pharmacokinetic parameters for all the treatment groups are summarized in the table below.

| Parameter | 900 μg CTAP101 Capsules (N = 10) | 448 μg CTAP101 Injection (N = 10) |
|---|---|---|
| AUC$_{0-t}$(ng · h/mL) | | |
| Mean (SD) | 6891.81 (6678.97) | 13583.95 (3908.42) |
| Median | 4360.23 | 14853.46 |
| Minimum, Maximum | 1017.88, 20340.68 | 5302.50, 17194.59 |
| AUC$_{0-inf}$ (ng · h/mL) | | |
| Mean (SD) | 9418.00 (9410.58) | 17735.09 (5249.38) |
| Median | 5420.04 | 18229.25 |
| Minimum, Maximum | 1179.07, 28031.64 | 9820.16, 25534.45 |
| C$_{max}$ (ng/mL) | | |
| Mean (SD) | 35.867 (39.3886) | 133.653 (20.7925) |
| Median | 14.910 | 133.785 |
| Minimum, Maximum | 6.50, 120.52 | 103.88, 166.34 |
| t$_{max}$ (h) | | |
| Mean (SD) | 28.100 (27.4001) | 0.272 (0.2914) |
| Median | 21.000 | 0.167 |
| Minimum, Maximum | 4.00, 96.00 | 0.05, 1.00 |
| t$_{1/2}$ (h) | | |
| Mean (SD) | 270.61 (215.00) | 264.08 (82.23) |
| Median | 194.00 | 269.57 |
| Minimum, Maximum | 107.90, 832.70 | 132.46, 382.99 |
| $\lambda_z$ (h$^{-1}$) | | |
| Mean (SD) | 0.00362 (0.00182) | 0.00292 (0.00112) |
| Median | 0.00363 | 0.00257 |
| Minimum, Maximum | 0.00083, 0.00624 | 0.00181, 0.00523 |
| CL (L/h) | | |
| Mean (SD) | 0.027 (0.0063) | 0.028 (0.0093) |
| Median | 0.028 | 0.025 |
| Minimum, Maximum | 0.012, 0.033 | 0.018, 0.046 |
| Vd (L) | | |
| Mean (SD) | 8.78 (3.08) | 9.74 (2.02) |
| Median | 8.08 | 9.47 |
| Minimum, Maximum | 5.06, 14.17 | 6.54, 13.27 |
| R$^2$ | | |
| Mean (SD) | 0.83 (0.22) | 0.92 (0.072) |
| Median | 0.88 | 0.94 |
| Minimum, Maximum | 0.25, 1.0 | 0.74, 1.0 |
| F* | | |
| Mean (SD) | 0.25 (0.24) | N/A |
| Median | 0.16 | N/A |
| Minimum, Maximum | 0.037, 0.75 | N/A |

*average of individual subjects' bioavailabilities
Abbreviations: N/A, not applicable The study demonstrated that the stabilized controlled release formulation modified the rate of absorption of 25-hydroxyvitamin D$_3$, yielding a more gradual increase in serum 25-hydroxyvitamin D$_3$ levels while maintaining the distribution and elimination characteristics. The stabilized formulation demonstrated improved pharmacokinetic parameters, such as increased Tmax, AUC, and bioavailability, compared to the same dose of the unstabilized formulation in Study A.

In Study C, 78 subjects with stage 3 CKD (eGFR 25-70 mL/min/1.73 m$^2$), SHPT (>70 pg/mL plasma iPTH) and vitamin D insufficiency (serum total baseline 25-hydroxyvitamin D of 10 ng/mL to 29 ng/mL) received daily oral doses of stabilized controlled release formulations comprising 30 μg, 60 μg, or 90 μg of 25-hydroxyvitamin D$_3$, 20.00 wt % hard paraffin, 10.00 wt % HPMC, 22.55 wt % GMS, 9.75 wt % GELUCIRE 44/14, 2.32 wt % anhydrous ethanol, 35.36 wt % mineral oil, and 0.02 wt % BHT (Example Formulations C, D, and E from Example 2) or placebo for 6 weeks.

Figure 4:
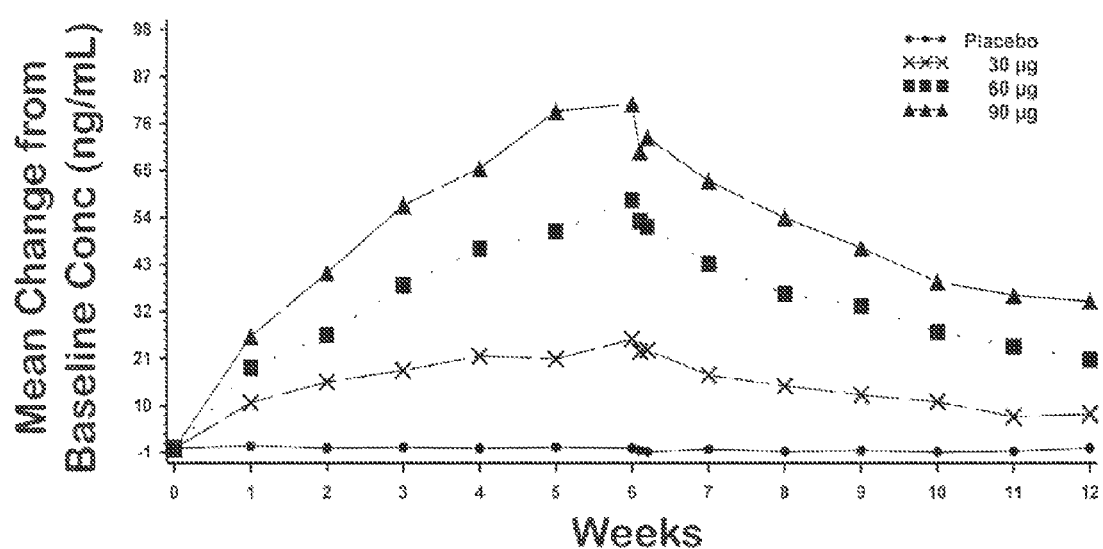
FIG. 4 shows the resulting mean baseline-adjusted calcifediol concentrations by treatment group (PK population) for the patients described in Example 4 treated with a formulation according to the disclosure.

The mean baseline serum 25-hydroxyvitamin D$_3$ concentrations were comparable across treatment groups and ranged from approximately 16 to 20 ng/mL. Following treatment with 25-hydroxyvitamin D$_3$, mean levels of serum 25-hydroxyvitamin D$_3$ increased gradually and in a dose-proportional manner following repeated daily administration of 25-hydroxyvitamin D$_3$ and began to approach steady-state by 6 weeks (FIG. 4). The mean baseline adjusted Cmax values were approximately 28, 60 and 86 ng/mL for the groups administered 30 μg, 60 μg and 90 μg of 25-hydroxyvitamin D$_3$, respectively. Mean exposures to 25-hydroxyvitamin D$_3$, assessed as background adjusted AUC$_{0-6 \text{ Weeks}}$, were dose proportional across dose groups. Following the last dose, mean serum 25-hydroxyvitamin D$_3$ levels declined slowly, but by the end of the study remained above baseline for all groups. Mean t$_{1/2}$ was determined to be approximately between 25 to 50 days. The baseline-adjusted pharmacokinetic parameters for 25-hydroxyvitamin D$_3$ are summarized in the table below.

| | Placebo | 30 μg | 60 μg | 90 μg |
|---|---|---|---|---|
| Baseline (ng/mL) | | | | |
| Mean (SD) | 16.4 (8.2) | 16.2 (7.3) | 19.8 (8.7) | 18.4 (9.8) |
| Median | 12.9 | 17.2 | 21.2 | 16.7 |
| Minimum, Maximum | 4.4, 30.4 | 5.0, 25.8 | 5.8, 32.5 | 6.7, 38.9 |
| C$_{max}$ (ng/mL) | | | | |
| Mean (SD) | 4.1 (3.5) | 27.8 (8.2) | 60.3 (19.0) | 85.7 (26.9) |
| Median | 3.1 | 28.1 | 60.8 | 76.0 |
| Minimum, Maximum | 0.6, 13.8 | 10.8, 43.4 | 30.3, 89.5 | 55.4, 146.4 |
| AUC$_{0-6 \text{ Weeks}}$ (ng · d/mL) | | | | |
| Mean (SD) | 45.9 (60.0) | 709.2 (246.3) | 1531.4 (374.8) | 2134.3 (584.3) |
| Median | 32.1 | 6843.0 | 1573.0 | 1963.8 |
| Minimum, Maximum | −60.1, 222.3 | 307.8, 1249.0 | 712.7, 2221.8 | 1377.5, 3207.3 |
| t$_{max}$ (d) | | | | |
| Mean (SD) | NA | 37.8 (10.4) | 41.1 (5.2) | 42.6 (5.3) |
| Median | NA | 42.50 | 43.0 | 43.0 |
| Minimum, Maximum | NA | 8.0, 44.0 | 29.0, 45.0 | 35.0, 57.0 |

-continued

|  | Placebo | 30 μg | 60 μg | 90 μg |
|---|---|---|---|---|
| $t_{1/2}$ (d) | | | | |
| Mean (SD) | NA | 25.8 (16.3) | 33.1 (9.3) | 50.1 (51.0) |
| Median | NA | 24.1 | 31.6 | 37.7 |
| Minimum, Maximum | NA | 5.2, 52.6 | 17.4, 52.3 | 23.2, 224.0 |

Mean baseline serum 1,25-dihydroxyvitamin D concentrations were comparable across treatment groups and increased gradually, similar to the effect on serum 25-hydroxyvitamin $D_3$ concentrations. Mean±SD baseline-adjusted Cmax values were higher in the 60 μg and 90 μg groups (18.4±6.24 and 19.9±14.30 ng/mL, respectively) compared to the placebo and 30 μg groups (5.7±6.35 and 6.4±7.66 ng/mL, respectively). Mean exposures to 1,25-dihydroxyvitamin D, assessed as baseline-adjusted $AUC_{0-6\ weeks}$, were dose-proportional across the 25-hydroxyvitamin $D_3$ dose groups. The baseline-adjusted pharmacokinetic parameters for 1,25-dihydroxyvitamin D are summarized in the table below.

|  | Placebo N = 23 | 30 μg N = 12 | 60 ng N = 16 | 90 μg N = 14 |
|---|---|---|---|---|
| Baseline (pg/mL) | | | | |
| Mean (SD) | 20.8 (10.11) | 18.3 (7.53) | 20.6 (7.62) | 20.6 (7.29) |
| Median | 17.0 | 17.0 | 18.0 | 21.0 |
| Minimum, Maximum | 7.0, 41.4 | 5.1, 30.7 | 8.2, 33.6 | 9.3, 34.5 |
| $C_{max}$ (pg/mL) | | | | |
| Mean (SD) | 7.6 (5.71) | 6.4 (7.66) | 18.4 (6.24) | 19.9 (14.30) |
| Median | 4.9 | 5.0 | 18.4 | 18.9 |
| Minimum, Maximum | 1.9, 22.6 | −6.3, 21.0 | 7.3, 29.9 | −11.6, 48.3 |
| $AUC_{0-6\ Weeks}$ (g · d/mL) | | | | |
| Mean (SD) | 11.5 (112.97) | 100.6 (185.38) | 249.9 (198.83) | 371.1 (290.81) |
| Median | 16.2 | 23.0 | 298.7 | 352.2 |
| Minimum, Maximum | −267.1, 219.8 | −145.4, 452.3 | −191.7, 563.6 | −5.8, 1235.8 |
| $t_{max}$ (d) | | | | |
| Mean (SD) | 24.4 (15.55) | 16.8 (16.09) | 26.4 (11.52) | 25.5 (13.88) |
| Median | 23.0 | 12.0 | 23.0 | 23.00 |
| Minimum, Maximum | 2.0, 45.0 | 1.0, 44.0 | 8.0, 44.0 | 1.0, 44.0 |

The stabilized controlled release formulations of 25-hydroxyvitamin $D_3$ increased serum total 25-hydroxyvitamin D levels to ≥30 ng/mL in significantly greater number of subjects in all active groups compared to placebo. Similarly, the stabilized formulations significantly decreased mean plasma iPTH from baseline in all dose groups compared to placebo.

Daily administration of 25-hydroxyvitamin $D_3$ in a stabilized controlled release formulation increased mean serum total 25-hydroxyvitamin D in proportion to the dose administered. The lowest administered dose (30 μg) increased serum total 25-hydroxyvitamin D at end of treatment by 15.6±1.7 (SE) ng/mL from pre-treatment baseline (21.7±1.8 ng/mL) and the highest dose (90 μg) increased serum total 25-hydroxyvitamin D by 61.1±6.1 ng/mL from 21.8±1.2 ng/mL. In contrast, a decrease at end of treatment of 1.2±0.7 ng/mL was observed in the combined placebo groups. Differences between the treatment and placebo groups were significant for all three dose levels studied (p<0.0001). The mean serum 25-hydroxyvitamin D level in the 30 μg dose group at the end of treatment was 37.3±1.8 ng/mL, (slightly higher than K/DOQI-specified minimum adequate level of 30 ng/mL), indicating that 30 μg was the minimum effective dose.

The percentage of treated subjects achieving serum total 25-hydroxyvitamin D levels of ≥30 ng/mL at end of treatment was 92.3%, 100.0% and 100.0% in the 30 μg, 60 μg and 90 μg dose groups compared with 0% in the placebo group. These differences in response rates between active and placebo treatment were all significant (p<0.001).

Mean plasma iPTH decreased at end of treatment in proportion to the administered dose of 25-hydroxyvitamin $D_3$. The lowest administered dose (30 μg) decreased iPTH by 20.2±5.8 (SE) % from pre-treatment baseline, and the highest dose (90 μg) decreased iPTH by 35.9±4.2%. An increase of 17.2±7.8% was observed at end of treatment in the combined placebo groups. Differences between groups receiving 25-hydroxyvitamin $D_3$ and placebo were significant for all three dose levels studied (p<0.005) and they compared favorably with differences observed with longer treatment in placebo-controlled studies with the more potent and calcemic oral vitamin D hormone replacement therapies (e.g., doxercalciferol, paricalcitol and calcitriol).

Percentages of subjects receiving 25-hydroxyvitamin $D_3$ who achieved confirmed reductions (i.e., two consecutive measurements) in iPTH of at least 20% or 30% from pre-treatment baseline at EOT increased with dose through 60 μg. Similar response rates were observed in the 60 and 90 μg treatment groups, indicating that no further benefit in iPTH lowering was observed in this study for the 90 μg dose. Response rates for a confirmed 20% reduction in iPTH were 38.5%, 70.6% and 76.5% for the 30 μg, 60 μg and 90 μg dose groups respectively compared with 9.7% in the combined placebo group. Differences in the observed response rates for a 20% reduction were significant only for the 60 μg and 90 μg dose groups (p<0.005) and for a 30% reduction were significant in all three dose groups (p<0.05). The data supported the conclusion that 30 μg per day of 25-hydroxyvitamin $D_3$ in a stabilized controlled release formulation is the minimum effective dose.

The stabilized formulations of 25-hydroxyvitamin $D_3$ had no clinically significant effect on corrected albumin-corrected serum calcium, serum phosphorus and urinary calcium excretion. There were no adverse effects on serum calcium or serum phosphorus or urine calcium during the 6-week treatment period.

Pharmacokinetic analyses revealed that the stabilized formulations of 25-hydroxyvitamin $D_3$ increased 25-hydroxyvitamin $D_3$ exposure over 6 weeks (AUC and $C_{max}$) in a dose proportional manner across the three dose groups with no difference in $t_{1/2}$. Following 6 weeks of administration, the three treatment groups had not quite reached steady state. However, steady state modeling demonstrated that steady state would have been achieved by 7-9 weeks in all dose groups.

Data from this study clearly demonstrated that stabilized controlled release formulations of 25-hydroxyvitamin $D_3$ were effective in elevating serum total 25-hydroxyvitamin D to the minimum adequate level of 30 ng/mL and lowering plasma iPTH. The study also showed that stabilized formulations of 25-hydroxyvitamin $D_3$ had no clinically meaningful impact on serum calcium or phosphorous at the doses investigated.

Example 4—Pharmacokinetic and Pharmacodynamic Profile of Modified-Release Calcifediol in CKD Subjects with Secondary Hyperparathyroidism and Vitamin D Insufficiency A multi-center, randomized, double blind, placebo-controlled, repeat dose, safety, efficacy and PK/PD study of stabilized, sustained release 25-hydroxyvitamin $D_3$ (calcifediol, $25D_3$) capsules was conducted in 2 cohorts of subjects. Male and female subjects aged 18 to 85 years with stage 3 CKD (eGFR of 25-70 mL/min/1.73 m$^2$), vitamin D insufficiency (serum 25-hydroxyvitamin D≥10 and ≤29 ng/mL), SHPT (plasma iPTH >70 pg/mL) and not requiring regular hemodialysis, were recruited for this study. Eligible subjects in the first cohort were randomized into 3 treatment groups in a 1:1:1 ratio: 2 groups received the capsules at daily oral doses of 60 or 90 μg, respectively, and 1 group received a matching placebo capsule. Subjects in cohort 2 were randomized into 2 treatment groups in a 1:1 ratio: 1 group received 30 μg capsules daily and the other received placebo. Subjects in each cohort completed 6 weeks of treatment and entered a 6 week follow-up period, during which PK and PD samples were collected weekly. Serum calcium (Ca), phosphorus (P), $25D_3$, total 1,25-dihydroxyvitamin D (1,25D) and plasma iPTH were monitored weekly during 6 weeks of treatment and 6 weeks of follow-up. ANCOVA models examined the association of $25D_3$ exposure with change from baseline for 1,25D and iPTH. Covariates included were baseline eGFR, body weight and height, gender, age, race, diabetic status, and baseline concentration of 1,25D or iPTH.

FIG. 4 shows the resulting mean baseline-adjusted calcifediol concentrations by treatment group (PK population). Mean levels of serum calcifediol increased gradually and in a dose-proportional manner and began to approach steady-state by 6 weeks. After 6 weeks of follow-up, levels decreased but remained above baseline in all active-treated groups.

FIG. 5 shows the resulting summary baseline-adjusted PK parameters for calcifediol concentrations by treatment group (PK population).

Figures 6, 7:
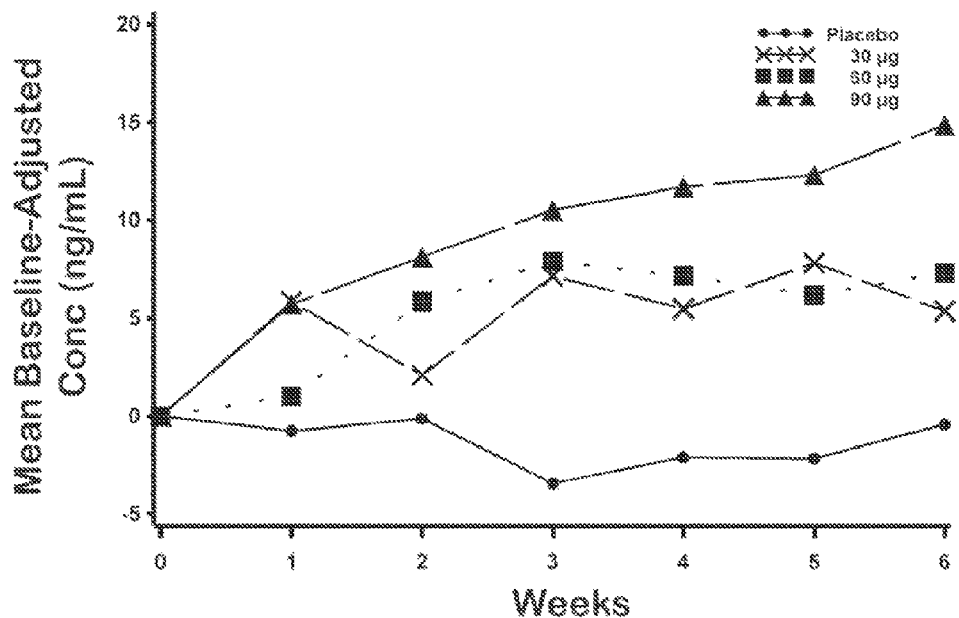
FIG. 6 shows the resulting mean baseline-adjusted serum 1,25-dihydroxyvitamin D levels during the 6-week treatment (PK population) for the patients described in Example 4 treated with a formulation according to the disclosure.
FIG. 7 shows a summary of the resulting baseline-adjusted repeat-dose PK parameters for serum 1,25-dihydroxyvitamin D by treatment group (PK population) for the patients described in Example 4 treated with a formulation according to the disclosure.

FIG. 6 shows the resulting mean baseline-adjusted serum 1,25-dihydroxyvitamin D levels during the 6-week treatment (PK population). Mean baseline-adjusted serum total 1,25 dihydroxyvitamin D levels increased over time in those subjects administered the active capsules, compared to those subjects administered placebo.

FIG. 7 shows a summary of the resulting baseline-adjusted repeat-dose PK parameters for serum 1,25-dihydroxyvitamin D by treatment group (PK population).

Figures 8, 9:
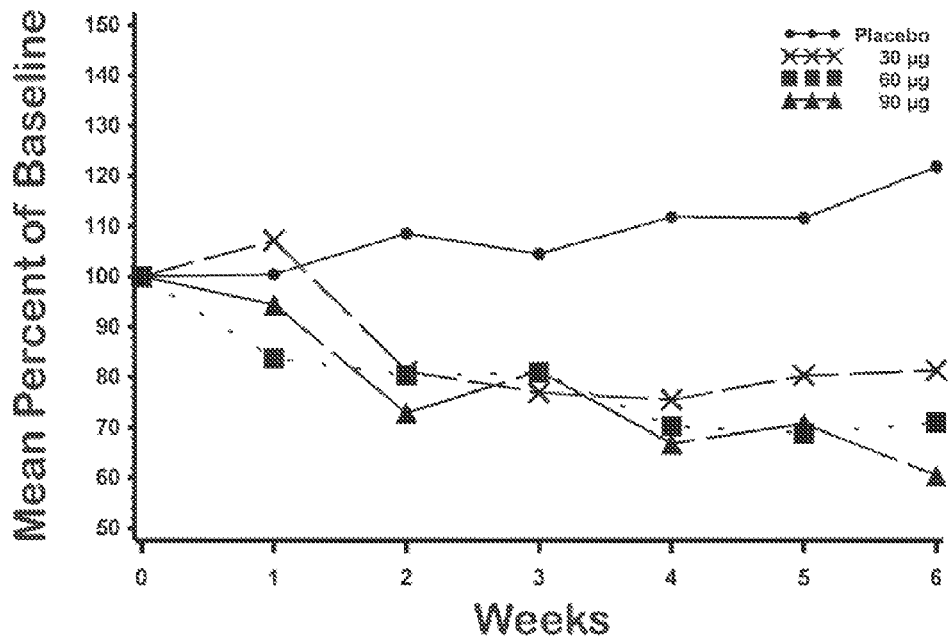
FIG. 8 shows the resulting mean percent of baseline in plasma iPTH levels during the 6-week treatment (PK population) for the patients described in Example 4 treated with a formulation according to the disclosure.
FIG. 9 shows a summary of the resulting baseline-adjusted repeat-dose PK parameters for plasma iPTH by treatment group (PK population) for the patients described in Example 4 treated with a formulation according to the disclosure.

FIG. 8 shows the resulting mean percent of baseline in plasma iPTH levels during the 6-week treatment (PK population). The active capsules significantly decreased mean plasma iPTH from baseline by 21%, 33% and 39% in all dose groups (30, 60 and 90 μg, respectively) compared to a 17% increase in the combined placebo group.

FIG. 9 shows a summary of the resulting baseline-adjusted repeat-dose PK parameters for plasma iPTH by treatment group (PK population).

Figure 10:
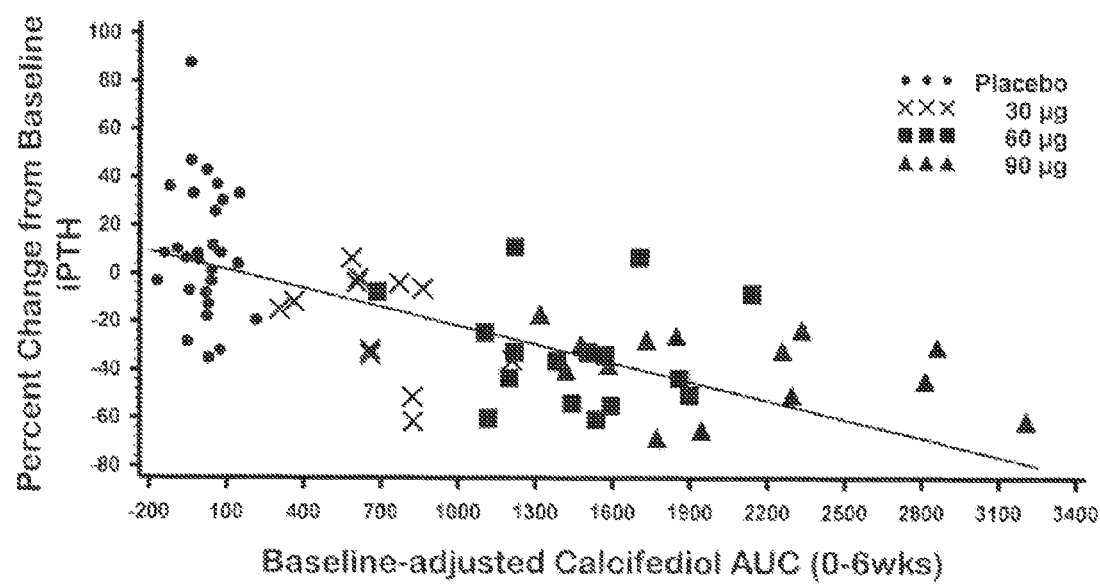
FIGS. 10 and 11 show the percent change from baseline at EOT for plasma iPTH relative to baseline-adjusted calcifediol and 1,25-dihydroxyvitamin D exposure ($AUC_{0-6wk}$) in the PK Population for the patients described in Example 4 treated with a formulation according to the disclosure.
Figure 11:
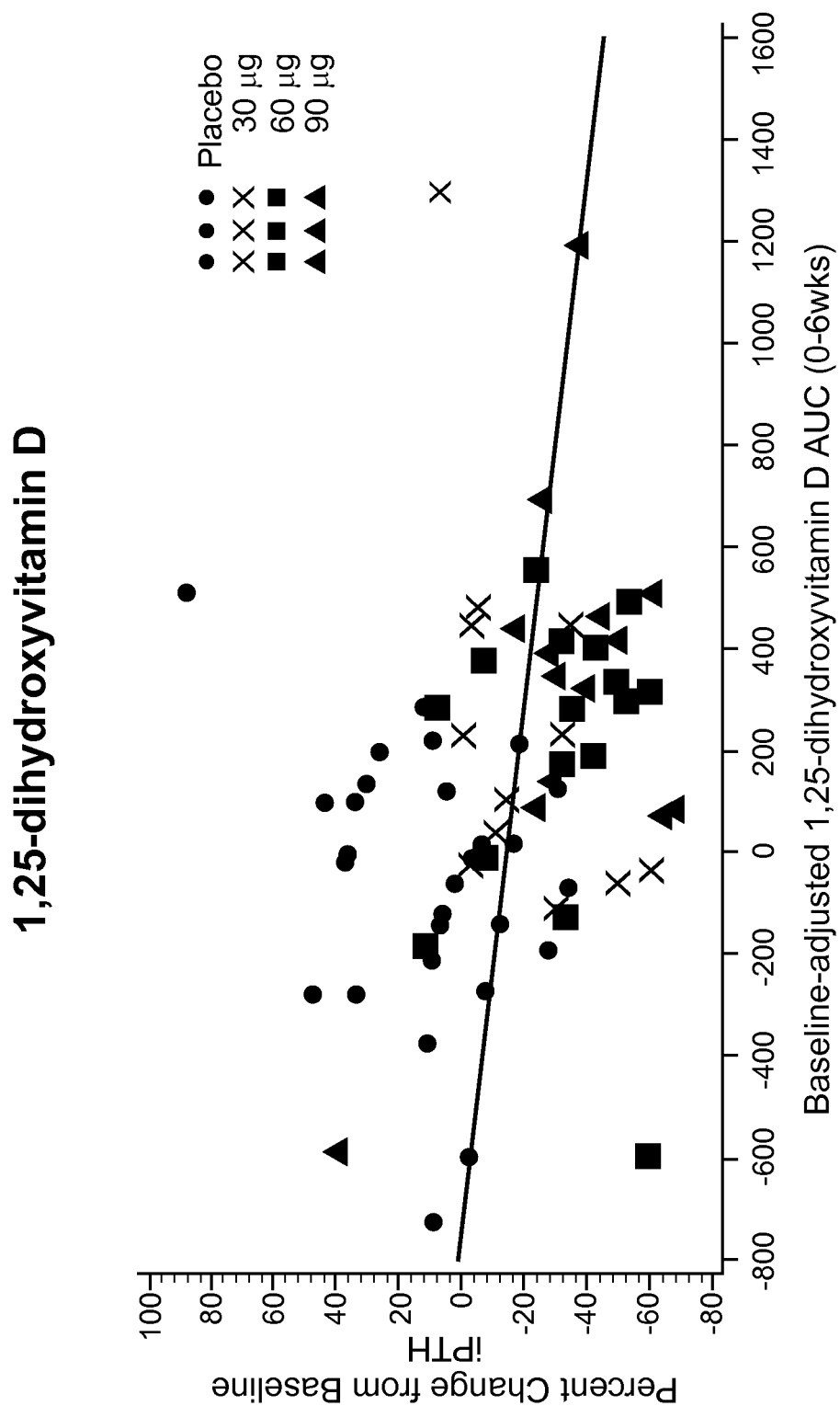

FIGS. 10 and 11 show the percent change from baseline at EOT for plasma iPTH relative to baseline-adjusted calcifediol and 1,25-dihydroxyvitamin D exposure ($AUC_{0-6wk}$) in the PK Population. Percent reductions in plasma iPTH from baseline to EOT increased as serum calcifediol and total 1,25 dihydroxyvitamin D exposures during treatment (expressed as baseline-adjusted $AUC_{0-6wk}$) increased.

The stabilized, sustained release 25-hydroxyvitamin $D_3$ capsules normalized 25D levels in the majority of subjects and significantly reduced iPTH in all dose groups (30, 60 and 90 μg). The stabilized, sustained release 25-hydroxyvitamin $D_3$ capsules increased serum $25D_3$ and serum 1,25D levels gradually with dose-dependent increases in exposure. Both $25D_3$ and total 1,25D exposure were significantly and inversely associated with change from baseline for plasma iPTH. Only eGFR was a significant covariate in both models. These findings demonstrate that the stabilized, sustained release 25-hydroxyvitamin $D_3$ capsules reliably normalized 25D levels, increased serum 1,25D levels and suppressed elevated plasma iPTH without clinically meaningful effects on serum Ca and P at the doses investigated.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

Embodiments contemplated in view of the foregoing description include those described in the following numbered paragraphs.

1. A controlled release formulation of a vitamin D compound comprising one or both of 25-hydroxyvitamin $D_2$ and 25-hydroxyvitamin $D_3$, the formulation comprising a matrix that releasably binds and controllably releases the vitamin D compound, the matrix comprising a cellulose derivative.

2. A stabilized formulation for controlled release of a vitamin D compound in the gastrointestinal tract of a subject which ingests the formulation, the formulation comprising a mixture of:
one or both of 25-hydroxyvitamin $D_2$ and 25-hydroxyvitamin $D_3$;
and an effective amount of a stabilizing agent, which is optionally a cellulosic compound, to maintain a difference of less than 30% between the amount of vitamin D compound released at any given time point after four hours during in vitro dissolution after two months exposure to storage conditions of 25° C. and 60% relative humidity and the amount released at the same dissolution time point during in vitro dissolution conducted prior to exposing the formulation to the storage conditions.

3. A stabilized formulation for controlled release of a vitamin D compound, said formulation comprising a mixture of:
one or both of 25-hydroxyvitamin $D_2$ and 25-hydroxyvitamin $D_3$;
a wax matrix; and
a stabilizing agent, which is optionally a cellulosic compound.

4. A stabilized formulation for controlled release of a vitamin D compound in the gastrointestinal tract of a subject which ingests the formulation, said formulation comprising a mixture of:
one or both of 25-hydroxyvitamin $D_2$ and 25-hydroxyvitamin $D_3$;
a wax matrix; and
a stabilizing agent, which is optionally a cellulosic stabilizing agent.

5. A stabilized formulation for controlled release of a vitamin D, said formulation comprising a mixture of:
one or both of 25-hydroxyvitamin $D_2$ and 25-hydroxyvitamin $D_3$;
a wax matrix; and
an effective amount of a stabilizing agent, optionally a cellulosic compound, to maintain a difference of less than 30% between the amount of vitamin D compound released at any given time point after four hours during in vitro dissolution testing after exposure for two months to storage conditions of 25° C. and 60% relative humidity and the amount released at the same dissolution time point during in vitro dissolution conducted prior to exposing the formulation to the storage conditions.

6. A stabilized formulation for controlled release of a vitamin D compound in the gastrointestinal tract of a subject which ingests the formulation, said formulation comprising a mixture of:
an active-loaded wax matrix comprising one or both of 25-hydroxyvitamin $D_2$ and 25-hydroxyvitamin $D_3$; and
a cellulosic stabilizing agent;
wherein the formulation releases an amount of 25-hydroxyvitamin D during in vitro dissolution after two months exposure to storage of 25° C. and 60% relative humidity that varies at any given dissolution time point compared to the amount released at the same dissolution time point during in vitro dissolution conducted prior to exposing the formulation to the storage conditions by 30% or less in the absence of the cellulosic stabilizing agent.

7. In a formulation for controlled release of a vitamin D compound in the gastrointestinal tract of a subject which ingests the formulation, the improvement comprising admixing a cellulosic stabilizing agent into the formulation.

8. In a formulation for controlled release of a vitamin D compound in the gastrointestinal tract of a subject which ingests the formulation, the improvement comprising an effective amount of a cellulosic compound admixed in the formulation to maintain a change of less than 30% in the amount of 25-hydroxyvitamin D released during in vitro dissolution after exposure to storage conditions of at least one month at 25° C. and 60% relative humidity at any given dissolution time point after four hours compared to the amount released at the same dissolution time point during in vitro dissolution conducted prior to exposing the formulation to the storage conditions.

9. The formulation according to any of the preceding paragraphs, wherein the cellulosic compound or cellulosic stabilizing agent comprises a cellulose ether.

10. The formulation according to paragraph 9, wherein the cellulose ether is selected from the group consisting of methylcellulose, hydroxyl propyl methylcellulose, hydroxyl ethyl methylcellulose, hydroxyl ethyl cellulose, and hydroxyl propyl cellulose.

11. The formulation according to paragraph 9, wherein the cellulosic compound or cellulosic stabilizing agent is hydroxyl propyl methylcellulose.

12. The formulation according to any of the preceding paragraphs, wherein the formulation releases an amount of 25-hydroxyvitamin D during in vitro dissolution after exposure to storage conditions for 2 months at 25° C. and 60% relative humidity that varies at any given dissolution time point after four hours compared to the amount released at the same dissolution time point during in vitro dissolution conducted prior to exposing the formulation to the storage conditions, by 30% or less.

13. The formulation according to any of the preceding paragraphs, wherein the formulation releases an amount of 25-hydroxyvitamin D during in vitro dissolution after exposure to storage conditions for one month at 40° C. and 75% relative humidity that varies at any given dissolution time point after four hours compared to the amount released at the same dissolution time point during in vitro dissolution conducted prior to exposing the formulation to the storage conditions, by 30% or less.

14. The formulation according to any one of the preceding paragraphs, wherein the matrix comprises a wax matrix comprising a controlled release agent, an emulsifier, and an absorption enhancer.

15. The formulation according to paragraph 14, wherein the controlled release agent comprises paraffin.

16. The formulation according to paragraph 14 or 15, wherein the emulsifier has a HLB value less than 7.

17. The formulation according to paragraph 16, wherein the emulsifier comprises glycerol monostearate.

18. The formulation according to any one of paragraphs 14 to 17, wherein the absorption enhancer has a HLB value in a range of about 13 to about 18.

19. The formulation according to paragraph 18, wherein the absorption enhancer is a mixture of lauroyl macrogolglycerides and lauroyl polyoxylglycerides.

20. The formulation according to any of the preceding paragraphs, wherein the vitamin D compound comprises 25-hydroxyvitamin $D_3$.

21. The formulation according to any of the preceding paragraphs, further comprising an oily vehicle.

22. The formulation according to paragraph 21, wherein the oily vehicle comprises mineral oil.

23. The formulation according to paragraph 22, wherein the formulation comprises about 20 wt % paraffin, about 20 wt % to about 25 wt % glycerol monostearate, about 10 wt % a mixture of lauroyl macrogolglycerides and lauroyl polyoxylglycerides, about 30 wt % to about 35 wt % mineral oil, and about 10 wt % to about 15 wt % hydroxyl propyl methylcellulose.

24. A formulation according to any one of the preceding paragraphs, wherein the formulation comprises glycerol monostearate.

25. A formulation according to any one of the preceding paragraphs, wherein the formulation comprises one or more polyglycolized glycerides.

26. A sustained release dosage form in the form of a capsule, tablet, sachet, dragee, or suppository comprising a formulation according to any one of the preceding paragraphs.

27. The dosage form according to paragraph 26, comprising a capsule or tablet.

28. The dosage form according to paragraph 27, comprising a capsule.

29. The dosage form according to paragraph 26, comprising an oral capsule, tablet, sachet, dragee.

30. A stabilized dosage form according to any one of the preceding paragraphs characterized by a dissolution profile providing a release of vitamin D compound of
less than 30% at 2 hours;
greater than 45% at 6 hours; and
greater than 80% at 12 hours.

31. The stabilized dosage form according to paragraph 26, wherein the release of vitamin D compound at 6 hours is less than 60%.

32. A stabilized sustained release oral dosage form comprising a vitamin D compound characterized by an in vitro dissolution profile providing release of vitamin D compound of
less than 30% at 100 to 140 minutes;
greater than 45% at 5 to 7 hours; and
greater than 80% at 11 to 13 hours.

33. The dosage form of paragraph 32, wherein the release of vitamin D compound is
less than 30% at 2 hours;
greater than 45% at 6 hours; and
greater than 80% at 12 hours.

34. The dosage form according to paragraph 32 or 33, wherein the release of vitamin D compound at 5 to 7 hours is less than 60%.

35. The dosage form according to paragraph 34, wherein the release of vitamin D compound at 6 hours is less than 60%.

36. A stabilized sustained release oral dosage form comprising a vitamin D compound characterized by an in vitro dissolution profile providing release of vitamin D compound of
about 20% to about 40% at 2 hours;
at least 35% at 6 hours; and
at least 70% at 12 hours.

37. The dosage form of paragraph 36, wherein the release of vitamin D compound is
about 25% to about 35% at 2 hours;
at least 40% at 6 hours; and
at least 75% at 12 hours.

38. The dosage form of paragraph 36 or 37, wherein the release of vitamin D compound is 75% or less at 6 hours.

39. The dosage form of paragraph 38, wherein the release of vitamin D compound is 65% or less at 6 hours.

40. The dosage form of paragraph 39, wherein the release of vitamin D compound is 60% or less at 6 hours.

41. A stabilized sustained release dosage form comprising a vitamin D compound characterized by a $t_{max}$ following administration of the dosage form to a human patient, of at least 4 hours.

42. The dosage form of paragraph 41, wherein the $t_{max}$ is at least 8 hours.

43. The dosage form of paragraph 42, wherein the $t_{max}$ is at least 12 hours.

44. The dosage form of paragraph 43, wherein the $t_{max}$ is at least 18 hours.

45. The dosage form of paragraph 44, wherein the $t_{max}$ is at least 20 hours.

46. The dosage form of paragraph 45, wherein the $t_{max}$ is at least 24 hours.

47. The dosage form of paragraph 46, wherein the $t_{max}$ is at least 28 hours.

48. The dosage form of paragraph 41, wherein the $t_{max}$ is in a range of 4 to 96 hours.

49. The dosage form of paragraph 48, wherein the $t_{max}$ is in a range of 18 to 30 hours.

50. The dosage form of paragraph 49, wherein the $t_{max}$ is in a range of 13 to 28 hours.

51. The dosage form of paragraph 50, wherein the $t_{max}$ is about 28 hours.

52. A stabilized sustained release dosage form comprising a 25-hydroxyvitamin D compound, the dosage form characterized by providing a baseline-adjusted $C_{max}$ per microgram of 25-hydroxyvitamin D in a range of about 0.0133 ng/mL to about 0.04 ng/mL when administered to an adult human.

53. A method of administering a stabilized sustained release dosage form comprising a 25-hydroxyvitamin D compound to a human patient, comprising administering an effective amount of the dosage form to the patient to provide a baseline-adjusted Cmax of at least about 0.2 ng/mL and less than 110 ng/mL.

54. The method of paragraph 53, comprising administering an effective amount of the dosage form to provide a baseline-adjusted Cmax in a range of about 0.2 to about 24 ng/mL.

55. A method of administering a stabilized sustained release dosage form comprising a 25-hydroxyvitamin D compound to a human patient, comprising administering an effective amount of the dosage form to the patient to provide a baseline-adjusted $AUC_{0-inf}$ of at least 52 ng*h/mL and less than 34500 ng*h/mL.

56. The method of paragraph 55, comprising administering an effective amount of the dosage form to the patient to provide a baseline-adjusted $AUC_{0-inf}$ in a range of about 52 ng*h/mL to about 12,000 ng*h/mL.

57. A method of vitamin D supplementation comprising administering to a subject in need thereof a formulation or dosage form according to any one of the preceding paragraphs.

58. A method of treatment or prophylaxis of a vitamin-D responsive disease in a subject comprising administering to the subject a formulation or dosage form according to any one of the preceding paragraphs.

59. The method of paragraph 58, wherein the disease is selected from cancer (e.g., breast, lung, skin, melanoma, colon, colorectal, rectal, prostate and bone cancer), autoimmune diseases, for example, type I diabetes, multiple sclerosis, rheumatoid arthritis, polymyositis, dermatomyositis, scleroderma, fibrosis, Grave's disease, Hashimoto's disease, acute or chronic transplant rejection, acute or chronic graft versus host disease, inflammatory bowel disease, Crohn's disease, systemic lupus erythematosis, Sjogren's Syndrome, eczema and psoriasis, dermatitis, including atopic dermatitis, contact dermatitis, allergic dermatitis and/or chronic dermatitis, inflammatory diseases, for example, asthma, chronic obstructive pulmonary disease, polycystic kidney disease, polycystic ovary syndrome, pancreatitis, nephritis, hepatitis, and/or infection, hypertension, cardiovascular diseases, for example, subjects with atherosclerosis, arteriosclerosis, coronary artery disease, cerebrovascular disease, peripheral vascular disease, myocardial infarction, myocardial ischemia, cerebral ischemia, stroke, congestive heart failure, cardiomyopathy, obesity or other weight disorders, lipid disorders (e.g. hyperlipidemia, dyslipidemia including associated diabetic dyslipidemia and mixed dyslipidemia hypoalphalipoproteinemia, hypertriglyceridemia, hypercholesterolemia, and low HDL (high density lipoprotein)), metabolic disorders (e.g. Metabolic Syndrome, Type II diabetes mellitus, Type I diabetes mellitus, hyperinsulinemia, impaired glucose tolerance, insulin resistance, diabetic complication including neuropathy, nephropathy, osteoporosis, retinopathy, diabetic foot ulcer and cataracts), and/or thrombosis.

60. The method of paragraph 59, wherein the disease is selected from (i) in the parathyroid—hypoparathyroidism, Pseudohypo-parathyroidism, secondary hyperparathyroidism; (ii) in the pancreas—diabetes; (iii) in the thyroid—medullary carcinoma; (iv) in the skin—psoriasis; wound healing; (v) in the lung—sarcoidosis and tuberculosis; (vi) in the kidney—chronic kidney disease, hypophosphatemic VDRR, vitamin D dependent rickets; (vii) in the bone—anticonvulsant treatment, fibrogenisis imperfecta ossium, osteitis fibrosa cystica, osteomalacia, osteoporosis, osteopenia, osteosclerosis, renal osteodytrophy, rickets; (viii) in the intestine—glucocorticoid antagonism, idopathic hypercalcemia, malabsorption syndrome, steatorrhea, tropical sprue; and (ix) autoimmune disorders.

61. The method of paragraph 60, wherein the disease is selected from cancer, dermatological disorders (for example psoriasis), parathyroid disorders (for example hyperparathyroidism and secondary hyperparathyroidism), bone disorders (for example osteoporosis) and autoimmune disorders.

62. The method of paragraph 61, wherein the disease is secondary hyperparathyroidism.

63. The method of paragraph 62, wherein the subject has chronic kidney disease (CKD).

64. The method of paragraph 63, wherein the CKD is Stage 3 or 4.

65. The method of paragraph 64, wherein the patient is vitamin-D deficient.

66. The method of any one of the preceding paragraphs, wherein the patient is human.

67. The method of paragraph 66, wherein the human is an adult human.

68. A composition as substantially herein described.

What is claimed:

1. A stabilized capsule formulation for extended release of a vitamin D compound in the gastrointestinal tract of a subject which ingests the formulation, the formulation comprising a mixture of:
   one or both of 25-hydroxyvitamin $D_2$ and 25-hydroxyvitamin $D_3$;
   a lipophilic matrix comprising an emulsifier;
   and an effective amount of a cellulosic stabilizing agent to maintain a difference of less than 30% between the amount of vitamin D compound released at any given time point after four hours during in vitro dissolution after two months exposure to storage conditions of 25° C. and 60% relative humidity and the amount released at the same dissolution time point during in vitro dissolution conducted prior to exposing the formulation to the storage conditions, wherein the cellulosic stabilizing agent is hydroxypropyl methylcellulose (HPMC), and the HPMC is present in an amount greater than 5 wt % and up to about 30 wt % of the formulation.

2. A stabilized oral capsule formulation for extended release of a vitamin D compound, said formulation comprising a mixture of:
   one or both of 25-hydroxyvitamin $D_2$ and 25-hydroxyvitamin $D_3$;
   a wax matrix comprising an emulsifier; and
   an effective amount of a cellulosic stabilizing agent to maintain a difference of less than 30% between the amount of vitamin D compound released at any given time point after four hours during in vitro dissolution testing after exposure for two months to storage conditions of 25° C. and 60% relative humidity and the amount released at the same dissolution time point during in vitro dissolution conducted prior to exposing the formulation to the storage conditions, wherein the cellulosic stabilizing agent is hydroxypropyl methylcellulose (HPMC), and the HPMC is present in an amount greater than 5 wt % and up to about 30 wt % of the formulation.

3. A stabilized capsule formulation for extended release of a vitamin D compound in the gastrointestinal tract of a subject which ingests the formulation, said formulation comprising a mixture of:
   an active-loaded wax matrix comprising one or both of 25-hydroxyvitamin $D_2$ and 25-hydroxyvitamin $D_3$ and an emulsifier; and
   a cellulosic stabilizing agent, wherein the cellulosic stabilizing agent is hydroxypropyl methylcellulose (HPMC), and the HPMC is present in an amount greater than 5 wt % and up to about 30 wt % of the formulation;
   wherein the formulation releases an amount of 25-hydroxyvitamin D during in vitro dissolution after two months exposure to storage of 25° C. and 60% relative humidity that varies at any given dissolution time point compared to the amount released at the same dissolution time point during in vitro dissolution conducted prior to exposing the formulation to the storage conditions by 30% or less in the absence of the cellulosic stabilizing agent.

4. In a capsule formulation comprising a 25-hydroxyvitamin D compound, a lipophilic matrix, and an emulsifier for extended release of the 25-hydroxyvitamin D compound in the gastrointestinal tract of a subject which ingests the formulation, the improvement comprising an effective amount of a cellulosic compound admixed in the formulation to maintain a change of less than 30% in the amount of 25-hydroxyvitamin D released during in vitro dissolution after exposure to storage conditions of at least one month at 25° C. and 60% relative humidity at any given dissolution time point after four hours compared to the amount released at the same dissolution time point during in vitro dissolution conducted prior to exposing the formulation to the storage conditions, wherein the cellulosic compound is hydroxypropyl methylcellulose (HPMC), and the HPMC is present in an amount greater than 5 wt % and up to about 30 wt % of the formulation.

5. The stabilized capsule formulation according to claim 1, wherein the formulation releases an amount of 25-hydroxyvitamin D during in vitro dissolution after exposure to storage conditions for 2 months at 25° C. and 60% relative humidity that varies at any given dissolution time point after four hours compared to the amount released at the same dissolution time point during in vitro dissolution conducted prior to exposing the formulation to the storage conditions, by 25% or less.

6. The stabilized capsule formulation according to claim 1, wherein the formulation releases an amount of 25-hydroxyvitamin D during in vitro dissolution after exposure to storage conditions for one month at 40° C. and 75% relative humidity that varies at any given dissolution time point after four hours compared to the amount released at the same dissolution time point during in vitro dissolution conducted prior to exposing the formulation to the storage conditions, by 30% or less.

7. The stabilized oral capsule formulation according to claim 2, wherein the matrix comprises a wax matrix comprising a controlled release agent, a lipophilic emulsifier, and an absorption enhancer.

8. The stabilized oral capsule formulation according to claim 7, wherein the controlled release agent comprises paraffin.

9. The stabilized oral capsule formulation according to claim 7, wherein the lipophilic emulsifier has a HLB value less than 7.

10. The stabilized oral capsule formulation according to claim 9, wherein the lipophilic emulsifier comprises glycerol monostearate.

11. The stabilized oral capsule formulation according to claim 7, wherein the absorption enhancer has a HLB value in a range of about 13 to about 18.

12. The stabilized oral capsule formulation according to claim 11, wherein the absorption enhancer comprises lauroyl polyoxylglycerides.

13. The stabilized capsule formulation according to claim 1, wherein the vitamin D compound comprises 25-hydroxyvitamin $D_3$.

14. The stabilized oral capsule formulation according to claim 7, further comprising an oily vehicle.

15. The stabilized oral capsule formulation according to claim 14, wherein the oily vehicle comprises mineral oil.

16. The stabilized oral capsule formulation according to claim 15, wherein the formulation comprises about 20 wt % paraffin, about 20 wt % to about 25 wt % glycerol monostearate, about 10 wt % lauroyl polyoxylglycerides, about 30 wt % to about 35 wt % mineral oil, and about 10 wt % to about 15 wt % HPMC.

17. A The stabilized oral capsule formulation according to claim 7, wherein the formulation comprises glycerol monostearate in an amount in a range of about 20 wt % to about 25 wt %.

18. A The stabilized oral capsule formulation according to claim 7, wherein the formulation comprises one or more polyglycolized glycerides.

19. A The stabilized capsule formulation according to claim 1 comprising a dissolution profile providing a release of a 25-hydroxyvitamin D compound of
less than 30% at 2 hours;
greater than 45% at 6 hours; and
greater than 80% at 12 hours.

20. A stabilized extended release oral capsule dosage form comprising a 25-hydroxyvitamin D compound, a lipophilic matrix, an emulsifier, and a cellulosic compound that increases the stability of the in vitro dissolution release profile of the dosage form wherein the cellulosic compound is hydroxypropyl methylcellulose (HPMC), and the HPMC is present in an amount greater than 5 wt % and up to about 30 wt % of the dosage form, wherein the dosage form comprises an in vitro dissolution profile providing release of the 25-hydroxyvitamin D compound of
less than 30% at 100 to 140 minutes;
greater than 45% at 5 to 7 hours; and
greater than 80% at 11 to 13 hours.

21. A stabilized extended release oral capsule dosage form comprising a 25-hydroxyvitamin D compound, a lipophilic matrix, an emulsifier and a cellulosic compound that increases the stability of the in vitro dissolution release profile of the dosage form wherein the cellulosic compound is hydroxypropyl methylcellulose (HPMC), and the HPMC is present in an amount greater than 5 wt % and up to about 30 wt % of the dosage form, wherein the dosage form comprises an in vitro dissolution profile providing release of the 25-hydroxyvitamin D compound of
about 20% to about 40% at 2 hours;
at least 35% at 6 hours; and
at least 70% at 12 hours.

22. A stabilized extended release capsule dosage form comprising a 25-hydroxyvitamin D compound, a lipophilic matrix, an emulsifier and a cellulosic compound that increases the stability of the in vitro dissolution release profile of the dosage form wherein the cellulosic compound is hydroxypropyl methylcellulose (HPMC), and the HPMC is present in an amount greater than 5 wt % and up to about 30 wt % of the dosage form, comprising a $t_{max}$ following administration of the dosage form to a human patient, of at least 4 hours.

23. A stabilized extended release capsule dosage form comprising a 25-hydroxyvitamin D compound, a lipophilic matrix, an emulsifier and a cellulosic compound that increases the stability of the in vitro dissolution release profile of the dosage form wherein the cellulosic compound is hydroxypropyl methylcellulose (HPMC), and the HPMC is present in an amount greater than 5 wt % and up to about 30 wt % of the dosage form, the dosage form providing a baseline-adjusted $C_{max}$ per microgram of 25-hydroxyvitamin D in a range of about 0.0133 ng/mL to about 0.04 ng/mL when administered to an adult human.

24. The stabilized oral capsule formulation according to claim 16, wherein the formulation comprises about 30 μg to about 90 μg 25-hydroxyvitamin $D_3$, about 20 wt % paraffin, about 23 wt % glycerol monostearate, about 10 wt % lauroyl polyoxylglycerides, about 35 wt % mineral oil, and about 10 wt % HPMC.

25. The stabilized oral capsule formulation according to claim 24, wherein the formulation comprises 30 μg 25-hydroxyvitamin $D_3$.

26. The stabilized oral capsule formulation according to claim 24, wherein the formulation comprises 60 μg 25-hydroxyvitamin $D_3$.

27. The stabilized oral capsule formulation according to claim 24, wherein the formulation comprises 90 μg 25-hydroxyvitamin $D_3$.

28. The stabilized oral capsule formulation according to claim 16, wherein the formulation comprises about 30 μg to about 90 μg 25-hydroxyvitamin $D_3$, about 20 wt % paraffin, about 23 wt % glycerol monostearate, about 10 wt % lauroyl polyoxylglycerides, about 30 wt % mineral oil, and about 15 wt % HPMC.

29. The stabilized oral capsule formulation according to claim 28, wherein the formulation comprises 30 μg 25-hydroxyvitamin $D_3$.

30. The stabilized oral capsule formulation according to claim 28, wherein the formulation comprises 60 μg 25-hydroxyvitamin $D_3$.

31. The stabilized oral capsule formulation according to claim 28, wherein the formulation comprises 90 μg 25-hydroxyvitamin $D_3$.

32. The stabilized extended release capsule dosage form of claim 22, wherein the dosage form comprises 100 μg to 200 μg 25-hydroxyvitamin $D_3$.

33. The stabilized extended release capsule dosage form of claim 22, wherein the dosage form comprises an effective amount of a cellulosic stabilizing agent to maintain a difference of less than 30% between the amount of vitamin D compound released at any given time point after four hours during in vitro dissolution after six months exposure to storage conditions of 25° C. and 60% relative humidity and the amount released at the same dissolution time point during in vitro dissolution conducted prior to exposing the formulation to the storage conditions.

34. The stabilized extended release capsule dosage form of claim 33, wherein the difference is less than 20%.

35. The stabilized extended release capsule dosage form of claim 22, wherein the dosage form comprises an effective amount of a cellulosic stabilizing agent to maintain a difference of less than 30% between the amount of vitamin D compound released at any given time point after four hours during in vitro dissolution after six months exposure to storage conditions of 40° C. and 75% relative humidity and the amount released at the same dissolution time point during in vitro dissolution conducted prior to exposing the formulation to the storage conditions.

36. The stabilized extended release capsule dosage form of claim 35, wherein the difference is less than 20%.

* * * * *